United States Patent [19]

Housley et al.

[11] Patent Number: 5,047,432
[45] Date of Patent: Sep. 10, 1991

[54] ARYLCYCLOBUTYLMETHYLAMINE THERAPEUTIC AGENTS

[75] Inventors: John R. Housley, Breaston; James E. Jeffery, Chilwell; David N. Johnston, Arnold; Bruce J. Sargent, Carlton, all of England

[73] Assignee: The Boots Company Plc, Nottingham, England

[21] Appl. No.: 541,174

[22] Filed: Jun. 20, 1990

Related U.S. Application Data

[63] Continuation of Ser. No. 346,252, May 1, 1989, abandoned, which is a continuation of Ser. No. 818,547, Jan. 13, 1986, abandoned.

[30] Foreign Application Priority Data

Jan. 17, 1985 [GB] United Kingdom ............... 01192

[51] Int. Cl.$^5$ .................. A61K 31/135; C07C 211/08
[52] U.S. Cl. ................................. 514/650; 564/368; 564/337; 564/338; 516/209; 516/236; 516/240; 544/87; 544/158; 544/170; 544/174; 514/231.8; 514/239.2; 514/238.8; 514/320; 514/317
[58] Field of Search ............. 564/368, 337, 338; 544/158, 170, 174, 87; 546/240, 236, 209; 514/231.8, 239.2, 238.8, 326, 317, 649, 650

[56] References Cited

U.S. PATENT DOCUMENTS

| | | | |
|---|---|---|---|
| 3,054,822 | 9/1962 | Schorr et al. | 564/355 X |
| 3,573,304 | 3/1971 | Eberle et al. | 564/355 X |
| 3,706,764 | 12/1972 | Nakanishi et al. | 564/381 X |
| 4,443,449 | 4/1984 | Jeffery et al. | 514/646 X |
| 4,522,828 | 6/1985 | Jeffery et al. | 514/247 X |
| 4,629,727 | 12/1986 | Kozlik et al. | 564/308 X |

FOREIGN PATENT DOCUMENTS

| | | |
|---|---|---|
| 0089089 | 9/1983 | European Pat. Off. |
| 973887 | 10/1964 | United Kingdom. |
| 1530172 | 10/1978 | United Kingdom. |
| 2127819 | 4/1984 | United Kingdom ............... 564/338 |
| 2128991 | 5/1984 | United Kingdom ............... 564/338 |

OTHER PUBLICATIONS

"Synthesis of New Heterocycles: Part XV—Synthesis of Novel Cyclic and Acyclic Sulphamides", Ind. Jrnl. Chem., vol. 14B, pp. 766-769 (1976).
"Substituted Acetic Acids XXXII—Army. Khim. Zhurnal", vol. 29, No. 2, pp. 194-199 (1976), A. Mndzhoyan et al.
Israel J. Chem. 5(5), pp. 223-229 (1967), "1-phenylcycloalkylamine Derivatives I", A. Kalir et al.
"1-Phenylcycloalkylamine Derivatives II", J. Med. Chem. 12, pp. 473-477 (1969), A. Kalir, H. Edery, Z. Pelah, D. Balderman and Gila Porath.
"1-Phenylcycloalkylamine Derivatives III", Israel J. Chem. 13(2), pp. 125-136 (1975), A. Kalir, S. Sadeh, H. Karoly, E. Shirin, D. Balderman.
Goodman and Gillman's "The Pharmacological Basics of Therapeutics", 7 ed., pp. 12 to 21 (1978).
Usdin, "Metabolic Pathways for Antipsychotic Drugs", Psychopharmacology, pp. 895-902 (1978).
Clarke, "Isolation and Identification of Drugs", Pharmaceutical Press, 1986, pp. 284-292.
D. H. Schroeder, J. Clin. Psychiatry 44 (5) Sect. 2, pp. 79-81 (1983).
Poyner "In Consideration of Active Metabolites", J. Clin. Pharmacology, 27, pp. 167-168 (1987).
"Bupropion: Possible Role of Major Metabolites in Mode of Action", Clin. Pharmacol. Ther. (37, No. 2, 187,1985), Cooper et al.

Primary Examiner—Richard L. Raymond
Assistant Examiner—Mark Russell
Attorney, Agent, or Firm—Armstrong, Nikaido, Marmelstein, Kubovcik & Murray

[57] ABSTRACT

Compounds of formula I

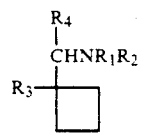

and pharmaceutically acceptable salts thereof; in which
$R_1$ and $R_2$, which are the same or different, are H or an optionally substituted hydrocarbon group or $R_1$ and $R_2$ together with the nitrogen atom to which they are attached form an optionally substituted heterocyclic ring;
$R_3$ is an optionally substituted aromatic hydrocarbon group; and
$R_4$ is a hydrocarbon group containing at least one substituent selected from the group consisting of hydroxy and acylated derivatives thereof, optionally substituted alkoxy groups, optionally substituted cycloalkyloxy groups, optionally substituted alkylenedioxy groups, oxo and groups of formula $S(O)_pR_5$ in which p is 0, 1 or 2 and $R_5$ is an alkyl group, said hydrocarbon group being optionally substituted by additional substituents, are useful in the treatment of depression.

15 Claims, No Drawings

ARYLCYCLOBUTYLMETHYLAMINE THERAPEUTIC AGENTS

This application is a continuation of application Ser. No. 346,252 filed May 1, 1989; which is a continuation of Ser. No. 818,547 filed Jan. 13, 1986, now abandoned.

The present invention relates to novel therapeutic agents, and in particular to arylcyclobutylalkylamines, to processes for their preparation, to pharmaceutical compositions containing them and to their use in the treatment of depression.

The present invention provides compounds of formula I

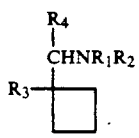

and pharmaceutically acceptable salts thereof; in which
$R_1$ and $R_2$, which may be the same or different, are H or an optionally substituted hydrocarbon group or $R_1$ and $R_2$ together with the nitrogen atom to which they are attached form an optionally substituted heterocyclic ring;
$R_3$ is an optionally substituted aromatic hydrocarbon group; and
$R_4$ is a hydrocarbon group containing at least one substituent selected from the group consisting of hydroxy and acylated derivatives thereof, optionally substituted alkoxy groups, optionally substituted cycloalkyloxy groups, optionally substituted alkylenedioxy groups, oxo and groups of formula $S(O)_pR_5$ in which p is 0, 1 or 2 and $R_5$ is an alkyl group, said hydrocarbon group being optionally substituted by additional substituents.

In preferred compounds of formula I, $R_1$ and/or $R_2$ may be H, alkyl groups preferably containing 1 to 6 carbon atoms or cycloalkyl groups preferably containing 3 to 6 carbon atoms. When $R_1$ and/or $R_2$ are alkyl groups, the groups may be straight or branched and are optionally substituted. Suitable alkyl groups contain 1 to 4 carbon atoms for example methyl, ethyl, propyl, isopropyl, butyl, sec-butyl, isobutyl and tert-butyl. When $R_1$ and/or $R_2$ are cycloalkyl groups, the groups may be cyclopropyl, cyclobutyl, cyclopentyl or cyclohexyl. When $R_1$ and/or $R_2$ are substituted alkyl groups, the alkyl group is, for example, an ethyl group which is substituted by a hydroxy group or an alkoxy group (e.g. methoxy), or a methyl or ethyl group substituted by a carbocyclic group (e.g. a phenyl or cyclopropyl group) or a heterocyclic group (e.g. a morpholino group). In particularly preferred compounds of formula I the group $NR_1R_2$ is amino, N-methylamino, N,N-dimethylamino, N,N-diethylamino, N-propylamino, N-isobutylamino, N-tert-butylamino, N-butyl-N-methylamino, N-(2-morpholinoethyl)amino, N-methyl-N-(2-morpholinoethyl)amino, N-(2-methoxyethyl)amino, N-benzylamino, N-(2-hydroxyethyl)amino, N-(cyclopropylmethyl)amino, N-cyclohexyl-N-methylamino. In especially preferred compounds of formula I, the group $NR_1R_2$ is amino, N-methylamino or N,N-dimethylamino.

In preferred compounds of formula I in which $R_1$ and $R_2$ together with the nitrogen atom to which they are attached form an optionally substituted heterocyclic ring, the heterocyclic ring contains 5 to 7 atoms which may be for example (a) the nitrogen atom to which $R_1$ and $R_2$ are attached and 4 or 5 carbon atoms or (b) the nitrogen atom to which $R_1$ and $R_2$ are attached and an additional optionally alkylated nitrogen atom or an oxygen atom and 4 carbon atoms. The heterocyclic ring optionally contains one or more double bonds and is optionally substituted by, for example, one or more alkyl (e.g. methyl) groups. In particularly preferred compounds of formula I, the group $NR_1R_2$ is a pyrrolidinyl, piperidino, morpholino, tetrahydropyridyl or methylpiperidino group. In especially preferred compounds of formula I, the group $NR_1R_2$ is a pyrrolidinyl, piperidino, morpholino, 1,2,3,6-tetrahydropyridyl or 4-methylpiperidino group.

The group $R_3$ in compounds of formula I may be an optionally substituted phenyl group, an optionally substituted naphthyl group or an optionally substituted phenanthryl group. In preferred compounds of formula I, the group $R_3$ is phenyl, naphthyl or a substituted phenyl group preferably containing from 1 to 3 substituents, each of which may be halo, trifluoromethyl, an alkyl group preferably containing 1 to 3 carbon atoms, an alkoxy group preferably containing 1 to 3 carbon atoms, an alkylthio group preferably containing 1 to 3 carbon atoms or an optionally substituted phenyl group. When the group $R_3$ is a substituted phenyl group containing two or more substituents, those substituents may be the same or different. In particularly preferred compounds of formula I, $R_3$ is phenyl, naphthyl or phenyl substituted by one or more fluoro, chloro, bromo, trifluoromethyl, methyl, methoxy, methylthio or phenyl groups. In especially preferred compounds of formula I, $R_3$ is phenyl, 2-naphthyl, 4-chlorophenyl, 3-chlorophenyl, 3,4-dichlorophenyl, 4-bromophenyl, 4-fluorophenyl, 3-fluorophenyl, 2-fluorophenyl, 4-methylphenyl, 4-methoxyphenyl, 4-methylthiophenyl, 3-trifluoromethylphenyl, 3-chloro-5-methylphenyl, 3,5-dichloro-4-methoxyphenyl or 4-biphenylyl.

In preferred compounds of formula I the group $R_4$ comprises a straight or branched, saturated or unsaturated aliphatic group of 1 to 16 carbon atoms containing at least one substituent selected from the group consisting of hydroxy and acylated derivatives thereof, optionally substituted alkoxy groups, optionally substituted cycloalkyloxy groups, optionally substituted alkylenedioxy groups, oxo and groups of formula $S(O)_pR_5$. The aliphatic group is optionally substituted by one or more additional substituents which may be optionally substituted cycloalkyl groups preferably containing 3 to 6 carbon atoms (e.g. cyclopropyl or cyclohexyl), heterocyclic groups (e.g. morpholino) or halo (e.g. fluoro). When more than one additional substituent is present on the aliphatic group, the additional substituents may be the same or different and may be on the same or different carbon atoms. In preferred compounds of formula I, the additional substituent is selected from the group consisting of cyclopropyl, cyclohexyl, fluoro and morpholino.

In preferred compounds of formula I in which the group $R_4$ comprises a straight or branched saturated or unsaturated aliphatic group substituted by hydroxy, the group may contain up to 10 carbon atoms and is optionally substituted. In particularly preferred compounds of formula I, the aliphatic group contains 2 to 7 carbon atoms and is optionally substituted by, for example, halo (e.g. fluoro), heterocyclic (e.g. morpholino) groups or cycloalkyl (e.g. cyclopropyl) groups. In especially preferred compounds of formula I, in which the group $R_4$ contains one hydroxy, $R_4$ is 1-hydroxyethyl, 1-hydroxypropyl, 3-hydroxypropyl, 1-hydroxy-1-methyl-ethyl, 1-hydroxybutyl, 1-hydroxy-1-methylpropyl, 1-hydroxy-2-methylpropyl, 2-hydroxy-2-methylpropyl, 2-cyclopropyl-2-hydroxypropyl, 2-hydroxy-2-methyl-3-morpholinopropyl, 2-hydroxy-2-trifluoromethylpropyl, 2-hydroxy-1,2-dimethylpropyl, 2-hydroxybutyl, 4-hydroxybutyl, 1-hydroxy-3-methylbutyl, 2-hydroxy-2-methylbutyl, 2-ethyl-2-hydroxybutyl, 2-ethyl-2-hydroxy-3-methylbutyl, 2-hydroxy-2,3,3-trimethylbutyl, 4-hydroxypentyl, 2-hydroxy-2-methylpentyl, 2-hydroxy-2,4-dimethylpentyl, 6-hydroxyhexyl, 1-hydroxy-5-hexenyl or 6-hydroxyheptyl. When the hydroxy is acylated, the acyl group may contain 2 to 4 carbon atoms and is optionally substituted for example by an alkoxy group. In particularly preferred compounds in which the group $R_4$ contains an acylated hydroxy derivative, the acyl group is acetyl or methoxyacetyl. In especially preferred acylated compounds of formula I, $R_4$ is a 4-(acetoxy)butyl or 4-(methoxyacetoxy)butyl group.

In one particularly preferred group of compounds of formula I, $R_4$ is a group of formula II

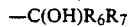
$$—C(OH)R_6R_7 \qquad II$$

in which $R_6$ is H, an alkyl group containing 1 to 3 carbon atoms and $R_7$ is a straight or branched, saturated or unsaturated aliphatic group containing 1 to 5 carbon atoms. In particularly preferred compounds of formula I in which $R_4$ is a group of formula II, $R_6$ is H, methyl or ethyl and $R_7$ is methyl, ethyl, propyl, isopropyl, isobutyl or pentenyl. In especially preferred compounds of formula I in which $R_4$ is a group of formula II, $R_4$ is 1-hydroxyethyl, 1-hydroxypropyl, 1-hydroxy-1-methylethyl, 1-hydroxybutyl, 1-hydroxy-1-methylpropyl, 1-hydroxy-2-methylpropyl, 1-hydroxy-3-methylbutyl, 1-hydroxy-5-hexenyl.

In a further particularly preferred group of compounds of formula I, $R_4$ is a group of formula III

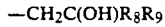
$$—CH_2C(OH)R_8R_9 \qquad III$$

in which $R_8$ is H or an optionally substituted alkyl group which may be straight or branched and which preferably contains 1 to 4 carbon atoms and $R_9$ is an optionally substituted alkyl group which may be straight or branched and which preferably contains 1 to 4 carbon atoms or an optionally substituted cycloalkyl group preferably containing 3 to 6 carbon atoms. The substituents may be halo (e.g. fluoro), optionally substituted alkoxy (e.g. methoxy or ethoxy), alkylthio (e.g. methylthio) or heterocyclic (e.g. morpholino) groups. In particularly preferred compounds of formula I in which $R_4$ is a group of formula III, $R_8$ is H, methyl, ethyl or propyl and $R_9$ is methyl, ethyl, propyl, isobutyl, tert-butyl, cyclopropyl, trifluoromethyl, 1-methylthioethyl, methoxymethyl, ethoxymethyl 2-methoxyethyl, 2-ethoxyethyl or morpholinomethyl. In especially preferred compounds of formula I in which $R_4$ is a group of formula III, $R_4$ is 2-hydroxy-2-methyl-propyl, 2-hydroxy-2-methyl-3-morpholinopropyl, 2-hydroxy-2-trifluoromethylpropyl, 2-cyclopropyl-2-hydroxypropyl, 2-hydroxy-2-methylbutyl, 2-ethyl-2-hydroxy-3-methylbutyl, 2-ethyl-2-hydroxybutyl, 2-hydroxy-2,3,3-trimethylbutyl, 2-hydroxy-2-methyl-3-methylthiobutyl, 2-hydroxy-2-methylpentyl, 2-hydroxy-2,4-dimethyl-pentyl, 2-hydroxy-3-methoxy-2-methylpropyl, 2-hydroxy-2-(methoxymethyl)butyl, 2-(ethoxymethyl)-2-hydroxybutyl, 2-hydroxy-2-(methoxymethyl)pentyl, 2-hydroxy-4-methoxy-2-methylbutyl, 2-ethyl-2-hydroxy-4-methoxybutyl or 4-ethoxy-2-hydroxy-2-methylbutyl.

In preferred compounds of formula I in which the group $R_4$ comprises a straight or branched aliphatic group substituted by an alkoxy group, the aliphatic group contains 1 to 12 carbon atoms and the alkoxy group, which may be straight or branched, contains 1 to 10 carbon atoms and is optionally substituted, for example by hydroxy, oxo a further optionally substituted alkoxy group, an optionally substituted carbamoyl group (e.g. carbamoyl, alkylcarbamoyl or dialkylcarbamoyl or 3-oxapentamethylenecarbamoyl), a carbocyclic (e.g. cyclohexyl) group or a heterocyclic (e.g. pyridyl) group. In particularly preferred compounds of formula I the aliphatic group contains up to 8 carbon atoms and the alkoxy group is a methoxy, ethoxy, propoxy, isopropoxy, dimethylpropoxy, hexyloxy, octyloxy, carbamoylmethoxy, 3-oxapentamethylenecarbamoylmethoxy, methoxyethoxy, cyclohexylethoxy pyridylethoxy, hydroxypropoxy or oxopropoxy group. In especially preferred compounds of formula I, $R_4$ is methoxymethyl, 2-methoxyethyl, 3-methoxypropyl, 3-methoxy-2-methylpropyl, 3-(2-methoxyethoxy)propyl, 3-(1,1-dimethylpropoxy)propyl, 3-(2-cyclohexylethoxy)-propyl, 3-[2-(4-pyridyl)ethoxy]propyl, 3-(2-hydroxypropoxy)propyl, 3-(2-oxopropoxy)propyl, 3-carbamoylmethoxy)propyl, 3-(3-oxapentamethylenecarbamoylmethoxy)propyl, 2-(methoxymethyl)-butyl, 4-methoxybutyl, 3-methoxybutyl, 4-ethoxybutyl, 6-methoxyhexyl, 3-ethoxypropyl, 3-propoxypropyl, 3-isopropoxypropyl, 3-hexyloxypropyl, 3-octyloxypropyl or 8-methoxyoctyl.

In preferred compounds of formula I in which the group $R_4$ comprises a straight or branched aliphatic group substituted by a cycloalkyloxy group, the aliphatic group contains 1 to 10 carbon atoms and the cycloalkyloxy group contains 3 to 6 carbon atoms. In particularly preferred compounds of formula I, the aliphatic group contains up to 3 carbon atoms and the cycloalkyloxy group is cyclopentyloxy. In especially preferred compounds of formula I, $R_4$ is 3-cyclopentyloxypropyl.

In preferred compounds of formula I in which the group $R_4$ comprises an aliphatic group substituted by an alkylenedioxy group, the aliphatic group contains 1 to 12, preferably 1 to 8, carbon atoms and the alkylenedioxy group is of formula $—O(CH_2)_mO—$ in which m is 2 or 3, preferably 2, and both oxygen atoms are attached to the same carbon atom of the aliphatic group. In especially preferred compounds of formula I, $R_4$ is a 3-(2-methyl-1,3-dioxolan-2-yl)propyl group.

In preferred compounds of formula I in which the group $R_4$ comprises an aliphatic group substituted by oxo, the group $R_4$ contains a ketonic group and the aliphatic group, which may be saturated or unsaturated, contains 1 to 12 carbon atoms. The aliphatic group is optionally substituted by one or more cycloalkyl groups (e.g. cyclohexyl). In especially preferred compounds of formula I, $R_4$ is 1-oxoethyl, 1-oxopropyl, 2-methyl-1-oxopropyl, 1-oxobutyl, 3-methyl-1-oxobutyl, 1-oxopentyl, 4-methyl-1-oxopentyl, 4-oxopentyl, 1-oxohexyl, 4-methyl-5-oxohexyl, 1-oxo-5-hexenyl, 1-oxoheptyl, 6-oxoheptyl, 1-oxooctyl, 1-oxo-8-nonenyl, 8-oxononyl, cyclohexylcarbonyl, 2-cyclohexyl-1-oxoethyl.

A group of particularly preferred compounds of formula I are ketones in which $R_4$ is a group of formula IV $$-COR_{10} \qquad\qquad IV$$

in which $R_{10}$ is a saturated or unsaturated aliphatic group containing 1 to 12 carbon atoms or a cycloalkyl or cycloalkylalkyl group. In especially preferred compounds of formula I in which $R_4$ is a group of formula IV, $R_{10}$ is methyl, ethyl, propyl, isopropyl, butyl, isobutyl, 3-methylbutyl, pentyl, hexyl, heptyl, 4-pentenyl, 7-octenyl, cyclohexyl or cyclohexylmethyl.

In preferred compounds of formula I in which the group $R_4$ comprises an aliphatic group substituted by a group of formula $S(O)_pR_5$, $R_5$ is an alkyl group containing 1 to 3 carbon atoms and the aliphatic group contains 1 to 3 carbon atoms. In especially preferred compounds of formula I, $R_4$ is methylthiomethyl, 3-methylthiopropyl, 3-methylsulphinylpropyl or methylsulphonylmethyl.

In compounds of formula I in which the group $R_4$ contains more than one substituent selected from the group consisting of hydroxy and acylated derivatives thereof, optionally substituted alkoxy groups, optionally substituted cycloalkyloxy groups, optionally substituted alkylenedioxy groups, oxo or groups of formula $S(O)_pR_5$, the substituents, which may be the same or different, are on different carbon atoms of the aliphatic group. Examples of such compounds include compounds of formula I in which $R_4$ is 3,4-dihydroxybutyl, 4,7-dioxooctyl, 2-hydroxy-3-methoxy-2-methylpropyl, 2-hydroxy-2-(methoxymethyl)butyl, 2-(ethoxymethyl)-2-hydroxybutyl, 2-hydroxy-2-(methoxymethyl)pentyl, 2-hydroxy-4-methoxy-2-methylbutyl, 2-ethyl-2-hydroxy-4-methoxybutyl, 4-ethoxy-2-hydroxy-2-methylbutyl, 2-hydroxy-2-methyl-3-methylthiobutyl, 4-hydroxy-1-oxobutyl, 4-acetoxy-1-oxobutyl, 4-methoxy-1-oxobutyl or 4-methoxy-1-oxopentyl.

Compounds of formula I may exist as salts with pharmaceutically acceptable acids. Examples of such salts include hydrochlorides, hydrobromides, sulphates, nitrates, maleates, acetates, citrates, fumarates, tartrates, succinates, benzoates and salts with acidic amino acids such as glutamic acid. Such salts may exist in the form of solvates (for example hydrates).

Compounds of formula I contain one or more asymmetric carbon atoms and exist in different optically active forms. When the compounds of formula I contain one chiral centre the compounds exist in two enantiomeric forms and the present invention includes both enantiomeric forms and mixtures thereof. When the compounds of formula I contain more than one chiral centre, the compounds may exist in diastereoisomeric forms. The present invention includes each of these diastereoisomeric forms and mixtures thereof.

Some compounds of formula I may exist in the form of geometric isomers and the present invention includes all of these geometric isomers and mixtures thereof.

Specific compounds of formula I are:
1-[1-(3,4-Dichlorophenyl)cyclobutyl]-1-dimethylaminopropan-2-one
1-Dimethylamino-1-(1-phenylcyclobutyl)propan-2-one
1-[1-(4-Bromophenyl)cyclobutyl]-1-dimethylaminobutan-2-one
1-[1-(3-Chloro-5-methylphenyl)cyclobutyl]-1-dimethylaminobutan-2-one
1-[1-(3,5-Dichloro-4-methoxyphenyl)cyclobutyl]-1-dimethylaminobutan-2-one
1-[1-(4-Methoxyphenyl)cyclobutyl]-1-dimethylaminobutan-2-one
1-[1-(4-Biphenylyl)cyclobutyl]-1-dimethylaminobutan-2-one
1-Dimethylamino-1-[1-(3-trifluoromethylphenyl)cyclobutyl]butan-2-one
1-Dimethylamino-1-[1-(2-naphthyl)cyclobutyl]butan-2-one
1-Dimethylamino-1-[1-(4-methylthiophenyl)cyclobutyl]-butan-2-one
1-[1-(4-Chlorophenyl)cyclobutyl]-1-dimethylaminopentan-2-one
1-Dimethylamino-1-[1-(3-trifluoromethylphenyl)cyclobutyl]-pentan-2-one
1-Dimethylamino-1-[1-(2-fluorophenyl)cyclobutyl]pentan-2-one
1-Dimethylamino-1-[1-(2-naphthyl)cyclobutyl]pentan-2-one
1-Dimethylamino-1-[1-(4-methoxyphenyl)cyclobutyl]pentan-2-one
1-Dimethylamino-1-[1-(4-tolyl)cyclobutyl]pentan-2-one
1-[1-(4-Biphenylyl)cyclobutyl]-1-dimethylaminopentan-2-one
1-Dimethylamino-1-(1-phenylcyclobutyl)pentan-2-one
1-[1-(4-Chlorophenyl)cyclobutyl]-1-dimethylaminohexan-2-one
1-[1-(3,4-Dichlorophenyl)cyclobutyl]-1-dimethylaminohexan-2-one
1-[1-(3,4-Dichlorophenyl)cyclobutyl]-1-dimethylamino-4-methylpentan-2-one
1-[1-(3,4-Dichlorophenyl)cyclobutyl]-1-dimethylamino-5-methylhexan-2-one
1-[1-(3,4-Dichlorophenyl)cyclobutyl]-1-dimethylamino-6-hepten-2-one
1-Dimethylamino-1-(1-phenylcyclobutyl)-6-hepten-2-one
1-[1-(4-Chlorophenyl)cyclobutyl]-1-dimethylamino-6-hepten-2-one
1-[1-(3,4-Dichlorophenyl)cyclobutyl]-1-dimethylaminooctan-2-one
1-[1-(4-Chlorophenyl)cyclobutyl]-1-dimethylaminooctan-2-one
1-[1-(4-Chlorophenyl)cyclobutyl]-1-dimethylaminononan-2-one
1-[1-(4-Chlorophenyl)cyclobutyl]-1-dimethylamino-9-decen-2-one
3-Cyclohexyl-1-[1-(3,4-dichlorophenyl)cyclobutyl]-1-dimethylaminopropan-2-one
1-[1-(4-Chlorophenyl)cyclobutyl]-1-dimethylamino-5-methoxypentan-2-one
1-[1-(4-Chlorophenyl)cyclobutyl]-1-dimethylamino-5-methoxyhexan-2-one
1-[1-(3,4-Dichlorophenyl)cyclobutyl]-1-dimethylamino-5-methoxyhexan-2-one
1-(N-tert-Butylamino)-1-[1-(3,4-dichlorophenyl)cyclobutyl]propan-2-one
1-(N-Butyl-N-methylamino)-1-[1-(3,4-dichlorophenyl)cyclobutyl]propan-2-one
1-[1-(3,4-Dichlorophenyl)cyclobutyl]-1-morpholinopropan-2-one
1-[1-(3,4-Dichlorophenyl)cyclobutyl]-1-(4-methylpiperidino)butan-2-one
1-[1-(3,4-Dichlorophenyl)cyclobutyl]-1-(N-methyl-N-2-morpholinoethylamino)butan-2-one
1-[1-(3,4-Dichlorophenyl)cyclobutyl]-1-[N-(2-hydroxyethyl)-N-methylamino]butan-2-one 1-[1-(3,4-Dichlorophenyl)cyclobutyl]-1-(1,2,3,6-tetrahydro-1-pyridyl)butan-2-one
1-(N-Cyclohexyl-N-methylamino)-1-[1-(3,4-dichlorophenyl)cyclobutyl]butan-2-one
1-(N-Methyl-N-2-morpholinoethylamino)-1-[1-(3-trifluoromethylphenyl)cyclobutyl]butan-2-one
1-[1-(3,4-Dichlorophenyl)cyclobutyl]-1-piperidinobutan-2-one
1-[1-(4-Chlorophenyl)cyclobutyl]-1-diethylaminobutan-2-one
1-[1-(3,4-Dichlorophenyl)cyclobutyl]-1-dimethylamino-5-hydroxypentan-2-one
5-[1-(3,4-Dichlorophenyl)cyclobutyl]-5-dimethylamino-4-oxopentyl acetate
1-[1-(4-Chlorophenyl)cyclobutyl]-1-dimethylaminopropan-2-one
1-[1-(4-Chlorophenyl)cyclobutyl]-1-dimethylaminobutan-2-one
1-[1-(4-Chlorophenyl)cyclobutyl]-1-dimethylamino-3-methylbutan-2-one
1-[1-(3,4-Dichlorophenyl)cyclobutyl]-1-dimethylaminobutan-2-one
1-[1-(4-Chlorophenyl)cyclobutyl]-1-dimethylaminoheptan-2-one
1-Cyclohexyl-2-[1-(3,4-dichlorophenyl)cyclobutyl]-2-dimethylaminoethanone
6-[1-(3,4-Dichlorophenyl)cyclobutyl]-6-dimethylaminohexan-2-one
8-[1-(4-Chlorophenyl)cyclobutyl]-8-dimethylaminooctan-2-one
8-[1-(3,4-Dichlorophenyl)cyclobutyl]-8-dimethylaminooctan-2-one
10-[1-(4-Chlorophenyl)cyclobutyl]-10-dimethylaminodecan-2-one
10-[1-(3,4-Dichlorophenyl)cyclobutyl]-10-dimethylaminodecan-2-one
N,N-Dimethyl-1-[1-(3,4-dichlorophenyl)cyclobutyl]-4-(2-methyl-1,3-dioxolan-2-yl)butylamine
7-[1-(4-Chlorophenyl)cyclobutyl]-7-dimethylamino-3-methylheptan-2-one
9-[1-(3,4-Dichlorophenyl)cyclobutyl]-9-dimethylaminononane-2,5-dione
1-[1-(4-Chlorophenyl)cyclobutyl)-1-dimethylaminopropan-2-ol
1-[1-(4-Chlorophenyl)cyclobutyl]-1-dimethylaminobutan-2-ol
1-[1-(4-Chlorophenyl)cyclobutyl]-1-dimethylamino-3-methylbutan-2-ol
6-[1-(3,4-Dichlorophenyl)cyclobutyl]-6-dimethylaminohexan-2-ol
8-[1-(3,4-Dichlorophenyl)cyclobutyl]-8-dimethylaminooctan-2-ol
1-[1-(3,4-Dichlorophenyl)cyclobutyl]-1-dimethylamino-6-hepten-2-ol
1-Dimethylamino-1-[1-(3-trifluoromethylphenyl)cyclobutyl]pentan-2-ol
1-Dimethylamino-1-[1-(4-tolyl)cyclobutyl]pentan-2-ol
1-[1-(3,4-Dichlorophenyl)cyclobutyl]-1-morpholinopropan-2-ol
1-[1-(3,4-Dichlorophenyl)cyclobutyl]-1-dimethylamino-4-methylpentan-2-ol
1-(N-Butyl-N-methylamino)-1-[1-(3,4-dichlorophenyl)cyclobutyl]propan-2-ol
1-(N-Cyclohexyl-N-methylamino)-1-[1-(3,4-dichlorophenyl)cyclobutyl]butan-2-ol
1-Dimethylamino-1-[1-(2-naphthyl)cyclobutyl]butan-2-ol
1-Dimethylamino-1-[1-(3-trifluoromethylphenyl)cyclobutyl]butan-2-ol
1-Dimethylamino-1-[1-(4-methoxyphenyl)cyclobutyl]-butan-2-ol
1-[1-(3,4-Dichlorophenyl)cyclobutyl]-1-piperidinobutan-2-ol
1-(N-Methyl-N-2-morpholinoethylamino)-1-[1-(3-trifluoromethylphenyl)cyclobutyl]butan-2-ol
1-[1-(4-Chlorophenyl)cyclobutyl]-1-diethylaminobutan-2-ol
1-[1-(4-Bromophenyl)cyclobutyl]-1-dimethylaminobutan-2-ol
1-[1-(3,4-Dichlorophenyl)cyclobutyl]-1-piperidinopropan-2-ol
1-[1-(4-Chlorophenyl)cyclobutyl]-1-dimethylamino-2-methylpropan-2-ol
1-[1-(4-Chlorophenyl)cyclobutyl]-1-dimethylamino-2-methylbutan-2-ol
4-Amino-4-[1-(4-chlorophenyl)cyclobutyl]-2-methylbutan-2-ol
1-Amino-1-[1-(4-chlorophenyl)cyclobutyl]-3-methylpentan-3-ol
1-Amino-1-[1-(4-chlorophenyl)cyclobutyl]pentan-3-ol
4-Amino-4-[1-(3-chlorophenyl)cyclobutyl]-2-methylbutan-2-ol
4-Amino-2-methyl-4-(1-phenylcyclobutyl)butan-2-ol
4-Amino-2-methyl-4-[1-(3-trifluoromethylphenyl)cyclobutyl]butan-2-ol
4-Amino-4-[1-(4-chlorophenyl)cyclobutyl]-2-trifluoromethylbutan-2-ol
4-Amino-4-[1-(4-fluorophenyl)cyclobutyl]-2-trifluoromethylbutan-2-ol
4-Amino-4-[1-(4-fluorophenyl)cyclobutyl]-2-methylbutan-2-ol
4-Amino-4-[1-(3-fluorophenyl)cyclobutyl]-2-methylbutan-2-ol
4-Amino-4-[1-(4-biphenylyl)cyclobutyl]-2-methylbutan-2-ol
4-Amino-2-methyl-4-[1-(4-methylthiophenyl)cyclobutyl]-butan-2-ol
1-Amino-3-methyl-1-(1-phenylcyclobutyl)pentan-3-ol
1-Amino-1-[1-(3-fluorophenyl)cyclobutyl]-3-methylpentan-3-ol
1-Amino-1-[1-(3-chlorophenyl)cyclobutyl]-3-methylpentan-3-ol
1-Amino-3-methyl-1-[1-(4-methylthiophenyl)cyclobutyl]-pentan-3-ol
1-Amino-1-[1-(4-fluorophenyl)cyclobutyl]-3-methylpentan-3-ol
1-Amino-3-ethyl-1-[1-(4-methoxyphenyl)cyclobutyl]-pentan-3-ol
1-Amino-3-ethyl-1-(1-phenylcyclobutyl)pentan-3-ol
1-Amino-5-ethoxy-1-[1-(4-fluorophenyl)cyclobutyl -3-methylpentan-3-ol
1-Amino-1-[1-(4-chlorophenyl)cyclobutyl]-5-methoxy-3-methylpentan-3-ol
4-Amino-4-[1-(4-chlorophenyl)cyclobutyl]-2-morpholinomethylbutan-2-ol
4-Amino-4-[1-(4-fluorophenyl)cyclobutyl]-2-morpholinomethylbutan-2-ol
1-Amino-1-[1-(4-chlorophenyl)cyclobutyl]-3-methoxymethylpentan-3-ol
4-Amino-4-[1-(4-methoxyphenyl)cyclobutyl]-2-methylbutan-2-ol
1-Amino-3-ethyl-1-[1-(4-fluorophenyl)cyclobutyl]-pentan-3-ol
1-Amino-[1-(4-biphenylyl)cyclobutyl]-3-ethylpentan-3-ol 1-Amino-1-[1-(3-chlorophenyl)cyclobutyl]-3-ethylpentan-3-ol
1-Amino-1-[1-(4-chlorophenyl)cyclobutyl]-3-methylhexan-3-ol
1-Amino-1-[1-(4-chlorophenyl)cyclobutyl]-3-ethyl-4-methylpentan-3-ol
1-Amino-1-[1-(4-chlorophenyl)cyclobutyl]-3,4,4-trimethylpentan-3-ol
1-Amino-1-[1-(4-chlorophenyl)cyclobutyl]-3,5-dimethylhexan-3-ol
4-Amino-4-[1-(4-chlorophenyl)cyclobutyl]-2-cyclopropylbutan-2-ol
4-Amino-4-[1-(4-chlorophenyl)cyclobutyl]-2-methoxymethylbutan-2-ol
4-Amino-4-[1-(4-fluorophenyl)cyclobutyl]-2-methoxymethylbutan-2-ol
1-Amino-1-[1-(4-chlorophenyl)cyclobutyl]-3-methoxymethylhexan-3-ol
1-Amino-5-methoxy-3-methyl-1-(1-phenylcyclobutyl)-pentan-3-ol
1-Amino-1-[1-(4-fluorophenyl)cyclobutyl]-5-methoxy-3-methylpentan-3-ol
1-Amino-1-[1-(4-chlorophenyl)cyclobutyl]-3-(2-methoxyethyl)pentan-3-ol
1-Amino-1-[1-(4-chlorophenyl)cyclobutyl]-5-ethoxy-3-methylpentan-3-ol
1-Amino-3-ethoxymethyl-1-[1-(4-fluorophenyl)cyclobutyl]pentan-3-ol
1-Amino-5-ethoxy-1-[1-(3-fluorophenyl)cyclobutyl]-3-methylpentan-3-ol
1-Amino-1-[1-(4-chlorophenyl)cyclobutyl]-3-ethoxymethylpentan-3-ol
1-Amino-1-[1-(4-chlorophenyl)cyclobutyl]-3-methyl-4-methylthiopentan-3-ol
4-[1-(4-Chlorophenyl)cyclobutyl]-4-dimethylamino-2-methylbutan-2-ol
4-Dimethylamino-4-(1-phenylcyclobutyl)-2-methylbutan-2-ol
1-Dimethylamino-3-ethyl-1-[1-(4-fluorophenyl)cyclobutyl]pentan-3-ol
4-Dimethylamino-4-[1-(4-fluorophenyl)cyclobutyl]-2-methylbutan-2-ol
1-Dimethylamino-1-[1-(4-fluorophenyl)cyclobutyl]-3-methylpentan-3-ol
1-[1-(4-Chlorophenyl)cyclobutyl]-1-dimethylamino-3-methylpentan-3-ol
1-[1-(4-Chlorophenyl)cyclobutyl)-1-dimethylamino-3-ethylpentan-3-ol
1-Amino-1-[1-(4-chlorophenyl)cyclobutyl]-3-ethylpentan-3-ol
4-Amino-4-[1-(4-chlorophenyl)cyclobutyl]-2,3-dimethylbutan-2-ol
4-Amino-4-[1-(3,4-dichlorophenyl)cyclobutyl]butan-1-ol
4-[1-(3,4-Dichlorophenyl)cyclobutyl]-4-dimethylaminobutan-1-ol
4-Amino-4-[1-(4-chlorophenyl)cyclobutyl]butan-1-ol
4-[1-(4-Chlorophenyl)cyclobutyl]-4-dimethylaminobutan-1-ol
5Amino-5-[1-(4-chlorophenyl)cyclobutyl]pentan-1-ol
5-[1-(4-Chlorophenyl)cyclobutyl]-5-dimethylaminopentan-1-ol
5-[1-(4-Chlorophenyl)cyclobutyl)-5-dimethylaminopentyl acetate
5-[1-(4-Chlorophenyl)cyclobutyl]-5-dimethylaminopentyl-2-methoxyacetate
7-Amino-7-[1-(3,4-dichlorophenyl)cyclobutyl]-heptan-1-ol
5-[1-(3,4-Dichlorophenyl)cyclobutyl]-5-dimethylaminopentane-1,2-diol
1-[1-(4-Chlorophenyl)cyclobutyl]-4-methoxybutylamine
1-[1-(4-Chlorophenyl)cyclobutyl]-4-ethoxybutylamine
1-[1-(4-Chlorophenyl)cyclobutyl]-4-propoxybutylamine
1-[1-(4-Chlorophenyl)cyclobutyl]-4-isopropoxybutylamine
1-[1-(4-Chlorophenyl)cyclobutyl]-4-methoxypentylamine
1-[1-(4-Chlorophenyl)cyclobutyl]-4-methoxy-3-methylbutylamine
1-[1-(4-chlorophenyl)cyclobutyl]-3-(methoxymethyl)pentylamine
1-[1-(3,4-Dichlorophenyl)cyclobutyl]-4-methoxybutylamine
4-Methoxy-1-[1-(4-tolyl)cyclobutyl]butylamine
4-Methoxy-1-[1-(3-trifluoromethylphenyl)cyclobutyl]-butylamine
4-Methoxy-1-[1-(2-naphthyl)cyclobutyl]butylamine
1-[1-(4-Bromophenyl)cyclobutyl]-4-methoxybutylamine
4-Propoxy-1-[1-(3-trifluoromethylphenyl)cyclobutyl]-butylamine
4-Isopropoxy-1-[1-(3-trifluoromethylphenyl)cyclobutyl]butylamine
1-[1-(3,4-Dichlorophenyl)cyclobutyl]-4-(1,1-dimethylpropoxy)butylamine
1-[1-(3,4-Dichlorophenyl)cyclobutyl]-4-hexyloxybutylamine
1-[1-(4-Chlorophenyl)cyclobutyl]-4-(2-methoxyethoxy)butylamine
1-[1-(3,4-Dichlorophenyl)cyclobutyl]-4-methoxypentylamine
1-[1-(3,4-Dichlorophenyl)cyclobutyl]-7-methoxyheptylamine
1-[1-(3,4-Dichlorophenyl)cyclobutyl]-4-(2-methoxyethoxy)butylamine
1-[1-(3,4-Dichlorophenyl)cyclobutyl]-4-cyclopentyloxybutylamine
1-[1-(3,4-Dichlorophenyl)cyclobutyl]-4-methylthiobutylamine
4-Methoxy-3-methyl-1-[1-(4-methylthiophenyl)cyclobutyl]butylamine
4-Methoxy-3-methyl-1-[1-(3-trifluoromethylphenyl)cyclobutyl]butylamine
4-(2-Cyclohexylethoxy)-1-[1-(3,4-dichlorophenyl)cyclobutyl]butylamine
N,N-Dimethyl-1-[1-(4-chlorophenyl)cyclobutyl]-1-methoxybutylamine
N,N-Dimethyl-1-[1-(4-chlorophenyl)cyclobutyl]-4-ethoxybutylamine
N,N-Dimethyl-1-[1-(4-chlorophenyl)cyclobutyl)-4-propoxybutylamine
N,N-Dimethyl-1-[1-(4-chlorophenyl)cyclobutyl]-4-isopropoxybutylamine
N,N-Dimethyl-1-[1-(4-chlorophenyl)cyclobutyl]-4-methoxypentylamine
N,N-Dimethyl-1-[1-(4-chlorophenyl)cyclobutyl]-4-methoxy-3-methylbutylamine
N,N-Dimethyl-1-[1-(4-chlorophenyl)cyclobutyl]-3-(methoxymethyl)pentylamine
N,N-Dimethyl-1-[1-(3,4-dichlorophenyl)cyclobutyl]-4-methoxybutylamine
N,N-Dimethyl-4-methoxy-1-[1-(3-trifluoromethylphenyl)-cyclobutyl]butylamine N,N-Dimethyl-1-[1-(4-bromophenyl)cyclobutyl]-4-methoxybutylamine N,N-Dimethyl-4-propoxy-1-{1-[3-(trifluoromethyl)-phenyl]cyclobutyl}butylamine N,N-Dimethyl-1-[1-(3,4-dichlorophenyl)cyclobutyl]-4-hexyloxybutylamine N,N-Dimethyl-1-[1-(3,4-Dichlorophenyl)cyclobutyl]-4-(2-methoxyethoxy)butylamine N,N-Dimethyl-1-[1-(3,4-dichlorophenyl)cyclobutyl]-4-methylthiobutylamine N,N-Dimethyl-4-isopropoxy-1-[1-(3-trifluoromethylphenyl)cyclobutyl]butylamine N,N-Dimethyl-4-methoxy-3-methyl-1-[1-(3-trifluoromethylphenyl)cyclobutyl]butylamine N,N-Dimethyl-1-[1-(4-chlorophenyl)cyclobutyl]-4-cyclopentyloxybutylamine N,N-Dimethyl-1-[1-(4-chlorophenyl)cyclobutyl]-5-methoxypentylamine N,N-Dimethyl-1-[1-(2-fluorophenyl)cyclobutyl]-4-methoxybutylamine N,N-Dimethyl-1-[1-(4-chlorophenyl)cyclobutyl]-4-octyloxybutylamine N,N-Dimethyl-1-[1-(3,4-dichlorophenyl)cyclobutyl]-4-octyloxybutylamine N,N-Dimethyl-1-[1-(3,4-dichlorophenyl)cyclobutyl]-9-methoxynonylamine N,N-Dimethyl-1-[1-(3,4-dichlorophenyl)cyclobutyl]-4-(1,1-dimethylpropoxy)butylamine N-Methyl-1-[1-(4-chlorophenyl)cyclobutyl]-4-ethoxybutylamine N-{1-[1-(3,4-Dichlorophenyl)cyclobutyl]-4-methoxybutyl}-pyrrolidine N-Methyl-1-[1-(4-chlorophenyl)cyclobutyl]-5-methoxypentylamine N-Methyl-1-[1-(4-chlorophenyl)cyclobutyl]-5-ethoxypentylamine N-Propyl-1-[1-(3,4-dichlorophenyl)cyclobutyl]-4-methoxybutylamine N-Isobutyl-1-[1-(3,4-dichlorophenyl)cyclobutyl]-4-methoxybutylamine N-(2-Methoxyethyl)-1-[1-(3,4-dichlorophenyl)cyclobutyl]-4-methoxybutylamine N-Benzyl-1-[1-(3,4-dichlorophenyl)cyclobutyl]-4-methoxybutylamine N-Cyclopropylmethyl-1-[1-(3,4-dichlorophenyl)cyclobutyl]-4-methoxybutylamine 1-[1-(4-Chlorophenyl)cyclobutyl]-2-methoxyethylamine N,N-Dimethyl-1-[1-(4-chlorophenyl)cyclobutyl]-2-methoxyethylamine N,(2-Morpholinoethyl)-1-[1-(4-chlorophenyl)cyclobutyl]-2-methoxyethylamine N-Methyl-N-(2-morpholinoethyl)-1-[1-(4-chlorophenyl)-cyclobutyl]-2-methoxyethylamine N,N-Dimethyl-1-[1-(4-chlorophenyl)cyclobutyl]-3-methoxypropylamine N,N-Dimethyl-1-[1-(4-chlorophenyl)cyclobutyl]-4-[2-(4-pyridyl)ethoxy]butylamine 2-{4-[1-(4-Chlorophenyl)cyclobutyl]-4-dimethylaminobutoxy}-N,N-3-oxapentamethyleneacetamide 1-{4-[1-(4-Chlorophenyl)cyclobutyl]-4-dimethylaminobutoxy}propan-2-one 1-{4-[1-(4-chlorophenyl)cyclobutyl]-4-dimethylaminobutoxy}propan-2-ol 2-{4-[1-(4-Chlorophenyl)cyclobutyl]-4-dimethylaminobutoxy},acetamide 1-[1-(4-Chlorophenyl)cyclobutyl)-2-methylthioethylamine N,N-Dimethyl-1-[1-(4-chlorophenyl)cyclobutyl]-2-methylthioethylamine N,N-Dimethyl-1-[1-(4-chlorophenyl)cyclobutyl]-4-methylsulphinylbutylamine 1-[1-(4-Chlorophenyl)cyclobutyl]-2-methylsulphonylethylamine 1-[1-(3,4-Dichlorophenyl)cyclobutyl]-2-methylsulphonylethylamine N,N-Dimethyl-1-[1-(4-chlorophenyl)cyclobutyl]-2-methylsulphonylethylamine N,N-Dimethyl-1-[1-(3,4-dichlorophenyl)cyclobutyl]-2-methylsulphonylethylamine and pharmaceutically acceptable salts thereof.

The present invention also includes pharmaceutical compositions containing a therapeutically effective amount of a compound of formula I together with a pharmaceutically acceptable diluent or carrier.

In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1-90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compositions are the excipients known in the pharmacists' art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means .and, if desired, provided with enteric coatings in a known manner. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example suppositories with cocoa butter or polyethylene glycol bases.

Compositions of the invention suitable for parenteral administration are the known pharmaceutical forms for such administration, for example sterile suspensions or sterile solutions in a suitable solvent.

Compositions for topical administration may comprise a matrix in which the pharmacologically active compounds of the present invention are dispersed so that the compounds are held in contact with the skin in order to administer the compounds transdermally. Alternatively the active compounds may be dispersed in a pharmaceutically acceptable cream or ointment base.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The pharmaceutical compositions containing a therapeutically effective amount of a compound of formula I may be used to treat depression in human beings. In such treatment the amount of the compound of formula I administered per day is in the range 1 to 1000 mg preferably 5 to 500 mg.

Processes for the preparation of compounds of formula I will now be described. These processes form a further aspect of the present invention.

Compounds of formula I may be prepared by the reduction of a compound of formula V

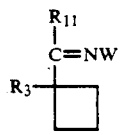

V in which $R_{11}$ is the group $R_4$ or a precursor thereto and W is H, —OH or an ester or ether thereof, a metal-containing moiety derived from an organometallic reagent giving a primary amine of formula I in which $R_1$ and $R_2$ are H, or W is the group $R_1$ when $R_1$ is other than H giving a secondary amine of formula I in which $R_2$ is H and, if necessary, the conversion of the group $R_{11}$ into the group $R_4$ as will be described hereinafter. Suitable reducing agents for the above reactions include sodium borohydride/ titanium (IV) chloride, sodium borohydride/molybdic acid, sodium cyanoborohydride, borane-dimethylsulphide complex and lithium aluminium hydride or the reduction may be performed by catalytic hydrogenation. When W is a metal-containing moiety it may be lithium derived from an organolithium compound, a halomagnesium group (for example MgCl, MgBr or MgI) derived from a Grignard reagent or a halozinc group (for example ZnBr) derived from an organozinc compound.

Compounds of formula I in which $R_1$ and $R_2$ are H may be prepared by the reduction of a compound of formula V in which W is a group of formula —$NR_{12}R_{13}$ in which $R_{12}$ and $R_{13}$ are not both H and are, for example, both methyl or $R_{12}$ is phenyl and $R_{13}$ is H, the reduction being performed for example by (a) catalytic hydrogenation or (b) by sodium borohydride to give the corresponding hydrazine which is subsequently converted into the amine by hydrogenolysis for example over a palladium catalyst, followed by conversion, if necessary of the group $R_{11}$ into the group $R_4$ as will be described hereinafter.

Compounds of formula I may be prepared by the reductive removal of the cyano group from a compound of formula VI

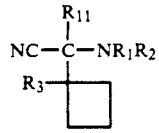

VI for example using sodium borohydride and then, if necessary the conversion of the group $R_{11}$ into the group $R_4$ as will be described hereinafter.

Compounds of formula I in which $R_4$ is a group of formula —$COR_{14}$ may be prepared by the thermal elimination of hydrogen cyanide from a compound of formula VI in which $R_{11}$ is a group of formula —CH(OH)$R_{15}$ in which $R_{15}$ is the group $R_{14}$ or a precursor thereto followed by, if necessary, the conversion of the group $R_{15}$ into the group $R_{14}$.

Compounds of formula I may be prepared by the displacement of the cyano group in an aminonitrile of formula VII

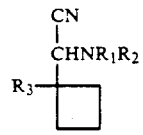

VII by reaction with an organometallic reagent of formula $MR_{11}$ in which M represents a metal containing moiety and then, if necessary, the conversion of the group $R_{11}$ into the group $R_4$ as will be described hereinafter. $MR_{11}$ may represent Grignard reagents in which M represents a halomagnesium group and (a) $R_{11}$ is the group $R_4$ and is substituted by an optionally substituted alkoxy or cycloalkyloxy group or a group of formula $S(O)_pR_5$, (b) $R_{11}$ is the group $R_4$ which is substituted by an optionally substituted alkylenedioxy group, (c) $R_{11}$ is a group substituted by a protected hydroxy group for example a halomagnesiumoxy group or an acetal such as 1-ethoxyethoxy, (d) $R_{11}$ is a group substituted by a protected oxo group, for example an acetal or a thioacetal group, (e) $R_{11}$ is a group geminally disubstituted by alkoxy or cycloalkyloxy groups or (f) $R_{11}$ is a group containing a carboxylic acid derivative such as a salt or an ester containing a of formula —$COOR_{19}$ in which $R_{19}$ is derived from a suitable alcohol.

Compounds of formula I in which $R_4$ is a group of formula —$COR_{16}$ may be prepared by the reaction of an aminonitrile of formula VII with an organolithium reagent of formula $R_{17}Li$ in which $R_{17}$ is the group $R_{16}$ or a precursor thereto followed by hydrolysis and, if necessary, the conversion of the group $R_{17}$ into the group $R_{16}$.

Compounds of formula I may be prepared by the reductive amination of a ketone of formula VIII

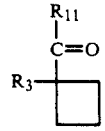

VIII in which the group $R_{11}$ is the group $R_4$ or a precursor thereto and does not contain an oxo or other group which is capable of undergoing reaction under the conditions used and then, if necessary the conversion of the group $R_{11}$ into the group $R_4$ as will be described hereinafter. Examples of suitable reductive amination processes are (a) for compounds of formula I in which $R_1$ and $R_2$ are H, by reaction of the ketone with an ammonium salt for example ammonium acetate and a reducing agent such as sodium cyanoborohydride, (b) for compounds of formula I in which $R_1$ is other than H and $R_2$ is H, by reaction of the ketone with an amine of formula $R_1NH_2$ and a reducing agent such as sodium cyanoborohydride or sodium borohydride, (c) for compounds of formula I in which neither $R_1$ nor $R_2$ is H, by reaction of the ketone with an amine of formula $R_1R_2NH$ and either formic acid or a reducing agent such as sodium cyanoborohydride, (d) by catalytic hydrogenation at elevated temperature and pressure of a mixture of the ketone and an amide of formula $R_1R_2NH$ or ammonia.

Compounds of formula I in which neither $R_1$ nor $R_2$ is H may be prepared by the reaction of a ketone of formula VIII with a formamide of formula $HCONR_1R_2$ for example in the presence of formic acid and then, if necessary the conversion of the group $R_{11}$ into the group $R_4$ as will be described hereinafter.

Compounds of formula I in which $R_2$ is H may be prepared by the reaction of an organometallic reagent of formula $MR_{11}$ with an amine of formula IX

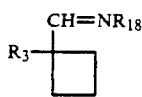    IX in which (a) $R_{18}$ has the meaning given above for $R_1$ but is not H, or (b) $R_{18}$ is an organometallic moiety for example a dialkylaluminium moiety such as a diisobutylaluminium moiety to give a primary amine in which $R_1$ and $R_2$ are H and then, if necessary the conversion of the group $R_{11}$ into the group $R_4$ as will be described hereinafter. $MR_{11}$ may represent organometallic compounds in which (a) M is lithium or a halomagnesium group and $R_{11}$ is the group $R_4$ and is substituted by an optionally substituted alkoxy or cycloalkyloxy group or a group of formula $S(O)_pR_5$, (b) M is lithium or a halomagnesium group and $R_{11}$ is the group $R_4$ which is substituted by an optionally substituted alkylenedioxy group, (c) M is lithium or a halomagnesium group and $R_{11}$ is a group substituted by a protected hydroxy group for example a halomagnesiumoxy group or an acetal such as 1-ethoxyethoxy, (d) M is lithium or a halomagnesium group and $R_{11}$ is a group substituted by a protected oxo group, for example, an acetal or thioacetal group, (e) M is lithium or a halomagnesium group and $R_{11}$ is a group geminally disubstituted by alkoxy or cycloalkoxy groups, (f) M is a lithium or a halomagnesium group and $R_{11}$ is a group containing a carboxylic acid derivative such as a salt or an ester containing a group of formula $—COOR_{19}$, (g) M is lithium and $R_{11}$ is an acyl anion equivalent for example an anion of formula X

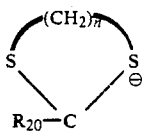    X in which n is 2 or 3, (h) M is a halozinc group for example a bromozinc group and $R_{11}$ is a group which contains, on the carbon atom carrying the halozinc group, a carboxylic ester group of formula $—COOR_{19}$.

Compounds of formula I in which $R_1$ is H may be prepared by hydrolysis for example acid hydrolysis of a compound of formula XI

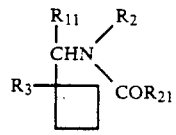    XI in which $R_{21}$ may be H or an optionally substituted hydrocarbon group.

Compounds of formula I in which $R_1$ is a group of formula $CH_2R_{21}$ may be prepared by reduction of a compound of formula XI for example by lithium aluminium hydride, sodium bis(2-methoxyethoxy)aluminium hydride or borane-dimethylsulphide complex.

Compounds of formula I in which $R_4$ is a group having two hydroxy substituents on adjacent carbon atoms of the hydrocarbon group may be prepared by the reaction of a compound of formula XII

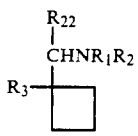    XII in which the group $R_{22}$ is an alkenyl group with for example osmium tetroxide.

Compounds of formula I in which the group $R_4$ contains a ketonic oxo substituent may be prepared by the oxidation, for example by thallium triacetate of a compound of formula XII in which $R_{22}$ is an alkenyl group or by the hydration, for example in the presence of mercuric ions or of thallium triacetate, of a compound of formula XII in which $R_{22}$ is an alkynyl group.

Compounds of formula I in which $R_4$ is a group containing two oxo substituents and having two carbon atoms between the carbon atoms carrying the oxo substituents may be prepared by the hydrolysis of a compound of formula XII in which $R_{22}$ is a group containing a 2,5-disubstituted furyl ring.

Compounds of formula I in which $R_4$ is a group containing a ketonic oxo group in which the oxo group is carried by a carbon atom other than the one adjacent the carbon atom carrying the group $NR_1R_2$ may be prepared by the reaction of an organometallic reagent such as a Grignard reagent or an organolithium compound with a compound of formula XII in which the group $R_{22}$ contains a nitrile substituent.

Compounds of formula I may be prepared by the reduction, for example by sodium cyanoborohydride, of enamines of formula XIII

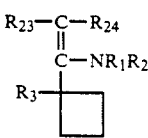    XIII in which $R_{24}$ is, for example, a group of formula $—COOR_{19}$ or a group of formula $SO_2Me$ to give compounds of formula XIV

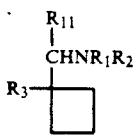

in which $R_{11}$ is a group of formula $CHR_{23}R_{24}$ followed by the conversion, if necessary, of the group $R_{11}$ into the group $R_4$.

In the processes described hereinbefore in which the group $R_{11}$ is converted into the group $R_4$ the following conversion processes may be used:

a) when $R_{11}$ contains a protected hydroxy group the protecting group is removed by processes well known in the art for example by hydrolysis when the protecting group is a halomagnesiumoxy or a 1-ethoxyethoxy group to give a compound of formula I in which $R_4$ contains a hydroxy substituent.

b) when $R_{11}$ contains a protected oxo group, the protecting group is removed by processes well known in the art for example by hydrolysis when the protecting group is an acetal or thioacetal to give a compound of formula I in which $R_4$ contains an oxo substituent.

c) when $R_{11}$ is a group geminally disubstituted by alkoxy or cycloalkyloxy groups, one of the alkoxy or cycloalkyloxy groups is removed reductively for example by reaction with lithium aluminium hydride and a Lewis acid such as aluminium chloride to give a compound of formula I in which $R_4$ contains an alkoxy or cycloalkyloxy substituent.

d) when $R_{11}$ contains a carboxylic acid derivative such as a salt or a carboxylic ester group of formula —$COOR_{19}$, the group $R_{11}$ is reduced (for example by lithium aluminium hydride) to give a compound of formula I in which $R_4$ contains a —$CH_2OH$ group e) when $R_{11}$ contains a carboxylic ester group of formula —$COOR_{19}$
  i) the carboxylic ester group is reacted with a Grignard reagent of formula $R_{25}MgX$ and triethylamine to give a compound of formula I in which $R_4$ contains a —$COR_{25}$ group,
  ii) the carboxylic ester group is reacted with an organometallic reagent for example a Grignard reagent of formula $R_{25}MgX$ and lithium borohydride to give a compound of formula I in which $R_4$ contains a —$CH(OH)R_{25}$ group, or
  iii) the carboxylic ester group is reacted with an organometallic reagent such as a Grignard reagent of formula $R_{25}MgX$ to give a compound of formula I in which $R_4$ contains a —$C(OH)(R_{25})_2$ group, f) when $R_{11}$ is derived from an acyl anion equivalent of formula X the group is hydrolysed to give a compound of formula I in which $R_4$ is a group of formula —$COR_{20}$. The reduction in (d) above may occur simultaneously with the reduction of compounds of formula V, the reductive removal of the cyano group from compounds of formula VI, the reductive amination of ketones of formula VIII or the reduction of compounds of formula XI.

Compounds of formula I may be prepared by the conversion of other compounds of formula I by methods well known in the art for converting ketones into alcohols or ethers, for converting alcohols into acylated derivatives thereof or into ketones and into ethers or thioethers, for converting ethers into alcohols or ketones, for converting compounds containing alkylthio groups into compounds containing alkylsulphinyl and alkylsulphonyl groups and for converting compounds containing alkylsulphinyl groups into compounds containing alkylsulphonyl and alkylthio groups.

Examples of suitable processes include the following:

a) reduction of a ketone for example by lithium aluminium hydride, sodium borohydride or boranedimethylsulphide complex to give a secondary alcohol.

b) reaction of a ketone with an organometallic reagent such as a Grignard reagent to give a tertiary alcohol.

c) reaction of a ketone with a 1,2-diol or a 1,3-diol in the presence of an acid catalyst such as p-toluenesulphonic acid to give a compound containing an alkylenedioxy substituent.

d) acylation of an alcohol for example by reaction with a carboxylic acid anhydride to give an acylated derivative.

e) alkylation or cycloalkylation of an alcohol for example by reaction with a base such as sodium hydride and then a compound of formula $R_{26}X$ in which $R_{26}$ is an alkyl or cycloalkyl group and X is a leaving group for example a tosyloxy group or bromo to give an ether.

f) conversion of the hydroxy group of an alcohol into a leaving group for example a tosyloxy group or bromo followed by the replacement of the leaving group by reaction with an alkali metal alkoxide, cycloalkyloxide, alkylsulphide or alkylsulphoxide to give an ether, a thioether or a sulphone.

g) oxidation of a secondary alcohol for example by chromic acid to give a ketone.

h) cleavage of an ether, for example, by trimethylsilyl iodide to give an alcohol.

i) hydrolysis of an alkylenedioxy compound to give a ketone.

j) by oxidation, for example, by m-chloroperbenzoic acid of alkylthio compounds to give alkylsulphinyl compounds.

k) by oxidation, for example, by hydrogen peroxide of an alkylthio or alkylsulphinyl compound to give an alkylsulphonyl compound.

l) by reduction for example by trimethylsilyl iodide of an alkylsulphinyl compound to give an alkylthio compound.

Compounds of formula I or precursors thereto in which one or both of $R_1$ and $R_2$ is other than H may be prepared from compounds of formula I or formula XIV in which one or both of $R_1$ and $R_2$ are H by appropriate methods which are well known in the art for the conversion of primary to secondary or tertiary amines or for the conversion of secondary to tertiary amines. Reactions involving the use of reducing agents may not be appropriate for compounds of formula I in which the group $R_4$ contains an oxo substituent. The following are given as examples of suitable processes:

a) alkylation of a primary amine for example by a process which includes the steps of protecting the primary amine with a protecting group such as trifluoroacetyl, alkylating with an alkyl halide and removing the protecting group for example by hydrolysis to give a secondary amine;

b) alkylation of a primary amine for example, with an alkyl halide to give a tertiary amine in which $R_1$ and $R_2$ are the same:

c) alkylation of a secondary amine for example with an alkyl halide to give a tertiary amine in which $R_1$ and $R_2$ may be different;

d) reaction of a primary amine with sodium borohydride and a carboxylic acid of formula $R_{27}COOH$ to give a secondary amine in which $R_2$ is a group of formula $-CH_2R_{27}$ and $R_1$ is H, or a tertiary amine in which both $R_1$ and $R_2$ are a group of formula $-CH_2R_{27}$.

e) reaction of a primary amine with formaldehyde and a reducing agent such as formic acid, sodium cyanoborohydride or sodium dihydrogen phosphite to give a tertiary amine in which both $R_1$ and $R_2$ are methyl;

f) reaction of a secondary amine in which $R_1$ is H with formaldehyde and a reducing agent such as formic acid, sodium cyanoborohydride or sodium dihydrogen phosphite to give a tertiary amine in which $R_1$ is methyl;

g) formylation of a primary amine for example by reaction with methyl formate, to give a compound of formula XI in which $R_{21}$ is H, followed by reduction, for example, with lithium aluminium hydride, sodium bis(2-methoxyethoxy)aluminium hydride or boranedimethylsulphide complex to give a secondary amine in which $R_1$ is methyl and $R_2$ is H;

h) formylation of a secondary amine in which $R_1$ is H, for example by reaction with methyl formate, to give a compound of formula XI in which $R_{21}$ is H followed by reduction for example with lithium aluminium hydride, sodium bis(2-methoxyethoxy)aluminium hydride or borane-dimethylsulphide complex to give a tertiary amine in which $R_1$ is methyl;

i) acylation of a primary amine for example by reaction with an acyl chloride of formula $R_{21}COCl$ or an anhydride of formula $(R_{21}CO)_2O$ and reducing the resulting compound of formula XI for example with lithium aluminium hydride, sodium bis(2-methoxyethoxy)aluminium hydride or borane-dimethylsulphide complex to give a secondary amine in which $R_1$ is $-CH_2R_{21}$ and $R_2$ is H;

j) acylation of a secondary amine in which $R_1$ is H, for example by reaction with an acyl chloride of formula $R_{21}COCl$ or an anhydride of formula $(R_{21}CO)_2O$ and reducing the resulting compound of formula XI for example with lithium aluminium hydride, sodium bis(2-methoxyethoxy)aluminium hydride or boranedimethylsulphide complex to give a tertiary amine in which $R_1$ is $-CH_2R_{21}$;

k) reaction of a primary amine with an aldehyde of formula $R_{28}CHO$ and reducing the resulting imine for example with sodium cyanoborohydride or sodium borohydride or by catalytic hydrogenation to give a secondary amine in which $R_1$ is $-CH_2R_{28}$ and $R_2$ is H;

l) reaction of a primary amine with a ketone of formula $R_{29}COR_{30}$ in which $R_{29}$ and $R_{30}$ may be the same or different or $R_{29}$ and $R_{30}$ together with the carbon atom to which they are attached form an alicyclic ring and reducing the resulting imine for example with sodium cyanoborohydride or sodium borohydride or by catalytic hydrogenation to give a secondary amine in which $R_1$ is a group of formula $-CHR_{29}R_{30}$ and $R_2$ is H.

m) reaction of a secondary amine in which $R_1$ is H with an aldehyde of formula $R_{28}CHO$ in which the group $R_{28}$ has a hydrogen atom on the carbon atom adjacent the formyl group, and reducing the resulting enamine for example with sodium cyanoborohydride or formic acid or by catalytic hydrogenation to give a tertiary amine in which $R_1$ is $-CH_2R_{28}$;

n) reaction of a secondary amine in which $R_1$ is H with a ketone of formula $R_{29}COR_{30}$ in which at least one of the groups $R_{29}$ and $R_{30}$ has a hydrogen atom on the carbon atom adjacent the carbonyl group and reducing the resulting enamine for example with sodium cyanoborohydride or formic acid or by catalytic hydrogenation to give a tertiary amine in which $R_1$ is a group of formula $-CHR_{29}R_{30}$.

o) reaction of a primary amine with a compound having two leaving groups for example tosyloxy or halo, preferably bromo and in which the carbon atoms carrying the leaving groups are separated by a) an optionally substituted ethylene or trimethylene group, for example the compound is 1,4-dibromobutane or 1,5-dibromopentane, to give a compound in which $R_1$ and $R_2$ together with the nitrogen atom to which they are attached form an optionally substituted pyrrolidinyl or piperidino ring, (b) an optionally substituted 2-oxatrimethylene group, for example the compound is bis(2-bromoethyl)ether, to give a compound in which $R_1$ and $R_2$ together with the nitrogen atom to which they are attached form an optionally substituted morpholino ring or (c) an optionally substituted 2-azatrimethylene group, for example the compound is bis(2-bromoethyl)amine or N-methylbis(2-bromoethyl)amine, to give a compound in which $R_1$ and $R_2$ together with the nitrogen atom to which they are attached form an optionally substituted piperazinyl ring.

Compounds of formula V in which W=H may be prepared by the hydrolysis of a compound of formula V in which W is a metal-containing moiety or by the selective reduction of a compound of formula V in which W is OH or an ester or ether thereof. Compounds of formula V in which W=H may be prepared by the reaction of a ketone of formula VIII with ammonia.

Compounds of formula V in which W is OH or an ester or ether thereof or a group of formula $-NR_{12}R_{13}$ may be prepared by the reaction of a ketone of formula VIII with hydroxylamine or an ester or ether thereof or a hydrazine of formula $H_2NNR_{12}R_{13}$ respectively.

Compounds of formula V in which W is a metal-containing moiety may be prepared by the reaction of an organometallic reagent of formula $MR_{11}$ with a carbonitrile of formula XV

In these reactions $MR_{11}$ represents an organometallic compound in which (a) M is lithium or a halomagnesium group and $R_{11}$ is the group $R_4$ and is substituted by an optionally substituted alkoxy or cycloalkyloxy group or a group of formula $S(O)_pR_5$, (b) M is lithium or a halomagnesium group and $R_{11}$ is the group $R_4$ which is substituted by an optionally substituted alkylenedioxy group, (c) M is lithium or a halomagnesium group and $R_{11}$ is a group substituted by a protected hydroxy group for example a halomagnesiumoxy group, or an acetal such as 1-ethoxyethoxy, (d) M is lithium or a halomagnesium group and $R_{11}$ is a group substituted by a protected oxo group for example, an acetal or thioacetal group, (e) M is lithium or a halomagnesium group and $R_{11}$ is a group geminally disubstituted by alkoxy or cycloalkyloxy groups, (f) M is a lithium or a halomagnesium group and $R_{11}$ is a group containing a carboxylic acid derivative such as a salt or an ester containing a group of formula $-COOR_{19}$, (g) M is a lithium atom and $R_{11}$ is an acyl anion equivalent for example an anion of formula X or (h) M is a halozinc group for example a bromozinc group and $R_{11}$ is a group which contains, on the carbon atom carrying the halozinc group, a carboxylic ester group of formula —COOR$_{19}$.

Compounds of formula V in which R$_{11}$ is a group of formula XVI

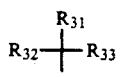   XVI may, be prepared by the reaction of a base such as butyllithium with a compound of formula XVII

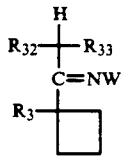   XVII in which W is OH or an ester or ether thereof or a group of formula —NR$_{12}$R$_{13}$ followed by reaction with (a) a compound of formula R$_{31}$X in which R$_{31}$ is a group substituted by an optionally substituted alkoxy or cycloalkyloxy group, a protected hydroxy group, a protected oxo group, an ester group or a group of formula S(O)$_p$R$_5$ and X is a leaving group such as a tosyloxy group or halo for example bromo, (b) a ketone of formula R$_{34}$COR$_{35}$ to give a compound of formula V in which R$_{11}$ is a group of formula XVI in which R$_{31}$ is a group of formula C(OH)R$_{34}$R$_{35}$, (c) an aldehyde of formula R$_{36}$CHO to give a compound of formula V in which R$_{11}$ is a group of formula XVI in which R$_{31}$ is a group of formula CH(OH)R$_{36}$, (d) an unsaturated ester of formula CH$_2$=CHCOOR$_{37}$ in which R$_{37}$ is derived from any appropriate alcohol to give, a compound of formula V in which R$_{11}$ is a group of formula XVI in which R$_{31}$ is a group of formula —CH$_2$CH$_2$COOR$_{37}$ and (e) a derivative of a carboxylic acid such as an acid chloride of formula R$_{38}$COCl or an ester of formula R$_{38}$COOR$_{39}$) in which R$_{39}$ is derived from any suitable alcohol to give a compound of formula V in which R$_{11}$ is a group of formula XVI in which R$_{31}$ is a group of formula —COR$_{38}$.

Compounds of formula V in which W is the group R$_1$ (but not H) may be prepared by the reaction of a ketone of formula VIII with an amine of formula R$_1$NH$_2$.

Compounds of formula VI may be prepared by the reaction of a base such as lithium diisopropylamide with a compound of formula VII, followed by reaction with (a) a compound of formula R$_{11}$X in which R$_{11}$ is a group containing an optionally substituted alkoxy or cycloalkyloxy group, a protected hydroxy group, a protected oxo group, an ester group or a group of formula S(O)$_p$R$_5$ and X is a leaving group such as tosyloxy or halo for example bromo, (b) an epoxide to give a compound of formula VI in which the group R$_{11}$ contains a hydroxy group separated from the carbon atom carrying the group —NR$_1$R$_2$ by two carbon atoms, (c) an aldehyde of formula R$_{40}$CHO or a ketone of formula R$_{41}$COR$_{42}$ to give compounds of formula VI in which R$_{11}$ is a group of formula —CH(OH)R$_{40}$ or a group of formula —CR$_{41}$R$_{42}$OH respectively or (d) a derivative of a carboxylic acid such as an acid chloride of formula R$_{43}$COCl or an ester of formula R$_{43}$COOR$_{44}$ in which R$_{44}$ is derived from a suitable alcohol to give a compound of formula VI in which R$_{11}$ is a group of formula —COR$_{43}$.

Compounds of formula VI in which R$_{11}$ is a group of formula —CH(OH)R$_{15}$ may be prepared by the reaction of a base such as lithium diisopropylamide with a compound of formula VII followed by reaction with an aldehyde of formula R$_{15}$CHO.

Aminonitriles of formula VII may be prepared by the reaction of an aldehyde of formula XVIII

   XVIII with an alkali metal cyanide (for example sodium cyanide) and a salt of an amine of formula R$_1$R$_2$NH or an ammonium salt. Aminonitriles of formula VII may also be prepared by the reaction of a cyanohydrin (formed by the reaction of an aldehyde of formula XVIII with an alkali metal cyanide) with an amine of formula R$_1$R$_2$NH. Aminonitriles of formula VII in which R$_1$ and R$_2$ are H may be prepared by the reaction of an imine of formula IX in which R$_{18}$ is an organometallic group, for example a dialkylaluminium moiety with an alkali metal cyanide followed by hydrolysis.

Ketones of formula VIII may be prepared by the hydrolysis for example acid hydrolysis of compounds of formula V in which W is H, —OH or an ester or ether thereof, a metal-containing moiety or a group of formula —NR$_{12}$R$_{13}$.

Ketones of formula VIII may be prepared by the reaction of carboxylic acid derivatives such as amides or acid halides with an organometallic reagent of formula R$_{11}$M for example by the reaction of an acid chloride of formula XIX

   XIX with a Grignard reagent of formula R$_{11}$MgX where X is Cl, Br or I at low temperatures for example —60° C. or by the reaction of a carboxylic acid of formula XX

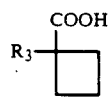   XX with an organolithium compound of formula R$_{11}$Li.

Ketones of formula VIII may be prepared by the hydrolysis of compounds of formula VI.

Ketones of formula VIII in which R$_{11}$ is a group of formula XXI

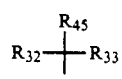   XXI in which R$_{45}$ is an alkoxy or cycloalkyloxy group may be prepared by the hydrolysis of compounds of formula XXII

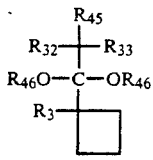

XXII in which $R_{46}$ represents, for example, methyl. Ketones of formula VIII in which $R_{11}$ is a group of formula XXI in which $R_{45}$ is an alkoxy or cycloalkyloxy group may be prepared by replacement of bromo in a bromoketone of formula XXIII

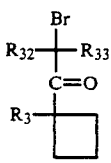

XXIII by reaction with an alkali metal alkoxide or cycloalkyloxide.

Imines of formula IX in which $R_{18}$ is $R_1$ may be prepared by reaction of an amine of formula $R_1NH_2$ with an aldehyde of formula XVIII. Imines of formula IX in which $R_{18}$ is a dialkylaluminium moiety may be prepared by the reaction of a carbonitrile of formula XV with a dialkylaluminium hydride such as diisobutylaluminium hydride.

Compounds of formula XI in which $R_{21}$ is H may be prepared by the reductive amidation of a ketone of formula VIII in which $R_{11}$ does not contain an oxo substituent for example, with formamide and formic acid or with ammonium formate and formic acid or with a formamide of formula $HCONHR_2$ and formic acid or with an amine of formula $R_2NH_2$ and formic acid. Compounds of formula XI may be prepared by the formylation or acylation of the corresponding primary or secondary amine for example by reaction with methyl formate or an acyl halide. Compounds of formula XI in which $R_2$ is other than H may be prepared by reacting a compound of formula XI in which $R_2$ is H with a compound of formula $R_2X$ where X is a leaving group such as halo in the presence of a base (for example sodium hydride).

Compounds of formula XII in which $R_{22}$ is an alkenyl or alkynyl group may be prepared by methods described in British Patent Application 2098602. Compounds of formula XII in which $R_{22}$ is a group containing a 2,5-disubstituted furyl ring may be prepared by the reduction of the imine formed by the reaction of a carbonitrile of formula XV with a Grignard reagent or organolithium reagent of formula $R_{22}M$.

Compounds of formula XIII in which $R_{24}$ is a group of formula $-COOR_{19}$ may be prepared by the reaction of a carbonitrile of formula XV with an organo halozinc compound for example a organo bromo zinc compound of formula $BrZnCHR_{23}R_{24}$. Compounds of formula XIII in which $R_{23}$ is H and $R_{24}$ is $SO_2Me$ may be prepared by the reaction of a carbonitrile of formula XV with methylsulphonylmethyllithium.

The preparation of carbonitriles of formula XV is described in British Patent Specification 2098602.

Compounds of formula XVII in which W is H may be prepared by the hydrolysis of a compound of formula XVII in which W is a metal-containing moiety or by the selective reduction of a compound of formula XVII in which W is OH or an ester or ether thereof. Compounds of formula XVII in which W is OH or an ester or ether thereof or a group of formula $-NR_{12}R_{13}$ may be prepared by the reaction of a ketone of formula XXIV

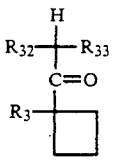

XXIV with hydroxylamine or an ester or ether thereof or a hydrazine of formula $H_2NNR_{12}R_{13}$ respectively. Compounds of formula XVII in which W is a metal-containing moiety may be prepared by the reaction of an organometallic reagent of formula $MCHR_{31}R_{32}$ in which M is lithium or halomagnesium with a carbonitrile of formula XV in a similar manner to that already described in respect of compounds of formula V. Compounds of formula XVII in which W is the group $R_1$ (but not H) may be prepared by the reaction of a ketone of formula XXIV with an amine of formula $R_1NH_2$.

The preparation of aldehydes of formula XVIII, of acid chlorides of formula XIX and of carboxylic acids of formula XX has been described in British Patent Specification 2098602.

Compounds of formula XXII in which $R_{45}$ is an alkoxy or cycloalkyloxy group may be prepared by the alkylation or cycloalkylation of a compound of formula XXII in which $R_{45}$ is hydroxy. Compounds of formula XXII in which $R_{45}$ is hydroxy and $R_{46}$ is methyl may be prepared by the reaction of a bromo ketone of formula XXIII with sodium methoxide in methanol.

Bromoketones of formula XXIII may be prepared by the bromination of ketones of formula XXIV which may be prepared by methods described in British Patent Specification 2098602 or in a similar manner to that described hereinbefore with respect to the ketones of formula VIII.

Compounds of formula I in which $R_4$ is a group of formula II in which $R_6$ is H may advantageously be prepared by the reduction of a compound of formula I in which $R_4$ is a group of formula $-COR_7$. Suitable reducing agents include sodium borohydride or borane-dimethylsulphide complex.

Compounds of formula I in which $R_4$ is a group of formula III, may advantageously be prepared by the reduction of a compound of formula V in which W is OH and $R_{11}$ is a group of formula III. Suitable reducing agents include lithium aluminium hydride, sodium borohydride/titanium (IV) chloride or sodium borohydride/molybdic acid. The compound of formula V in which W is OH may be prepared by the reaction of a compound of formula XVII in which $R_{32}$ and $R_{33}$ are H and W is OH with a base such as butyllithium followed by reaction with a ketone of formula $R_8COR_9$. The compounds of formula XVII in which $R_{32}$ and $R_{33}$ are H and W is OH may be prepared by the reaction of hydroxylamine with a ketone of formula XXIV in which $R_{32}$ and $R_{33}$ are H with hydroxylamine.

Compounds of formula I in which the group $R_4$ comprises an aliphatic group substituted by an alkoxy or cycloalkyloxy group may advantageously be prepared by the reduction of a compound of formula V in which W is lithium or a halomagnesium group of formula MgBr or MgCl and $R_{11}$ is the group $R_4$. Suitable reducing agents include sodium borohydride and lithium aluminium hydride. The compounds of formula V in which W is lithium may be prepared by the reaction of an organolithium reagent of formula $R_4Li$ with a carbonitrile of formula XV. The compounds of formula V in which W is a halomagnesium group may be prepared by the reaction of Grignard reagent of formula $R_4MgX$ with a carbonitrile of formula XV.

Compounds of formula I in which $R_4$ is a group of formula IV may advantageously be prepared by the reaction of an aminonitrile of formula VII with an organolithium compound of formula $LiR_{10}$ followed by hydrolysis.

Compounds of formula V, compounds of formula VI, ketones of formula VIII, the compounds of formula XI compounds of formula XIII and compounds of formula XXII which are described herein as intermediates are novel compounds and such novel intermediates form a further aspect of the present invention.

The therapeutic activity of the compounds of formula I has been indicated by assessing the ability of the compounds to reverse the hypothermic effects of reserpine in the following manner. Male mice of the Charles River CD1 strain weighing between 18 and 30 grammes were separated into groups of five and were supplied with food and water ad libitum. After five hours the body temperature of each mouse was taken orally and the mice were injected intraperitoneally with reserpine (5 mg/kg) in solution in deionised water containing ascorbic acid (50 mg/ml). The amount of liquid injected was 10 ml/kg of body weight. Nine hours after the start of the test food was withdrawn but water was still available ad libitum. Twenty-four hours after the start of the test the temperatures of the mice were taken and the mice were given the test compound orally at a dose volume of 10 ml/kg of body weight. The compound is administered in one of the following ways: (a) in aqueous solution, (b) in solution in less than 1% v/v acetic acid, (c) in solution in less than 0.02N hydrochloric acid, (d) suspended in an acacia suspension containing 100 mg acacia in 5 ml deionised water or (e) suspended in a 0.25% solution of hydroxy ethyl cellulose (sold under the trade name Cellosize QP 15000 by Union Carbide) in deionised water. Three hours later the temperatures of all the mice were again taken. The percentage reversal of the reserpine-induced loss of body temperature was then calculated by the formula:

$$\frac{(\text{Temperature after 27 hrs} - \text{Temperature after 24 hrs})}{(\text{Temperature after 5 hrs} - \text{Temperature after 24 hrs})} \times 100$$

The mean value for each group of five mice was taken. All the compounds which are the final products of the Examples hereinafter gave at least a 50% reversal when tested at 30 mg/kg. It is widely understood by those skilled in the art that this test is indicative of compounds having antidepressant activity in humans.

The invention will now be illustrated by the following Examples which are given by way of example only. All compounds were characterised by conventional analytical techniques and gave satisfactory elemental analyses. All melting and boiling points are expressed in degrees Celsius. Examples A to C describe the preparation of compounds of formula VII used in the preparation of compounds of formula I. In the description that follows the term "flash chromatography" is used to describe the purification technique described by Still et al [J. Org. Chem, 43 2923-5 (1978)]. In this technique a silica column is used and the eluant is as described in the relevant Example.

EXAMPLE A

A 1M solution of diisobutylaluminium hydride in hexane (100 ml) was added dropwise to a stirred solution of 1-(4-chlorophenyl)cyclobutanecarbonitrile (19.1 g) in dry ether (50 ml) at −30° C. under nitrogen. The mixture was allowed to warm to 0° C. and was kept at that temperature for 30 minutes. The mixture was cooled to −30° C. and 5N hydrochloric acid (100 ml) was added dropwise with stirring. The mixture was filtered to separate a solid and the filtrate was extracted with ether. The solid was added to the ether extracts which were washed with water and dried. Removal of the solvent gave 1-(4-chlorophenyl)cyclobutanecarbaldehyde as a yellow oil.

A mixture of 1-(4-chlorophenyl)cyclobutanecarbaldehyde (13.7 g), dry dimethylamine hydrochloride (6.6 g) and dry dimethylsulphoxide (50 ml) was added dropwise to a stirred mixture of sodium cyanide (3.9 g) in dry dimethylsulphoxide (100 ml). The mixture was stirred for 66 hours at ambient temperature and the reaction mixture was poured into water. The mixture was extracted with ether and the ether solution was then extracted with dilute hydrochloric acid. The aqueous phase was basified and extracted with ether. Removal of the ether gave 2-[1-(4-chlorophenyl)cyclobutyl]-2-dimethylaminoacetonitrile (m.p. 90°–91° C.).

In a similar manner to that described in EXAMPLE A above the compounds of formula VII (in which both $R_1$ and $R_2$ are methyl) listed in Table I were prepared.

TABLE I

| | $R_3$ | | Notes |
|---|---|---|---|
| A(a) | 4-bromophenyl | mp 94–96° C. | (2)(5) |
| A(b) | 2-fluorophenyl | mp 48–50° C. | (2) |
| A(c) | 3,4-dichlorophenyl | mp 67–69° C. | |
| A(d) | 4-biphenylyl | mp 100–103° C. | |
| A(e) | 4-methoxyphenyl | | (1) |
| A(f) | phenyl | bp 134°/0.8 mm | (3) |
| A(g) | 4-methylphenyl | | (1) |
| A(h) | 3-trifluoromethylphenyl | | (1) |
| A(i) | 2-naphthyl | mp 78–81° C. | (4) |
| A(j) | 3-chloro-5-methylphenyl | mp 112–115° C. | |
| A(k) | 3,5-dichloro-4-methoxyphenyl | mp 103–107° C. | |
| A(l) | 4-methylthiophenyl | mp 68–72° C. | |

Notes to Table I
(1) The product was an oil the boiling point of which was not determined.
(2) The back extraction into acid and the subsequent basification and ether extraction were not performed.
(3) The product was obtained in the form of its hydrochloride monohydrate which was converted into the free base and purified by distillation.
(4) The reaction mixture was extracted with dichloromethane and the product was an oil which was triturated with petroleum ether (b.p. 60–80° C.) to give a solid.
(5) The product was recrystallised from petroleum ether (b.p. 40–60° C.).

EXAMPLE B

A solution of sodium cyanide (19.5 g) in water (50 ml) was added dropwise over a period of 30 minutes to a solution of 1-(3,4-dichlorophenyl)cyclobutanecarbaldehyde [(62.16 g) prepared in a similar manner to that described in Example A for 1-(4-chlorophenyl)-cyclobutanecarbaldehyde] in methanol (70 ml) whilst the temperature was maintained at 20° C. by cooling. A saturated aqueous solution of sodium metabisulphite (81 ml) was added over a period of 20 minutes at 20° C. and the mixture was stirred for 16 hours and then poured into a mixture of ice and water. The resulting mixture was extracted with ether and the extracts were washed and dried. Evaporation of the solvent gave 2-[1-(3,4-dichlorophenyl)cyclobutyl]-2-hydroxyacetonitrile as a yellow oil which was used without further purification.

4-Methylpiperidine (4.8 g) was added to a solution of 2-[1-(3,4-dichlorophenyl)cyclobutyl]-2-hydroxyacetonitrile (12 g) in toluene (50 ml). The reaction mixture was stirred and heated at 100°-105° C. for two hours, cooled and diluted with water (100 ml) and ether (60 ml). The organic layer was separated washed with water and dried. Evaporation of the solvents gave an oil which solidified on standing to give a solid which was triturated with petroleum ether (b.p. 60°-80° C.) to give 2-[1-(3,4-dichlorophenyl)cyclobutyl]-2-(4-methylpiperidino)acetonitrile (m.p. 76°-78° C.).

In a similar manner to that described above the compounds of formula VII [in which $R_3$ is 3,4-dicholorophenyl for Examples B(a) to B(h), 4-chlorophenyl for Example (B(i) and 3-trifluoromethylphenyl for Example B(j)] listed in Table II were prepared.

TABLE II

| | $NR_1R_2$ | | Notes |
|---|---|---|---|
| B(a) | morpholino | mp 76-78° C. | (1) |
| B(b) | N(Me)Bu | | (1)(2) |
| B(c) | NHBu$^t$ | mp 63-65° C. | (1)(3) |
| B(d) | N(Me)(2-morpholinoethyl) | mp 88-90° C. | |
| B(e) | N(Me)(2-hydroxyethyl) | mp 78-81° C. | (4) |
| B(f) | 1,2,3,6-tetrahydro-1-pyridyl | mp 78-80° C. | (5) |
| B(g) | N(Me)cyclohexyl | | (2)(5) |
| B(h) | piperidino | | (2) |
| B(i) | NEt$_2$ | mp 45-51° C. | (6) |
| B(j) | N(Me)(2-morpholinoethyl) | | (2)(7) |

Notes to Table II
(1) An excess of the amine of formula $R_1R_2NH$ and the 2-hydroxyaceto- nitrile were heated together with no solvent present.
(2) The product was an oil the boiling point of which was not determined.
(3) After the amine of formula $R_1R_2NH$ and the 2-hydroxyacetonitrile had been heated for 4 hours, excess amine was removed by evaporation and the crude product converted into a hydrochloride salt. Basification of the salt gave the free base which was extracted with ether.
(4) The amine of formula $R_1R_2NH$ and the 2-hydroxyacetonitrile were dissolved in ether and the solution heated to 40° C. for 30 minutes. The ether was removed by distillation and the residue heated at 90-95° C. for 1½ hours.
(5) The amine of formula $R_1R_2NH$ and the 2-hydroxyacetonitrile were dissolved in dichloromethane and heated with stirring at 90-95° C. for 2 hours.
(6) An excess of the amine of formula $R_1R_2NH$ and the 2-hydroxyacetonitrile dissolved in toluene containing $MgSO_4$ and heated at 45° C. for 5 days.
(7) The amine of formula $R_1R_2NH$ and the 2-hydroxyacetonitrile were heated in toluene at 110° C. for 1 hour.

EXAMPLES 1 TO 44

The compounds of formula I in which $R_4$ is a group of formula IV (listed in Table III) have been prepared from aminonitriles of formula VII by the following general reaction scheme.

A solution of an organolithium compound of formula $LiR_{10}$ in a solvent A (1=ether, 2×hexane, 3=pentane) is added dropwise at ambient temperature under nitrogen or argon to a solution of the aminonitrile prepared as described in the Example listed in the column headed SM in solvent B (1=toluene, 2=ether, 3=pentane/toluene). The mixture was then stirred for a period of C hours, and the resulting intermediate was hydrolysed by aqueous hydrochloric acid. The desired product was isolated from the reaction mixture and purified as indicated by the notes in the column headed PM which have the following meanings:

(1) by distillation—the boiling range of the product given in the last column
(2) by distillation in a Buchi Kugelrohr apparatus—the operating temperature is given in the last column
(3) by high performance liquid chromatography—the boiling point of the product was not determined
(4) by hydrochloride salt formation—the melting point of the salt is given in the last column
4(a) by hydrochloride salt formation to give a hygroscopic solid the melting point of which could not be determined.
(5) by maleate salt formation—the melting point of the salt is given in the last column
(6) by oxalate salt formation—the melting point of the salt is given in the last column
(7) by maleate salt formation to give a gum followed by flash chromatography using 80:20 mixture of petroleum ether (b.p. 40°-60° C.) and ether (7a) or using 87.5:12.5 mixture of petroleum ether (b.p. 40°-60° C.) and ether (7b) to give an oil—the boiling point of the product was not determined
(8) the free base was obtained as a solid—the melting point is given in the last column
(9) the product was isolated as an oil which was not purified further—the boiling point was not determined
(10) by flash chromatography using ethyl acetate (10a), a 95:5 mixture of petroleum ether (bp 40°-60° C.) and ether (10b) or a 90:10 mixture of petroleum ether (bp 40°-60° C.) and ether (10c), as eluant—the boiling point of the product was not determined.
(11) by distillation in a Buchi Kugelrohr apparatus (190° C./0.5 mm Hg) followed by maleate salt formation and then high performance liquid chromatography to give an oil—the boiling point was not determined.

TABLE III

| Ex. | SM | $R_{10}$ | $R_3$ | $NR_1R_2$ | A | B | C | PM | m.p./b.p. |
|---|---|---|---|---|---|---|---|---|---|
| 1 | A(c) | Me | 3,4-dichlorophenyl | NMe$_2$ | 1 | 1 | 0.5 | 3 | |
| 2 | A(f) | Me | phenyl | NMe$_2$ | 1 | 1 | 1 | 9 | |
| 3 | A(a) | Et | 4-bromophenyl | NMe$_2$ | 1 | 1 | 2 | 8 | 53-54° C. |
| 4 | A(j) | Et | 3-chloro-5-methylphenyl | NMe$_2$ | 1 | 1 | 18 | 4 | 178-182° C. |
| 5 | A(k) | Et | 3,5-dichloro-4-methoxy-phenyl | NMe$_2$ | 1 | 1 | 18 | 4 | 201-203° C. |
| 6 | A(e) | Et | 4-methoxyphenyl | NMe$_2$ | 1 | 1 | 18 | 10a | |
| 7 | A(d) | Et | 4-biphenylyl | NMe$_2$ | 1 | 1 | 16 | 4 | 71-75° C. |
| 8 | A(h) | Et | 3-trifluoro-methylphenyl | NMe$_2$ | 1 | 1 | 16 | 2 | 160° C./0.4 mm Hg |
| 9 | A(i) | Et | 2-naphthyl | NMe$_2$ | 1 | 1 | 6 | 4 | 215° C. |
| 10 | A(l) | Et | 4-methylthiophenyl | NMe$_2$ | 1 | 1 | 18 | 4a | |
| 11 | A | Pr | 4-chlorophenyl | NMe$_2$ | 1 | 1 | 1 | 2 | 120° C./0.25 mm Hg |
| 12 | A(i) | Pr | 2-naphthyl | NMe$_2$ | 1 | 1 | 1 | 4 | 208-210° C. (dec) |
| 13 | A(h) | Pr | 3-trifluoromethylphenyl | NMe$_2$ | 1 | 1 | 1.5 | 4 | 110-115° C. |
| 14 | A(b) | Pr | 2-fluorophenyl | NMe$_2$ | 1 | 1 | 1 | 4 | 168-169° C. |
| 15 | A(e) | Pr | 4-methoxyphenyl | NMe$_2$ | 1 | 1 | 72 | 1 | 143-146° C./0.5 mm Hg |

TABLE III-continued

| Ex. | SM | R₁₀ | R₃ | NR₁R₂ | A | B | C | PM | m.p./b.p. |
|---|---|---|---|---|---|---|---|---|---|
| 16 | A(g) | Pr | 4-methylphenyl | NMe₂ | 1 | 1 | 18 | 6 | 96–105° C. |
| 17 | A(d) | Pr | 4-biphenylyl | NMe₂ | 1 | 1 | 1 | 5 | 138–140° C. |
| 18 | A(f) | Pr | phenyl | NMe₂ | 1 | 1 | 1 | 4 | 157–158° C. |
| 19 | A | Bu | 4-chlorophenyl | NMe₂ | 2 | 1 | 72 | 11 | |
| 20 | A(c) | Bu | 3,4-dichlorophenyl | NMe₂ | 2 | 1 | 0.5 | 2 | 170° C./0.3 mm Hg |
| 21 | A(c) | Buⁱ | 3,4-dichlorophenyl | NMe₂ | 1 | 1 | 3 | 4 | 75–80° C. |
| 22 | A(c) | isopentyl | 3,4-dichlorophenyl | NMe₂ | 3 | 1 | 3 | 4 | 163–169° C. |
| 23 | A(c) | 4-pentenyl | 3,4-dichlorophenyl | NMe₂ | 1 | 1 | 0.5 | 10b | |
| 24 | A(f) | 4-pentenyl | phenyl | NMe₂ | 1 | 1 | 1.5 | 7a | |
| 25 | A | 4-pentenyl | 4-chlorophenyl | NMe₂ | 1 | 1 | 18 | 7b | |
| 26 | A(c) | hexyl | 3,4-dichlorophenyl | NMe₂ | 1 | 1 | 0.5 | 10c | |
| 27 | A | hexyl | 4-chlorophenyl | NMe₂ | 1 | 1 | 1 | 10c | |
| 28 | A | heptyl | 4-chlorophenyl | NMe₂ | 1 | 2 | 18 | 1 | 230° C./0.5 mm Hg |
| 29 | A | 7-octenyl | 4-chlorophenyl | NMe₂ | 1 | 1 | 2 | 10b | |
| 30 | A(c) | cyclohexylmethyl | 3,4-dichlorophenyl | NMe₂ | 1 | 1 | 18 | 4 | 182–184° C. |
| 31 | A | 3-methoxypropyl | 4-chlorophenyl | NMe₂ | 1 | 1 | 1.5 | 5 | 112–113° C. |
| 32 | A | 3-methoxybutyl | 4-chlorophenyl | NMe₂ | 1 | 1 | 1 | 9 | |
| 33 | A(c) | 3-methoxybutyl | 3,4-dichlorophenyl | NMe₂ | 1 | 1 | 1 | 9 | |
| 34 | B(c) | Me | 3,4-dichlorophenyl | NHBuⁱ | 1 | 3 | 1 | 8 | 63.5–65.5° C. |
| 35 | B(b) | Me | 3,4-dichlorophenyl | N(Me)Bu | 1 | 1 | 1.5 | 1 | 190–200° C./0.2 mm Hg |
| 36 | B(a) | Me | 3,4-dichlorophenyl | morpholino | 1 | 1 | 5 | 4 | 105–110° C. |
| 37 | B | Et | 3,4-dichlorophenyl | 4-methylpiperidino | 1 | 1 | 2 | 4 | 113–117° C. |
| 38 | B(d) | Et | 3,4-dichlorophenyl | N(Me)(2-morpholinoethyl) | 1 | 1 | 2 | 4 | 116–120° C. |
| 39 | B(e) | Et | 3,4-dichlorophenyl | N(Me)(2-hydroxyethyl) | 1 | 1 | 1 | 4a | |
| 40 | B(f) | Et | 3,4-dichlorophenyl | 1,2,3,6-tetrahydro-1-pyridyl | 1 | 1 | 2 | 4 | 110–114° C. |
| 41 | B(g) | Et | 3,4-dichlorophenyl | N(Me)(cyclohexyl) | 1 | 1 | 1 | 4 | 180–183° C. |
| 42 | B(j) | Et | 3-trifluoromethylphenyl | N(Me)(2-morpholinoethyl) | 1 | 1 | 1 | 4a | |
| 43 | B(h) | Et | 3,4-dichlorophenyl | piperidino | 1 | 1 | 1 | 4 | 77–85° C. |
| 44 | B(i) | Et | 4-chlorophenyl | NEt₂ | 1 | 1 | 1.5 | 4 | 115° C. (dec) |

EXAMPLE 45

A portion (70 ml) of a 0.305M solution of 3-(1-ethoxyethoxy)propyllithium [prepared from 1-bromo-3-(1-ethoxyethoxy)propane (21.8 g) and lithium wire (2.07 g) in ether (80 ml)] was added under argon to a stirred solution of the product of Example A(c) (5 g) in toluene (50 ml) at 20°–25° C. The mixture was stirred at ambient temperature for 16 hours. Water (40 ml) and then 5N hydrochloric acid (50 ml) were added with cooling to maintain the temperature below 25° C. The resulting mixture was poured into water (200 ml) and the aqueous layer basified and extracted with ether. The extract was dried, filtered and evaporated to give 1-[1-(3,4-dichlorophenyl)cyclobutyl]-1-dimethylamino-5-hydroxypentan-2-one which was purified by flash chromatography using 75:25 mixture of petroleum ether (b.p. 40°–60° C.) and ether as the eluant to give an oil the boiling point of which was not determined.

EXAMPLE 46

Triethylamine and then a solution of acetyl chloride in ether were added dropwise to a solution of the product of Example 45 in ether and the mixture was heated under reflux for 90 minutes, cooled and filtered. The filtrate was diluted with water and extracted with ether. The extract was washed, dried and evaporated to give an oil which was distilled on a Buchi Kugelrohr apparatus (200°/0.5 mm) to give 5-[1-(3,4-dichlorophenyl)cyclobutyl]-5-dimethylamino-4-oxopentyl acetate.

EXAMPLE 47

A 1.55M solution of n-butyllithium in hexane (129 ml) was added to a stirred solution of diisopropylamine (22.3 g) in dry tetrahydrofuran (90 ml) and the resulting mixture was stirred for 30 minutes at 0° C. The mixture was then cooled to −70° C. in an acetone/dry ice bath and a solution of 2-[1-(4-chlorophenyl)cyclobutyl]-2-dimethylaminoacetonitrile (30 g prepared as described in Example A) in dry tetrahydrofuran (100 ml) was added to the reaction mixture under nitrogen over 50 minutes at −70° C. and then stirred for 1½ hours at a temperature of less than 5° C. The mixture was then cooled to −70° C. and treated with a solution of acetaldehyde (13.6 g) in dry tetrahydrofuran (40 ml). After the mixture had been stirred for 1 hour at −70° C. under nitrogen the mixture was treated with excess saturated ammonium chloride solution and allowed to warm to 0° C. The aqueous layer was then separated and extracted with ether. The extract was combined with the organic phase of the reaction mixture, dried and the solvents removed by evaporation to give an oil which was distilled (eliminating hydrogen cyanide) (154°–160° C./5 mm Hg) to give 1-[1-(4-chlorophenyl)cyclobutyl]-1-dimethylaminopropan-2-one.

EXAMPLE 48

In a similar manner to that described in Example 47, 1-[1-(4-chlorophenyl)cyclobutyl]-1-dimethylamino butan-2-one was prepared. The fractions collected in the boiling point range 136°–140° C./2 mm Hg were purified by high performance liquid chromatography on a silica column followed by flash chromatography using a mixture of equal parts of ethyl acetate and petroleum ether (b.p. 60°–80° C.) as eluant. The product was then dissolved in propan-2-ol and excess concentrated hydrochloric acid was added. The solvents were removed by evaporation and the residue dried by azeotropic distillation with propan-2-ol to give a solid with was recrystallised from propan-2-ol to give 1-[1-(4-chlorophenyl)cyclobutyl]-1-dimethylaminobutan-2-one hydrochloride (m.p. 174°–176° C.).

EXAMPLE 49

1-[1-(4-chlorophenyl)cyclobutyl]-1-dimethylamino-3-methylbutan-2-one (1 g prepared in a similar manner to that described in Example 47 and having a boiling point range 144°–148° C./2 mm Hg) was heated under reflux for 20 minutes with a mixture of 30% aqueous oxalic acid solution (9 ml) and methanol (90 ml). The reaction mixture was poured into water and the aqueous mixture was washed with ether, basified and extracted with ether. The solvent was removed from the dried ethereal extract and the residue was treated with a mixture of excess concentrated hydrochloric acid and propan-2-ol. Removal of the solvents gave a residue which was dried by azeoptropic distillation with propan-2-ol. The residue was then triturated with acetone to give a solid which was recrystallised twice from propan-2-ol to give 1-[1-(4-chlorophenyl)cyclobutyl]-1-dimethylamino-3-methylbutan-2-one hydrochloride (m.p. 202°-204° C.).

EXAMPLE 50

A solution of 2-[1-(3,4-dichlorophenyl)cyclobutyl]-2-dimethylaminoacetonitrile (28.3 g prepared as described in Example A(c)) in dry tetrahydrofuran (150 ml) was added with stirring to a solution of lithium diisopropylamide [prepared by the addition of a 1.6M solution of butyllithium in hexane (100 ml) to a solution of diisopropylamine (22.4 ml) in ether (200 ml) followed by removal of the solvents at 80° C. and disolution of the residue in tetrahydrofuran (100 ml)] at −20° C. The temperature of the solution was maintained at −12° C. for 30 minutes. The mixture was then cooled to −40° C. and propionaldehyde (20 ml) was added. The temperature was allowed to rise to −10° C. and an excess of aqueous ammonium chloride solution was added at the same temperature. The aqueous layer was separated and extracted with ether and the extract combined with the organic phase of the reaction mixture. The resulting organic phase was dried and the solvents removed. The residue was distilled (eliminating hydrogen cyanide) (154° C./6mm Hg to 180° C./1.2 mm Hg) to give an oil which was dissolved in petroleum ether (40°-60° C.). A solid which separated from the solution was collected by filtration and discarded and the filtrate evaporated. The residue was dissolved in methanol, oxalic acid (20 g) was added and the mixture heated at 90°-95° C. for 40 minutes. The solution was poured into water (ca. 1.5 litres) and the resulting mixture was washed with ether, basified and extracted with ether, The extract yielded an oil which was distilled in a Buchi Kugelrohr apparatus (175° C./0.9 mm Hg) to give 1-[1-(3,4-dichlorophenyl)cyclobutyl]-1-dimethylaminobutan-2-one

EXAMPLE 51

A solution of 2-[1-(4-chlorophenyl)cyclobutyl]-2-dimethylaminoacetonitrile (15 g prepared as described in Example A) in dry tetrahydrofuran (50 ml) was added with stirring at −70° C. over a period of 35 minutes to a solution of lithium diisopropylamide [prepared by the addition of a 2.7M solution of butyllithium in hexane (37 ml) to a solution of diisopropylamine (15 ml) in dry tetrahydrofuran (45 ml) at 5° C.] followed by stirring for 1 hour at a temperature below 5° C. A portion (ca. 100 ml) of the above solution was cooled to −70° C. A solution of hexanal (12 ml) in dry tetrahydrofuran (20 ml) was added over 10 minutes and the mixture stirred for 1 hour at −70° C. The temperature was maintained at −70° C. whilst excess saturated ammonium chloride solution was added and the mixture was then allowed to warm to ambient temperature. The mixture was extracted with ether and the dried extract evaporated to give an oil which was distilled (160°-170° C./1 mm Hg) eliminating hydrogen cyanide. The distillate was dissolved in excess 2N hydrochloric acid to give an aqueous solution which was washed with ether, basified and extracted with ether. The extract was dried and the solvent removed by evaporation to give an oil which was distilled in a Buchi Kugelrohr apparatus (250°/1 mm) to give 1-[1-(4-chlorophenyl)cyclobutyl]-1-dimethylaminoheptan-2-one.

EXAMPLE 52

A solution of 2-[1-(3,4-dichlorophenyl)cyclobutyl]-2-dimethylaminoacetonitrile (11.3 g prepared as described in Example A(c)) in tetrahydrofuran (20 ml) was added over a period of ten minutes to a solution of lithium diisopropylamide at −50° C. [prepared by the addition of a 2.7M solution of butyllithium in hexane (24.7 ml) to a solution of diisopropylamine (10.25 ml) in dry tetrahydrofuran (30 ml) at 10°-15° C. under argon] and the mixture was allowed to warm to 3° C. and maintained at 3° C. for 30 minutes. The mixture was cooled to −70° C. and cyclohexanecarbaldehyde (11.5 g) was added with stirring over a period of 20 minutes. Stirring was continued at this temperature for a further 40 minutes and then saturated aqueous ammonium chloride solution (100 ml) was added slowly at −70° C. The mixture was allowed to warm to 20°-25° C. and the aqueous layer was separated and extracted with ether. The ether extracts were combined with the organic layer of the reaction mixture, dried and evaporated to give an oil which was heated (eliminating hydrogen cyanide) at 90°-95° C. for 3 hours and then cooled and dissolved in methanol (100 ml). Oxalic acid (10 g) was added and the mixture heated at 90°-95° C. for one hour. The mixture was cooled, basified and extracted with ether. The ether extract was dried and evaporated to give an oil which was purified by flash chromatography using a 95:5 mixture of petroleum ether and ether as eluant. The resulting oil solidified on standing and was recrystallised from petroleum ether (b.p. 60°-80° C.) to give 1-cyclohexyl-2-[1-(3,4-dichlorophenyl)cyclobutyl]-2-dimethylaminoethanone (m.p. 79°-80° C.).

EXAMPLE 53

A portion (10 ml) of a solution of 2-(3-bromopropyl)-2-methyl-1,3-dioxolane (27.5 g) in dry tetrahydrofuran (70 ml) and an iodine crystal were added to a mixture of magnesium (3.5 g) and tetrahydrofuran (10 ml). The mixture was heated under reflux and a further portion (10 ml) added. When the reaction had been initiated the remaining solution was added over 40 minutes and reflux was maintained. 1-(3,4-Dichlorophenyl)cyclobutanecarbonitrile (18 g) and then dry tetrahydrofuran (10 ml) were added and the resulting solution heated under reflux for two hours. The solution was cooled, a slurry of sodium borohydride (5 g) and propan-2-ol (50 ml) was added and the mixture stirred at ambient temperature for 16 hours. Propan-2-ol (100 ml) was added and the mixture heated under reflux for 2.75 hours and then cooled and poured into ice/water (1000 g). The aqueous mixture was extracted with ether and the extract was dried and evaporated to give 1-[1-(3,4-dichlorophenyl)cyclobutyl]-4-(2-methyl-1,3-dioxolan-2-yl)butylamine.

A mixture of the above compound (20 g), 37-40% aqueous formaldehyde (20 ml), methanol (750 ml) and 1N solution of sodium dihydrogen phosphite [prepared by the reaction of phosphorous acid (26.6 g) in water (50 ml) with sodium bicarbonate (26.9 ml) and then adding water to give a volume of 350 ml] was heated under reflux for two hours. Methanol was removed by evaporation in vacuo at 50° C. The residue was added to ice and extracted with ether. The ether extract was dried and evaporated to give N,N-dimethyl-1-[1-(3,4-dichlorophenyl)cyclobutyl]-4-(2-methyl-1,3-dioxolan-2-yl)butylamine as an oil which was added to a mixture of water (200 ml) and 5N hydrochloric acid (100 ml). Water (100 ml) was added and the mixture heated on a steam bath for one hour. The cooled mixture was washed with petroleum ether and with ether, basified and extracted with ether. The ether extract was dried and evaporated to give 6-[1-(3,4-dichlorophenyl)cyclobutyl]-6-dimethylaminohexan-2-one as an oil the boiling point of which was not determined.

EXAMPLES 54 AND 55

In a similar manner to that described in Example 53, 2-(5-bromopentyl)-2-methyl-1,3-dioxolane was used to prepare 8-[1-(4-chlorophenyl)cyclobutyl]-8-dimethylaminooctan-2-one and 8-[1-(3,4-dichlorophenyl)cyclobutyl]-8-dimethylaminooctan-2-one which were isolated as oils, the boiling points of which were not determined.

EXAMPLES 56 AND 57

In a similar manner to that described in Example 53, except that the formation of the Grignard reagent was initiated by the addition of ethyl bromide and sufficient tetrahydro- furan was added to provide a solution, 2-(7-bromo- heptyl)-2-methyl-1,3-dioxolane was used to prepare 10-[1-(4-chlorophenyl)cyclobutyl]-10-dimethylaminodecan-2-one and 10-[1-(3,4-dichlorophenyl)cyclobutyl)-10-dimethylaminodecan-2-one which were both distilled in a Buchi Kugelrohr apparatus (160° C./0.2 mm Hg) to give the desired products as oils, the boiling points of which were not determined.

EXAMPLE 58

1-[1-(3,4-Dichlorophenyl)cyclobutyl]-4-(2-methyl-1,3-dioxolan-2-yl)butylamine prepared as described in Example 53 was converted into the corresponding N,N-dimethyl compound in a similar manner to that described in Example 53. The compound was then dissolved in ether and treated with a solution of maleic acid in ether to give a gum which was triturated with ether to give a residue which was basified to yield N,N,-dimethyl-1-[1-(3,4-dichlorophenyl)cyclobutyl-4-(2-methyl-1,3-dioxolan-2-yl)butylamine as an oil, the boiling point of which was not determined.

EXAMPLE 59

Solid sodium cyanoborohydride (0.5 g) and acetonitrile (5 ml) were added to a mixture of 1-[1-(3,4-dichlorophenyl)cyclobutyl]-4-(2-methyl-1,3-dioxolan-2-yl)butylamine (2 g prepared as described in Example 53) and 37-40% aqueous formaldehyde (2 ml) in acetonitrile (15 ml). The mixture was allowed to stand for 1½ hours and the solvent was removed by evaporation. A solution of the residue in ether was washed with water, dried and evaporated to give an oil which was purified as described in Example 58 to give N,N-dimethyl-1-[1-(3,4-dichlorophenyl)cyclobutyl]-4-(2-methyl-1,3-dioxolan-2-yl)butylamine the boiling point of which was not determined.

EXAMPLE 60

A solution of p-toluenesulphonylmethylisocyanide sold under the trade name TosMIC (5 g) in dimethylformamide (10 ml) was added at 0° C. under argon over a period of 10 minutes to a stirred suspension of sodium hydride (3.6 g of a 50% dispersion in mineral oil) in dimethylformamide (30 ml). Ethanol (3.6 ml) was then added at 0° C. After 30 minutes a solution of 6-[1-(4-chlorophenyl)cyclobutyl]-6-dimethylaminohexan-2-one (6.11 g prepared in a similar manner to that described in Example 53) in tetrahydrofuran (50 ml) was added at 0° C. and the mixture stirred at ambient temperature for 16 hours. The reaction mixture was poured into water and the aqueous mixture extracted with ether. The extracts were washed, dried and evaporated to give an oil which was distilled on a Buchi Kugelrohr apparatus (150° C./0.35 mm). The distillate was dissolved in ether and treated with maleic acid to give a gum which was washed with ether and basified to give 6-[1-(4-chlorophenyl)cyclobutyl]-6-dimethylamino-2-methylhexanenitrile (mp 54°–56° C.)

A solution of 6-[1-(4-chlorophenyl)cyclobutyl]-6-dimethylamino-2-methylhexanenitrile (2.25 g) in ether (15 ml) was added to a solution of methylmagnesium bromide [prepared from magnesium (0.29 g) and excess methylbromide gas in ether (20 ml)]. The mixture was stirred for one hour at 20° C. and then the ether was replaced by toluene (40 ml) and the mixture heated at 90° C. for 4 hours and then allowed to stand for 2½ days at ambient temperature. The mixture was added to 1N hydrochloric acid (100 ml) and the mixture heated at 90°–95° C. for 30 minutes, cooled, basified with aqueous sodium hydroxide solution and extracted with ether. Removal of the ether from the dried extract gave a residue which was distilled on a Buchi Kugelrohr apparatus (170° C./0.5 mm) to give 7-[1-(4-chlorophenyl)-cyclobutyl]-7-dimethylamino-3-methylheptan-2-one.

EXAMPLE 61

1-(3,4-Dichlorophenyl)cyclobutanecarbonitrile (8 g) was added to the Grignard reagent prepared by the reaction under argon of 2-(3-bromopropyl)-5-methylfuran (10 g) and magnesium (1.1 g) in ether (20 ml). The mixture was stirred for 16 hours at ambient temperature. A suspension of sodium borohydride (3 g) in propan-2-ol (100 ml) was added and the mixture heated under reflux for 4.75 hours and then allowed to cool. The mixture was added to water with cooling and excess 2N hydrochloric acid added. The aqueous acid layer was extracted with ether and the extract washed with 1N aqueous sodium hydroxide solution, dried and evaporated to yield 1-[1-(3,4-dichlorophenyl)cyclobutyl]-4-(5-methyl-2-furyl)butylamine.

The products prepared in the preceding paragraph (13 g) was added to a mixture of 37–40% aqueous formaldehyde solution (28 ml) and a 1N aqueous solution of sodium dihydrogen phosphite (185 ml prepared from phosphorous acid and sodium bicarbonate). Methanol (600 ml) was added and the mixture heated under reflux for one hour. The methanol was removed by evaporation and the aqueous residue basified and extracted with ether. The extract was washed with saturated aqueous ammonium chloride solution, the ether separated, dried and evaporated to give a residue which was distilled (160°–180° C./0.2 mm) to give N,N-dimethyl-1-[1-(3,4-dichlorophenyl)cyclobutyl]-4-(5-methyl-2-furyl)butylamine.

The product prepared in the preceding paragraph (1.1 g) was stirred with a mixture of glacial acetic acid (26 ml), water (0.82 ml) and concentrated sulphuric acid (0.18 ml) and then heated at 75°–85° C. for 70 minutes and then cooled. The mixture was added to excess sodium bicarbonate and water was added. The resulting mixture was extracted with ether and the extract dried and evaporated to give an oil which was purified by flash chromatography using a 1:1 mixture of ether and petroleum ether (bp 40°-60° C.) as eluant to give 9-[1-(3,4-dichlorophenyl)cyclobutyl]-9-dimethylaminononane-2,5-dione the boiling point of which was not determined.

EXAMPLE 62

A solution of 1-[1-(4-chlorophenyl)cyclobutyl]-1-dimethylaminopropan-2-one (1.9 g prepared as described in Example 47) in ethanol (10 ml) was added dropwise to a suspension of sodium borohydride (0.4 g) in ethanol (20 ml) and the mixture was stirred for 4 hours at ambient temperature. 5N Sulphuric acid (10 ml) was added and then the acidified mixture was basified. The resulting mixture was extracted with ether and the ether extracts were washed with water and dried. Removal of the solvent gave an oil which was converted into a hydrochloride salt by treatment with a mixture of excess concentrated hydrochloric acid and propan-2-ol. The residue after the removal of the solvents was dried by azeotropic distillation with propan-2-ol to give 1-[1-(4-chlorophenyl)cyclobutyl]-1-dimethylaminopropan-2-ol hydrochloride (m.p. 255° C.).

EXAMPLE 63

A solution of 1-[1-(4-chlorophenyl)cyclobutyl]-1-dimethylaminobutan-2-one (3 g prepared as described in Example 48) in industrial methylated spirit (15 ml) was added dropwise to a stirred suspension of sodium borohydride (0.6 g) in industrial methylated spirit (30 ml) and the mixture was stirred at ambient temperature for two hours. The reaction mixture was heated under reflux for two hours, cooled and poured into water. Concentrated sulphuric acid was added and the acidified mixture was cooled in an ice bath and basified. The aqueous mixture was extracted with ether and the extract dried. Removal of the solvent by evaporation gave an oil which was treated with a mixture of excess concentrated hydrochloric acid and propan-2-ol and then the solvents were removed by evaporation. The residue was dried by azeotropic distillation with propan-2-ol to give a solid which was recrystallised from propan-2-ol to give 1-[1-(4-chlorophenyl)cyclobutyl]-1-dimethylaminobutan-2-ol hydrochloride (m.p. 224°-227° C.).

EXAMPLE 64

A solution of 1-[1-(4-chlorophenyl)cyclobutyl]-1-dimethylamino-3-methylbutan-2-one in the form in the from of its free base (4 g prepared as described in Example 49) in industrial methylated spirit (18 ml) was added dropwise to a stirred suspension of sodium borohydride (0.7 g) in industrial methylated spirit (40 ml) and the mixture was stirred for 16 hours. Sodium borohydride (0.7 g) was added and the mixture heated under reflux for 3 hours. After cooling the mixture was poured into water and acidified with concentrated sulphuric acid. 5N Sodium hydroxide solution was added with cooling and the basic aqueous liquors were extracted with ether. The extracts were washed with water and dried and the solvent was removed by evaporation to leave an oil which was converted into a hydrochloride salt by treatment with a mixture of excess concentrated hydrochloric acid and propan-2-ol. The residue was dried by azeotropic distillation with propan-2-ol to give 1-[1-(4-chlorophenyl)cyclobutyl]-1-dimethylamino-3-methylbutan-2-ol hydrochloride (m.p. 229°-231° C.).

EXAMPLE 65

A solution of the product of Example 53 (2 g) in propan-2-ol (50 ml) and sodium borohydride (1 g) were heated under reflux for 2 hours. The mixture was allowed to stand for 16 hours at ambient temperature and was poured into water (500 ml). The resulting mixture was extracted with ether and the ether extracts were dried and evaporated to give 6-[1-(3,4-dichlorophenyl)-cyclobutyl]-6-dimethylaminohexan-2-ol as an oil the boiling point of which was not determined.

EXAMPLE 66

In a similar manner to that described in Example 65, the product of Example 55 was reduced to 8-[1-(3,4-dichlorophenyl)cyclobutyl]-8-dimethylaminooctan-2-ol which was obtained as an oil the boiling point of which was not determined.

EXAMPLES 67

The product of Example 23 (1.1 g) was added to a mixture of sodium borohydride (0.5 g) and propan-2-ol (20 ml) and heated under reflux for ten hours. The mixture was cooled and added to water. The aqueous mixture was extracted with ether and the ether evaporated to give a residue which was purified by flash chromatography using a mixture of 95% petroleum ether (b.p. 60°-80° C.) and 5% triethylamine as eluant to give 1-[1-(3,4-dichlorophenyl)cyclobutyl-1-dimethylamino-6-hepten-2-ol as a colourless oil the boiling point of which was not determined.

EXAMPLE 68

A mixture of the product of Example 13 in the form of its free base (2.66 g), sodium borohydride (0.772 g) and ethanol (50 ml) was heated under reflux for 2½ hours. Three further portions of sodium borohydride (each 0.772 g) were added over a period of 3.25 hours and the mixture heated under reflux for 2½ days. The reaction mixture was evaporated to give a residue to which water and then 2.5N hydrochloric acid was added. The mixture was basified and extracted with ether and the extract was washed, dried and evaporated to give a residue which was dissolved in tetrahydrofuran (20 ml). Boranedimethylsulphide complex (2 ml) was added dropwise under nitrogen at ambient temperature and the mixture stirred for 3 hours and then cooled to 0° C. Water (25 ml) and then 5N hydrochloric acid (25 ml) were added and then the mixture was basified and the aqueous layer separated and extracted with ether. The ether extract and the organic phase of the reaction mixture were combined, washed with water, dried and evaporated to give an oil which was dissolved in ether. Hydrogen chloride gas was passed into the solution to give 1-dimethylamino-1-[1-(3-trifluoromethylphenyl)-cyclobutyl]pentan-2-ol hydrochloride (m.p. 202°-205° C.).

EXAMPLE 69

Boranedimethylsulphide complex (3 ml) was added dropwise under nitrogen over a period of 20 minutes to a solution of 1-dimethylamino-1-[1-(4-tolyl)cyclobutyl]-pentan-2-one (1.85 g prepared as described in Example 16) in tetrahydrofuran (20 ml) and the resulting mixture stirred for 3 days at ambient temperature. The mixture was cooled to 0° C. and water (25 ml) and then 5N hydrochloric acid (25 ml) added. The mixture was basified and the tetrahydrofuran removed by evaporation.

The residue was extracted with ether and the extracts washed with water, dried, filtered and evaporated to give an oil which was dissolved in petroleum ether (b.p. 80°-100° C.) and purified on a column packed with magnesia-silica gel sold under the trade name Florisil using petroleum ether (b.p. 80° to 100° C.) as eluant. The eluate was evaporated to give an oil which was distilled (215° C./1.5 mm Hg) to give 1-dimethylamino-1-[1-(4-tolyl)cyclobutyl]pentan-2-ol.

EXAMPLES 70 TO 80

In a similar manner to that described in Example 69 the compounds of formula I listed in Table IV were made from ketones prepared as described in the Examples identified in Table IV and isolated by methods indicated by the numbers in the column headed PM.

bromide (5 ml) in dry ether (20 ml) with magnesium (1.3 g) in dry ether (160 ml). The mixture was stirred for two hours at ambient temperature and water (60 ml) and then 5N hydrochloric acid (60 ml) were added. The mixture was allowed to stand for 16 hours and the aqueous layer was separated, washed with ether, basified and extracted with ether. The extract was dried and the ether removed to give an oil which was treated with a mixture of excess concentrated hydrochloric acid and propan-2-ol. Evaporation yielded a gum which was dissolved in acetone. The volume of the acetone solution was reduced and a solid precipitated which was collected and recrystallised from propan-2-ol to give 1-[1-(4-chlorophenyl)cyclobutyl]-1-dimethylamino-2-methylbutan-2-ol hydrochloride (m.p. 167°-170° C. (dec)).

TABLE IV

| Ex. | Starting ketone Ex. | $NR_1R_2$ | $R_3$ | $R_4$ | m.p. °C. | PM |
| --- | --- | --- | --- | --- | --- | --- |
| 70 | 36 | morpholino | 3,4-dichlorophenyl | CH(OH)Me | 130–135 | (1) |
| 71 | 21 | $NMe_2$ | 3,4-dichlorophenyl | $CH(OH)CH_2CHMe_2$ | 71–80 (dec) | (1) |
| 72 | 35 | N(Me)Bu | 3,4-dichlorophenyl | CH(OH)Me | 123–128 | (1) |
| 73 | 41 | N(Me)cyclo-hexyl | 3,4-dichlorophenyl | CH(OH)Et | 156–161 | (1) |
| 74 | 9 | $NMe_2$ | 2-naphthyl | CH(OH)Et | 163–164 | (2) |
| 75 | 8 | $NMe_2$ | 3-trifluoromethylphenyl | CH(OH)Et | | (3) |
| 76 | 6 | $NMe_2$ | 4-methoxyphenyl | CH(OH)Et | | (4) |
| 77 | 43 | piperidino | 3,4-dichlorophenyl | CH(OH)Et | 110–115 | (1) |
| 78 | 42 | N(Me)(2-mor-pholinoethyl) | 3-trifluoromethylphenyl | CH(OH)Et | | (5) |
| 79 | 44 | $NEt_2$ | 4-chlorophenyl | CH(OH)Et | | (3) |
| 80 | 3 | $NMe_2$ | 4-bromophenyl | CH(OH)Et | 81.5–82.5 | (6) |

Notes to column PM in Table IV
(1) Product isolated as its hydrochloride salt the melting point of which is given.
(2) Product isolated as its oxalate salt the melting point of which is given. The product was not purified by chromatography.
(3) Product isolated as the free base the boiling point of which was not determined.
(4) The product was distilled on a Kugelrohr apparatus (240°/1 mm).
(5) Product isolated as the dihydrochloride salt the melting point of which could not be determined.
(6) Product isolated in the form of its free base as a solid the melting point of which is given.

EXAMPLE 81

In a similar manner to that described in Example 69, 1-[1-(3,4-dichlorophenyl)cyclobutyl]-1-piperidinopropan-2-one prepared in a similar manner to that described in Example 43 was reduced to 1-[1-(3,4-dichlorophenyl)cyclobutyl]-1-piperidinopropan-2-ol which was isolated as its hydrochloride salt (m.p. 90°-100° C.).

EXAMPLE 82

A solution of 1-[1-(4-chlorophenyl)cyclobutyl]-1-dimethylaminopropan-2-one (3.1 g prepared as described in Example 47) in dry ether (10 ml) was added dropwise under nitrogen to a solution of methylmagnesium bromide prepared by passing methyl bromide gas into a mixture of magnesium (0.4 g) and dry ether (50 ml). The mixture was stirred at ambient temperature for two hours. Water (20 ml) and then 5N hydrochloric acid (20 ml) were added and the mixture allowed to stand for 16 hours. The mixture was then washed with ether, basified and extracted with ether. Removal of the solvent by evaporation left an oil which was converted into 1-[1-(4-chlorophenyl)cyclobutyl]-1-dimethylamino-2-methylpropan-2-ol hydrochloride (m.p. 189°-190° C.) in a similar manner to that described in Example 59.

EXAMPLE 83

A solution of 1-[1-(4-chlorophenyl)cyclobutyl]-1-dimethylaminopropan-2-one (10 g prepared as described in Example 47) in dry ether (25 ml) was added dropwise to a stirred solution of ethyl magnesium bromide prepared by the reaction of a solution of ethyl

EXAMPLE 84

A solution of 1-[1-(4-chlorophenyl)cyclobutyl]-ethanone (88 g) in industrial methylated spirit (300 ml) was mixed with a solution of hydroxylamine hydrochloride (42 g) and sodium acetate (70 g) in water (200 ml). The mixture was heated at 90°-95° C. for 30 minutes. The volume was reduced by evaporation and 1-[1-(4-chlorophenyl)cyclobutyl]ethanone oxime precipitated on cooling.

A 1.6M solution of butyllithium in hexane (55 ml) was added to a stirred solution of the 1-[1-(4-chlorophenyl)cyclobutyl]ethanone oxime (8.94 g) in dry tetrahydrofuran (120 ml) the temperature being maintained below 0° C. for 40 minutes. The mixture was cooled to −5° C. and acetone (2.67 ml) was added dropwise. The temperature of the reaction mixture was allowed to rise to ambient temperature over a period of 16 hours. The mixture was cooled to 10° C. and water (100 ml) was added and the resulting aqueous mixture was washed with ether. The aqueous layer was acidified with 5N sulphuric acid and an oil separated. The oil was dissolved in ether and the ether solution was washed with water, dried and evaporated to yield 1-[1-(4-chlorophenyl)cyclobutyl]-3-hydroxy-3-methylbutan-1-one oxime.

A solution of 1-[1-(4-chlorophenyl)cyclobutyl]-3-hydroxy-3-methylbutan-1-one oxime (2 g) in methanol (70 ml) was cooled to −10° C. and molybdic acid (1.67 g) added with stirring. Sodium borohydride (2.7 g) was added portionwise. The temperature of the reaction mixture was maintained at 0° C. for 2½ hours and then water (200 ml) was added. The reaction mixture was extracted with ether, the extract filtered, and the filtrate washed with water and dried. Removal of the solvents yielded an oil which was dissolved in ether. A solution of maleic acid in ether was added and a gum was formed which solidified to give 4-amino-4-[1-(4-chlorophenyl)-cyclobutyl]-2-methylbutan-2-ol maleate (m.p. 139°–144° C. (dec)).

EXAMPLE 85

A solution of 1-[1-(4-chlorophenyl)cyclobutyl]-3-hydroxy-3-methylbutan-1-one oxime (3 g prepared as described in Example 84 above) in dry tetrahydrofuran (20 ml) was added under nitrogen to lithium aluminium hydride (2 g). The mixture was heated under reflux for 3 hours and then left without further heating for 16 hours. Water (100 ml) was added dropwise and the organic layer was separated. The aqueous layer was extracted with ether and the extracts combined with the organic layer and dried. The solvents were evaporated to give an oil which was dissolved in ether. Addition of a solution of maleic acid in ether gave a gum which slowly solidified. The solid was added to an aqueous solution of sodium hydroxide and the mixture extracted with ether. Removal of the ether gave an oil which was purified by high performance liquid chromatography to give 4-amino-4-[1-(4-chlorophenyl)cyclobutyl]-2-methylbutan-2-ol (m.p. 60°–62° C. shrinks 50° C.).

EXAMPLE 86

In a similar manner to that described in Example 84 above 1-[1-(4-chlorophenyl)cyclobutyl]-3-hydroxy-3-methylpentan-1-one oxime was prepared by the reaction of 1-[1-(4-chlorophenyl)cyclobutyl]ethanone oxime with butyllithium followed by butan-2-one.

A solution of 1-[1-(4-chlorophenyl)cyclobutyl]-3-hydroxy-3-methylpentan-1-one oxime (4.6 g) in dry 1,2-dimethoxyethane (16 ml) was added at 0° C. over a period of 40 minutes to the mixture prepared by adding titanium (IV) chloride (3.6 ml) dropwise and then sodium borohydride (2.5 g) portionwise to stirred dry 1,2-dimethoxyethane (62 ml) at 0° C. under nitrogen. The reaction mixture was stirred for 14 hours at room temperature under nitrogen and cooled to 0° C. Water (160 ml) was added dropwise and the mixture basified by the addition of aqueous ammonia solution (17 ml - S.G. 0.880) and extracted with ether. The extracts were washed with brine, dried and the solvent removed to yield 1-amino-1-[1-(4-chlorophenyl)cyclobutyl]-3-methylpentan-3-ol which was dissolved in ether (70 ml). A solution of maleic acid (1.8 g) in ether (170 ml) was added and 1-Amino-1-[1-(4-chlorophenyl)cyclobutyl]-3-methylpentan-3-ol maleate (m.p. 106° C.(dec) softens 101° C.) was deposited.

EXAMPLES 87 TO 129

In a similar manner to that described in Example 86 the compounds of formula I in which $R_1$ and $R_2$ are H and in which $R_4$ is a group of formula III listed in Table V were prepared

TABLE V

| Ex. | $R_3$ | $R_8$ | $R_9$ | | Notes |
|---|---|---|---|---|---|
| 87 | 4-chlorophenyl | H | Et | 4 | 185°/0.3 mm |
| 88 | 4-chlorophenyl | Me | Me | 1 | 145° (dec) |
| 89 | 3-chlorophenyl | Me | Me | 4 | 160°/0.2 mm |
| 90 | phenyl | Me | Me | 1 | 121–123° (dec) |
| 91 | 3-trifluoromethyl phenyl | Me | Me | 1 | 147–148° |
| 92 | 4-chlorophenyl | Me | $CF_3$ | 1 | 179° (dec) |
| 93 | 4-fluorophenyl | Me | $CF_3$ | 4 | 170°/0.1 mm |
| 94 | 4-fluorophenyl | Me | Me | 2a | 215° (dec) |
| 95 | 3-fluorophenyl | Me | Me | 4 | 155°/0.1 mm |
| 96 | 4-biphenylyl | Me | Me | 6 | 125–127° |
| 97 | 4-methylthiophenyl | Me | Me | 6 | 111–113° |
| 98 | phenyl | Me | Et | 4 | 160°/0.2 mm |
| 99 | 3-fluorophenyl | Me | Et | 4 | 160°/0.2 mm |
| 100 | 3-chlorophenyl | Me | Et | 4 | 150°/0.1 mm |
| 101 | 4-methylthiophenyl | Me | Et | 4 | 180°/0.2 mm |
| 102 | 4-fluorophenyl | Me | Et | 4 | 170°/0.2 mm |
| 103 | 4-methoxyphenyl | Et | Et | 2b | 164–165° (dec) |
| 104 | phenyl | Et | Et | 2a | 214° (dec) |
| 105 | 4-chlorophenyl | Me | $(CH_2)_2OMe$ | 2a | 168–171° (dec) |
| 106 | 4-fluorophenyl | Me | $(CH_2)_2OEt$ | 4 | 170°/0.3 mm |
| 107 | 4-chlorophenyl | Me | morpholinomethyl | 2c | 145° (dec) |
| 108 | 4-fluorophenyl | Me | morpholinomethyl | 3 | 137° (dec) |
| 109 | 4-chlorophenyl | Et | $CH_2OMe$ | 3 | 167–170° (dec) |
| 110 | 4-methoxyphenyl | Me | Me | 4 | 175°/0.4 mm |
| 111 | 4-fluorophenyl | Et | Et | 4 | 170°/0.4 mm |
| 112 | 4-biphenylyl | Et | Et | 6 | 87–90° |
| 113 | 3-chlorophenyl | Et | Et | 4 | 160°/0.4 mm |
| 114 | 4-chlorophenyl | Me | Pr | 5 | |
| 115 | 4-chlorophenyl | Et | $Pr^i$ | 4 | 175°/0.2 mm |
| 116 | 4-chlorophenyl | Me | $Bu^t$ | 4 | 170°/0.2 mm |
| 117 | 4-chlorophenyl | Me | $Bu^i$ | 4 | 180°/0.4 mm |
| 118 | 4-chlorophenyl | Me | cyclopropyl | 5 | |
| 119 | 4-chlorophenyl | Me | $CH_2OMe$ | 4 | 180°/0.4 mm |
| 120 | 4-fluorophenyl | Me | $CH_2OMe$ | 4 | 165°/0.1 mm |
| 121 | 4-chlorophenyl | Pr | $CH_2OMe$ | 4 | 180°/0.2 mm |
| 122 | phenyl | Me | $(CH_2)_2OMe$ | 4 | 200°/0.2 mm |
| 123 | 4-fluorophenyl | Me | $(CH_2)_2OMe$ | 4 | 180°/0.2 mm |
| 124 | 4-chlorophenyl | Et | $(CH_2)_2OMe$ | 4 | 190°/0.2 mm |
| 125 | 4-chlorophenyl | Me | $(CH_2)_2OEt$ | 4 | 180°/0.4 mm |
| 126 | 4-fluorophenyl | Et | $CH_2OEt$ | 4 | 160°/0.1 mm |
| 127 | 3-fluorophenyl | Me | $(CH_2)_2OEt$ | 4 | 170°/0.2 mm |

TABLE V-continued

| Ex. | R₃ | R₈ | R₉ | | Notes |
|---|---|---|---|---|---|
| 128 | 4-chlorophenyl | Et | CH₂OEt | 4 | 180°/0.2 mm |
| 129 | 4-chlorophenyl | Me | CH(SMe)Me | 4 | 200°/0.1 mm |

Notes to Table V
1 Product prepared as a maleate salt the melting point of which is given in the last column of the Table.
2a, 2b, 2c Product prepared as an oxalate salt, the melting point of which is given in the last column of the Table. The number of moles of oxalic acid are 0.6 (Note 2a), 1 (Note 2b) and 1.5 (Note 2c) per mole of base.
3 Product prepared as a fumarate salt the melting point of which is given in the final column.
4 Product isolated as an oil by distillation under the conditions given in the final column.
5 Product prepared as an oil which was not distilled.
6 Product isolated as the free base in solid form. The melting point is given in the final column.

EXAMPLE 130

A mixture of the product of Example 85 (5.9 g), 37–40% aqueous formaldehyde (6.75 ml) and 98% formic acid (17 ml) was heated under reflux for 16 hours. The cooled reaction mixture was poured into a mixture of crushed ice and 16N aqueous sodium hydroxide solution (26 ml). The resulting mixture was extracted with ether and the extracts were washed with water, dried and evaporated. The product was distilled (150° C./0.5 mm Hg) and converted into 4-[1-(4-chlorophenyl)cyclobutyl]-4-dimethylamino-2-methylbutan-2-ol maleate (m.p. 60°–161° C. (dec)).

EXAMPLE 131

In a similar manner to that described in Example 130, the product of Example 90 was converted into the corresponding N,N-dimethyl compound which was purified by high performance liquid chromatography to give 4-dimethylamino-4-(1-phenylcyclobutyl)-2-methylbutan-2-ol as an oil the boiling point of which was not determined.

EXAMPLE 132

37–40% Aqueous formaldehyde solution (2 ml) and then sodium cyanoborohydride (0.475 g) were added to a stirred solution of the product of Example 111 (0.7 g) in dry acetonitrile (10 ml) at ambient temperature. Glacial acetic acid (0.25 ml) was added dropwise over a period of ten minutes and the mixture stirred for 2 hours at ambient temperature. Further glacial acetic acid (0.25 ml) was added and the mixture stirred for 30 minutes. The reaction mixture was extracted with ether. The ether extracts were washed with 1N aqueous potassium hydroxide solution, water and brine and then dried. The solvent was removed and the residue distilled (140°/0.3 mm) to give 1-dimethylamino-3-ethyl-1-[1-(4-fluorophenyl)cyclobutyl]pentan-3-ol.

EXAMPLES 133 TO 135

In a similar manner to that described in Example 132 the product of Example 94 was converted into 4-dimethylamino-4-[1-(4-fluorophenyl)cyclobutyl]-2-methylbutan-2-ol (b.p. 125°/0.4 mm), the product of Example 102 was converted into 1-dimethylamino-1-[1-(4-fluorophenyl)cyclobutyl]-3-methylpentan-3-ol (bp 145°/0.5 mm) and the product of Example 86 was converted into 1-[4-(chlorophenyl)cyclobutyl]-1-dimethylamino-3-methylpentan-3-ol (bp 140°/0.3 mm).

EXAMPLE 136

A 2.7M solution of butyllithium in hexane (24 ml) was added under nitrogen to a stirred solution of 1-[1-(4-chlorophenyl)cyclobutyl]ethanone oxime [prepared as described in Example 84 (7.2 g)] in dry tetrahydrofuran (100 ml) over a period of 45 minutes whilst maintaining the temperature in the range −3° to 0° C. The mixture was stirred at 0° C. for 1 hour and then cooled to −5° C. A solution of dry pentan-3-one (3.4 ml) in dry tetrahydrofuran (10 ml) was added, the temperature of the mixture was allowed to rise to ambient and the mixture was stirred under nitrogen for 16 hours. The mixture was cooled to below 10° C. and water (100 ml) was added dropwise under nitrogen. The mixture was extracted with ether, the extracts dried and evaporated and the residue triturated with ice-cold petroleum ether (b.p. 40°–60° C.) to give 1-[1-(4-chlorophenyl)cyclobutyl]-3-ethyl-3-hydroxypentan-1-one oxime (m.p 113°–115° C.).

Titanium (IV) chloride (3.9 ml) was added dropwise to stirred dry 1,2-dimethoxyethane (68 ml) cooled to 0° C. under nitrogen. The temperature was maintained at 0° C. and powdered sodium borohydride (2.7 g) was added. A solution of 1-[1-(4-chlorophenyl)cyclobutyl]-3-ethyl-3-hydroxypentan-1-one oxime (5.2 g) in dry 1,2-dimethoxyethane (17 ml) was then added dropwise under nitrogen and the mixture stirred for 30 minutes at 0° C. and then at ambient temperature for 14 hours. After cooling the mixture to 0° C., water (170 ml) was added dropwise and the mixture basified with aqueous ammonia solution (S.G. 0.880) with cooling. The resulting solution was extracted with ether and the extracts washed with brine and dried. Removal of the solvents by evaporation in vacuo gave an oil which was distilled (b.p. 150/0.05 mm) to give 1-[1-(4-chlorophenyl)cyclobutyl]-3-ethyl-1-iminopentan-3-ol.

A solution of 1-[1-(4-chlorophenyl)cyclobutyl]-3-ethyl-1-iminopentan-3-ol (1.6 g) in dry tetrahydrofuran (20 ml) was treated under nitrogen with boranetetrahydrofuran complex (1M solution in tetrahydrofuran 10 ml) and the mixture was heated under reflux for 24 hours. The mixture was cooled in ice and water and then 2N sodium hydroxide solution were added. The resulting mixture was extracted with ether and the extracts were washed, dried and evaporated to give 1-amino-1-[1-(4-chlorophenyl)cyclobutyl]-3-ethylpentan-3-ol which was then converted into the corresponding dimethylamino compound by heating a mixture of the primary amine (1.5 g), 98% formic acid (4 ml) and 37–40% aqueous formaldehyde (2 ml) at 90°–95° C. for 16 hours. The reaction mixture was cooled and poured into a mixture of 16N sodium hydroxide solution (7 ml) and ice. The mixture was extracted with ether and the extract washed, dried and evaporated to give a residue which was dissolved in ether. Addition of a solution of maleic acid in ether gave 1-[1-(4-chlorophenyl)cyclobutyl]-1-dimethylamino-3-ethylpentan-3-ol maleate (m.p. 110°–111° C.).

EXAMPLE 137

A suspension of zinc dust (25.5 g) (which had been activated by treatment with excess 3N hydrochloric acid followed by washing with water, ethanol and ether and drying) in dry tetrahydrofuran (250 ml) was stirred and heated under reflux while ethylbromoacetate (5 ml) was added dropwise. Stirring was continued for 15 minutes and 1-(4-chlorophenyl)cyclobutanecarbonitrile (15 g) was added. The mixture was heated under reflux and ethyl bromoacetate (60 g) was added over a period of 1 hour and the heating continued for a further 15 minutes. The mixture was then cooled and tetrahydrofuran (700 ml) and 25% aqueous potassium carbonate solution (300 ml) were added and the mixture was stirred for 15 minutes. The aqueous phase of the reaction mixture was separated, extracted with ether and the extracts combined with the organic phase of the reaction mixture, washed with brine and dried. Removal of the solvents gave an oil which was extracted with petroleum ether (b.p. 40°–60° C.). Removal of the solvent by evaporation gave ethyl 3-amino-3-[1-(4-chlorophenyl)cyclobutyl]acrylate.

A solution of ethyl 3-amino-3-[1-(4-chlorophenyl)cyclobutyl]acrylate (90 g), sodium cyanoborohydride (36 g), ammonium acetate (27 g) and acetic acid (60 ml) in ethanol (1.5 litres) was allowed to stand at room temperature for 5 days and then concentrated to 600 ml and poured into water (2.5 litres). The aqueous solution was basified, extracted with ether and the ether extract back extracted with 2N hydrochloric acid. The acidic aqueous extract was cooled with ice, basified and extracted with ether and the extract dried and evaporated to give ethyl 3-amino-3-[1-(4-chlorophenyl)cyclobutyl]propanoate.

A solution of ethyl 3-amino-3-[1-(4-chlorophenyl)cyclobutyl]propanoate (5.6 g) in ether (50 ml) was added over 30 minutes to a solution of ethylmagnesium bromide prepared by the addition of ethyl bromide (10 ml) to magnesium (2.9 g) and ether (80 ml). The mixture was stirred at ambient temperature for one hour and then heated under reflux for 30 minutes. 5N Hydrochloric acid (50 ml) was added and the mixture basified and extracted with ether. The extract yielded an oil which was distilled (185°–205° C./4 mm Hg). The distillate was dissolved in ether and a solution of oxalic acid in ether was added to precipitate 1-amino-1-[1-(4-chlorophenyl)cyclobutyl]-3-ethylpentan-3-ol hemioxalate (m.p. 181°–183° C. (dec)).

EXAMPLE 138

In a similar manner to that described in Example 137, except that ethyl 2-bromopropanoate was used instead of ethyl bromoacetate, 4-amino-4-[1-(4-chlorophenyl)-cyclobutyl]-2,3-dimethylbutan-2-ol oxalate (m.p. 166°–168° C. (dec)) was prepared.

EXAMPLE 139

A 0.25M solution of 3-[1-(ethoxy)ethoxy]propyllithium [prepared from 3-[1-(ethoxy)ethoxy]propyl bromide (20 g), lithium strips (1.6 g) and ether (75 ml)] was added to a solution of 1-(3,4-dichlorophenyl)cyclobutanecarbonitrile (4.44 g) in dry ether (100 ml) at 0° C. under argon. The mixture was stirred for 16 hours at ambient temperature and propan-2-ol (50 ml) and then a solution of sodium borohydride (1.5 g) in propan-2-ol (60 ml) were added and the mixture stirred at ambient temperature for 2 days and then heated under reflux for 2½ hours. The mixture was cooled, poured into water (500 ml) and excess concentrated hydrochloric acid was added. The mixture was heated at 90°–95° C. for one hour, cooled, basified and extracted with ether. The extract was dried and evaporated to give an oil which was treated with a further mixture of sodium borohydride (1 g) and propan-2-ol (50 ml) at reflux for 4½ hours. The mixture was cooled, and water was added and the resulting mixture extracted with ether. The extract was dried, and evaporated to give an oil which was distilled (170° C./0.65–0.25 mm Hg). The distillate was dissolved in propan-2-ol, 5N-hydrochloric acid was added and the solution evaporated to dryness. The residue was dried by azeotropic distillation with propan-2-ol to give a solid which was triturated with propan-2-ol to give 4-amino-4-[1-(3,4-dichlorophenyl)cyclobutyl]-butan-1-ol hydrochloride (m.p. 211° C. (dec)–shrinks 203° C.).

EXAMPLE 140

The product of Example 139 in the form of its free base (6.18 g), 37–40% aqueous formaldehyde solution (7.5 ml) and methanol (130 ml) were added to a 1N solution of sodium dihydrogen phosphite (107 ml prepared from phosphorous acid and sodium bicarbonate). The mixture was heated under reflux for 45 minutes and the methanol was then removed by evaporation. The residue was extracted into ether. The ether extract yielded 4-[1-(3,4-dichlorophenyl)cyclobutyl]-4-dimethylaminobutan-1-ol as an oil the boiling point of which was not determined.

Example 141

A solution of isopropylmagnesium chloride [prepared by the reaction of magnesium (2.4 g) and 2-chloropropane (10 ml) in tetrahydrofuran (30 ml)] was added dropwise under argon at −20° C. to a solution of 3-chloropropan-1-ol (9.45 g) in tetrahydrofuran (100 ml). Magnesium (3.6 g) was added and the mixture was allowed to stand for twenty minutes and was then heated under reflux in the presence of 1,2-dibromopropane for 40 minutes. 1-(4-Chlorophenyl)cyclobutanecarbonitrile (8 g) was added and the mixture was heated under reflux for 16 hours. The mixture was cooled and the supernatant liquid decanted from excess magnesium metal and treated with sodium borohydride (3 g) and propan-2-ol (100 ml). The mixture was heated under reflux for 5 hours. The reaction mixture was cooled, added to water and excess concentrated hydrochloric acid was added. The resulting solution was washed with toluene, basified and extracted with toluene. The extracts were dried and evaporated to give a residue which was distilled in a Buchi Kugelrohr apparatus (140°/0.4 mm) to give 4-amino-4-[1-(4-chlorophenyl)-cyclobutyl]butan-1-ol.

Example 142

A solution of 3-chloropropan-1-ol (95 ml) in tetrahydrofuran cooled to below −5° C. was added over 30 minutes to a solution of isopropylmagnesium chloride [prepared from magnesium (30 g), 2-chloropropane (100 ml) and tetrahydrofuran (300 ml)]. Magnesium (36 g) was added and the mixture warmed to initiate the reaction which then had to be cooled. Tetrahydrofuran (300 ml) was then added and the mixture heated under reflux for 30 minutes. 1-(4-Chlorophenyl)cyclobutane-carbonitrile (90 g) was added and the mixture heated under reflux for 16 hours and then cooled. Sodium borohydride (30 g) and then propan-2-ol (250 ml) were added and the mixture heated under reflux for 5 hours. The reaction mixture was poured into water (1 l), and acidified with excess concentrated hydrochloric acid. The resulting acidic mixture was extracted with toluene. Removal of the toluene gave a residue which was triturated with ether to give a solid which was dried, basified and extracted with ether. The ether was removed by evaportion to give a residue which was distilled (180°/1 mm to 172°/0.8 mm) to give 4-amino-4-[1-(4-chlorophenyl)cyclobutyl]butan-1-ol.

A mixture of 4-amino-4-[1-(4-chlorophenyl)cyclobutyl]-butan-1-ol, 37-40% aqueous formaldehyde solution (125 ml), 1N aqueous sodium dihydrogen phosphite solution (840 ml prepared from phosphorous acid and sodium bicarbonate) and methanol (1500 ml) was heated under reflux for 2½ hours. The methanol was then removed by evaporation and the aqueous residue was basified to yield 4-[1-(4-chlorophenyl)cyclobutyl]-4-dimethylaminobutan-1-ol as an oil the boiling point of which was not determined.

EXAMPLE 143

An ice-cold stirred solution of ethylmagnesium bromide [from ethyl bromide (9 ml) and magnesium (3 g)] in dry ether (50 ml) was treated dropwise at 0° C. under nitrogen with an ice-cold solution of 3-buten-1-ol (3.69 g) and titanocene dichloride (0.05 g) in dry tetrahydrofuran (100 ml). The mixture was heated under reflux for 20 hours and 1-(4-chlorophenyl)cyclobutanecarbonitrile (5 g) was then added. The mixture was heated under reflux for 8 hours, allowed to stand at room temperature for 16 hours and added to a slurry of sodium borohydride (5 g) in propan-2-ol (500 ml). The mixture heated under reflux for 24 hours. The solvent was removed in vacuo and the residue was diluted with water. The product was extracted into ethyl acetate, and the extracts were washed, dried and evaporated. The resultant oil was taken up in ether and treated with a solution of maleic acid (3 g) in ether, to give a sticky white gum which solidified to give 5-amino-5-[1-(4-chlorophenyl)-cyclobutyl]pentan-1-ol maleate (m.p. 58°-60° C.).

EXAMPLE 144

A stirred solution of disodium hydrogen phosphite pentahydrate (14.1 g) in water (71 ml) was treated successively with 5M hydrochloric acid (10.7 ml), a solution of the product of Example 143 in the form of its free base (3.5 g) in tetrahydrofuran (100 ml) and 37-40% aqueous formaldehyde solution (10 ml). The mixture was heated under reflux for 5 hours, cooled and extracted with ether. The washed and dried extracts were evaporated to give 5-[1-(4-chlorophenyl)cyclobutyl]-5-dimethylaminopentan-1-ol as an oil the boiling point of which was not determined.

EXAMPLE 145

A mixture of the product of Example 144 (1.55 g), ethyl acetate (100 ml) and acetic anhydride (20 ml) was heated under reflux for 16 hours, cooled and poured into water. The resulting mixture was basified and extracted with ether. The extract was washed, dried and evaporated to give an oil which was purified by flash chromatography on a silica column using a 9:1 mixture of petroleum ether (b.p. 60°-80° C.) and acetone and then acetone as eluant to give 5-[1-(4-chlorophenyl)cyclobutyl]-5-dimethylaminopentyl acetate as an oil the boiling point of which was not determined.

EXAMPLE 146

Methoxyacetyl chloride was added dropwise to a solution of the product of Example 144 and triethylamine in ether and the mixture stirred for 24 hours and then poured into ice-cold aqueous sodium hydroxide solution. The mixture was extracted with ether and the extract washed, dried and evaporated to give an oil, which was purified by flash chromatography on a silica column using ether as eluant to give 5-[1-(4-chlorophenyl)cyclobutyl]-5-dimethylaminopentyl 2-methoxyacetate as an oil the boiling point of which was not determined.

EXAMPLE 147

A solution 1-(6-chlorohexyloxy)-1-ethoxyethane (18.4 g) and bromoethane (9.6 g) in dry ether (80 ml) was added under argon to a stirred mixture of magnesium (9.0 g) and ether (20 ml) at such a rate that a gentle reflux was maintained. A solution of 1-(3,4-dichlorophenyl)cyclobutanecarbonitrile (27.1 g) in dry ether (50 ml) was added and the mixture stirred for 16 hours. A solution of sodium borohydride (8 g) in propan-2-ol (150 ml) was added and the mixture heated under reflux for four hours. The mixture was then cooled, added to water (500 ml) and excess concentrated hydrochloric acid added. The mixture was washed with dichloromethane and the aqueous layer basified and extracted with ether. The extracts were washed, dried and evaporated to give an oil. Volatile components of the oil were removed at 130° C./0.2 mm Hg. The residue was dissolved in ether and a warmed solution of fumaric acid in ethanol was added to give 7-amino-7-[1-(3,4dichlorophenyl)cyclobutyl]heptan-1-ol hemifumarate (m.p. 159°-160° C.).

EXAMPLE 148

1-(3,4-Dichlorophenyl)cyclobutanecarbonitrile (13 g) was added to a solution of 3-butenylmagnesium bromide [prepared from 4-bromobut-1-ene (10.6 g), magnesium (2 g) and ether (65 ml)]. The ether was replaced by toluene (60 ml) and the mixture heated for 2½ hours. The mixture was then added to a solution of sodium borohydride (4.4 g) in ethanol (200 ml). The mixture was heated under reflux for one hour, cooled, added to water and the resulting mixture extracted with ether. The extract yielded 1-[1-(3,4-dichlorophenyl)cyclobutyl]pent-4-enylamine as an oil. This oil was added to a 1N solution of sodium dihydrogen phosphite [287 ml—prepared by mixing a solution of phosphorous acid (41 g) in water (100 ml) with sodium bicarbonate (42 g) and making the resulting solution up to 500 ml with water]. Methanol (350 ml) and 37-40% aqueous formaldehyde (25 ml) were added and the mixture heated under reflux for 1½ hours and was then allowed to stand for 2½ days. The methanol was removed by evaporation and the aqueous residue extracted with ether. The ether extract yielded an oil which was dissolved in ether. The solution was filtered and treated with an ethereal solution of maleic acid. An oil formed which was triturated with ether to give a semi-solid which was basified to give a N,N-dimethyl-1-[1-(3,4-dichlorophenyl)cyclobutyl]pent-4-enylamine.

A solution of osmium tetroxide (2 g) in pyridine (10 ml) was added with stirring to a solution of N,N-dimethyl-1-[1-(3,4-dichlorophenyl)cyclobutyl]pent-4-enylamine (2.43 g) in pyridine (20 ml). The mixture was allowed to stand for one and three quarter hours and was then added to a mixture of pyridine (40 ml) and a solution of sodium bisulphite (3.6 g) in water (60 ml). The resulting aqueous layer was extracted with dichloromethane and the extracts washed, dried and evaporated in vacuo to give a residue which was purified by flash chromatography using ether as eluant to give 5-[1-(3,4-dichlorophenyl)cyclobutyl]-5-dimethylaminopentane-1,2-diol the boiling point of which was not determined.

EXAMPLES 149 TO 173

Compounds of formula I in which $R_1$ and $R_2$ are H (listed in Table VI) were prepared from carbonitriles of formula XV by one of the following general reaction methods which are listed in the column headed M in Table VI.

Method A

A mixture of a halomagnesium compound of formula $R_4MgX$, a carbonitrile of formula XV and ether was heated under reflux under a blanket of nitrogen for R hours. The resulting solid imine was filtered off and then reduced by adding the solid imine portionwise to a mixture of sodium borohydride and solvent S (1=ethanol and 2=propan-2-ol) and heating under reflux for T hours.

Method B

A mixture of a halomagnesium compound of formula $R_4MgX$, a solution of a carbonitrile of formula XV and ether was heated under reflux under a blanket of nitrogen for R hours. The resulting imine was not isolated but was reduced directly by adding a mixture of sodium borohydride and solvent S and heating under reflux for T hours.

Method C

As method A except that the halomagnesium compound and the carbonitrile were reacted in tetrahydrofuran.

Method D

As method B except that the halomagnesium compound and the carbonitrile were reacted in tetrahydrofuran.

Method E

As method C except that the tetrahydrofuran was evaporated after the reaction of the halomagnesium compound and the carbonitrile to give a melt which was heated at 95°-97° C. for 10 minutes and cooled. Ether was added and a solid collected by filtration and reduced as described in Method A.

Method F

As method A except that the mixture of the halomagnesium compound, the carbonitrile and the ether was stirred at ambient temperature for R hours.

Method G

As method B except that the mixture of the halomagnesium compound, the carbonitrile and the ether was stirred at ambient temperature for R hours.

The desired product was then isolated by one of the methods described below and identified by number in the column headed PM. Where two methods are given, they were applied sequentially in the order given and the melting point or boiling point given in the last column applies to the last method given. For example if the last method involves salt formation the last column contains the melting point of the salt.

(1) by hydrochloride salt formation
(2) by distillation on a Buchi Kugelrohr apparatus—the operating temperature given in the final column
(3) by high performance liquid chromatography—an oil was obtained, the boiling point of which was not determined
(4) by maleate salt formation
(5) by distillation
(6) the final product was obtained as an oil, the boiling point of which was not determined
(7) by oxalate salt formation
(8) by fumarate salt formation
(9) by citrate salt formation
(10) by flash chromatography using the following eluants: a 9:1 mixture of ether and methanol (10a), ether (10b), a 9:1 mixture of petroleum ether (b.p. 40°-60° C.) and acetone (10c), a 9:1 mixture of petroleum ether (b.p. 80°-100° C.) and acetone (10d) and a 9:1 mixture of petroleum ether (b.p. 40°-60° C.) and ethyl acetate (10e)
(11) attempted purification by flash chromatography using a 9:1 mixture of petroleum ether (b.p. 40°-60° C.) and acetone gave an oil containing what was believed to be an imine formed by reaction of the desired product with the acetone. A mixture of the oil, tetrahydrofuran and concentrated hydrochloric acid was allowed to stand at ambient temperature for 16 hours to hydrolyse the imine to give the desired primary amine

TABLE VI

| Ex. | $R_3$ | $R_4$ | M | X | R | S | T | PM | mp/bp |
|---|---|---|---|---|---|---|---|---|---|
| 149 | 4-chlorophenyl | $(CH_2)_3OMe$ | D | Cl | 2 | 1 | 0.5 | (1) | 68° C. |
| 150 | 4-chlorophenyl | $(CH_2)_3OEt$ | D | Cl | 3 | 1 | 0.67 | (2) | 180° C./0.5 mm Hg |
| 151 | 4-chlorophenyl | $(CH_2)_3OPr$ | D | Br | 48 | 2 | 96 | (5)(10a) | |
| 152 | 4-chlorophenyl | $(CH_2)_3OPr^i$ | D | Br | 6 | 2 | 72 | (5)(4) | 123-124° C. |
| 153 | 4-chlorophenyl | $(CH_2)_2CH(OMe)Me$ | D | Br | 27 | 2 | 72 | (5)(10b) | |
| 154 | 4-chlorophenyl | $CH_2CHMeCH_2OMe$ | D | Cl | 18 | 2 | 5 | (5)(4)(10a) | |
| 155 | 4-chlorophenyl | $CH_2CHEtCH_2OMe$ | F | Cl | 18 | 2 | 7 | (9) | 159-160° C. |
| 156 | 3,4-dichlorophenyl | $(CH_2)_3OMe$ | D | Br | 5 | 1 | 0.5 | (5)(4) | 109-110° C. |
| 157 | 4-tolyl | $(CH_2)_3OMe$ | D | Br | 5 | 1 | 0.5 | (5)(4) | 118-119° C. |
| 158 | 3-trifluoromethyl phenyl | $(CH_2)_3OMe$ | D | Br | 5 | 1 | 0.5 | (5)(4) | 107-108° C. |
| 159 | 2-naphthyl | $(CH_2)_3OMe$ | D | Br | 5 | 1 | 0.5 | (5)(4) | 119-120° C. |
| 160 | 4-bromophenyl | $(CH_2)_3OMe$ | F | Br | 18 | 2 | 3 | (4) | 125-126° C. |
| 161 | 3-trifluoromethyl phenyl | $(CH_2)_3OPr$ | F | Br | 18 | 2 | 7 | (11) | |
| 162 | 3-trifluoromethyl phenyl | $(CH_2)_3OPr^i$ | G | Br | 18 | 2 | 6 | (9) | 135.5-137° C. |
| 163 | 3,4-dichlorophenyl | $(CH_2)_3OCMe_2Et$ | G | Br | 18 | 2 | 24 | (7)(6) | |
| 164 | 3,4-dichlorophenyl | $(CH_2)_3O(CH_2)_5Me$ | D | Br | 24 | 2 | 72 | (3) | |
| 165 | 4-chlorophenyl | $(CH_2)_3O(CH_2)_2OMe$ | E | Br | 2 | 1 | 1 | (4) | 106-108° C. |
| 166 | 3,4-dichlorophenyl | $(CH_2)_2CH(OMe)Me$ | G | Br | 4 | 1 | 4 | (7) | 174-175° C. |
| 167 | 3,4-dichlorophenyl | $(CH_2)_6OMe$ | D | Br | 5 | 1 | 0.5 | (5)(4) | 123-125° C. |

TABLE VI-continued

| Ex. | R₃ | R₄ | M | X | R | S | T | PM | mp/bp |
|---|---|---|---|---|---|---|---|---|---|
| 168 | 3,4-dichlorophenyl | (CH₂)₃O(CH₂)₂OMe | C | Br | 0.5 | 2 | 3 | (4) | 130–131° C. |
| 169 | 3,4-dichlorophenyl | (CH₂)₃Ocyclopentyl | G | Br | 18 | 2 | 5 | (2)(8) | 157–159° C. |
| 170 | 3,4-dichlorophenyl | (CH₂)₃SMe | B | Cl | 0.5 | 1 | 1 | (4) | 113–114° C. |
| 171 | 4-methylthiophenyl | CH₂CHMeCH₂OMe | B | Cl | 24 |  | 20 | (6) |  |
| 172 | 3-trifluoromethylphenyl | CH₂CHMeCH₂OMe | F | Cl | 18 | 2 | 6 | (6) |  |
| 173 | 3,4-dichlorophenyl | (CH₂)₃O(CH₂)₂cyclohexyl | A | Br | 1 | 2 | 2 | (6) |  |

EXAMPLES 174 TO 189

Primary amines of formula I in which $NR_1R_2$ is $NH_2$ prepared as described in the Examples identified in Table VII were converted into the corresponding N,N-dimethyl compounds of formula I in which $NR_1R_2$ is $NMe_2$ by one of the following reaction methods which are identified in column N of Table VII.

Method K

The primary amine in the form of its free base was heated under reflux with a mixture of 37–40% aqueous formaldehyde and 98% formic acid for sufficient time to complete the reaction.

Method L

The primary amine in the form of a salt was heated under reflux with a mixture of sodium formate, 98% formic acid and 37–40% aqueous formaldehyde solution for sufficient time to complete the reaction. The products obtained are listed in Table VII.

The products were isolated by the method identified by number in the column headed P which have the same meaning as in Table VI The column headed SM gives the Example number of the primary amine used in the synthesis.

TABLE VII

| Ex. | R₃ | R₄ | SM | N | PM | mp/bp |
|---|---|---|---|---|---|---|
| 174 | 4-chlorophenyl | (CH₂)₃OMe | 149 | K | (1) | 162–163° C. |
| 175 | 4-chlorophenyl | (CH₂)₃OEt | 150 | K | (7) | 130–132° C. |
| 176 | 4-chlorophenyl | (CH₂)₃OPr | 151 | K | (10c) |  |
| 177 | 4-chlorophenyl | (CH₂)₃OPrⁱ | 152 | K | (6) |  |
| 178 | 4-chlorophenyl | (CH₂)₂CH(OMe)Me | 153 | K | (6) |  |
| 179 | 4-chlorophenyl | CH₂CHMeCH₂OMe | 154 | K | (6) |  |
| 180 | 4-chlorophenyl | CH₂CHEtCH₂OMe | 155 | L | (9) | 130–133° C. |
| 181 | 3,4-dichlorophenyl | (CH₂)₃OMe | 156 | K | (4) | 96–97° C. |
| 182 | 3-trifluoromethyl phenyl | (CH₂)₃OMe | 158 | K | (4) | 117–118° C. |
| 183 | 4-bromophenyl | (CH₂)₃OMe | 160 | L | (1) | 170–171° C. |
| 184 | 3-trifluoromethyl phenyl | (CH₂)₃OPr | 161 | K | (6) |  |
| 185 | 3,4-dichlorophenyl | (CH₂)₃O(CH₂)₅Me | 164 | K | (6) |  |
| 186 | 3,4-dichlorophenyl | (CH₂)₃O(CH₂)₂OMe | 165 | K | (2) | 200° C./0.2 mm Hg |
| 187 | 3,4-dichlorophenyl | (CH₂)₃SMe | 170 | K | (4) | 114–116° C. |
| 188 | 3-trifluoromethylphenyl | (CH₂)₃OPrⁱ | 162 | L | (10d) |  |
| 189 | 3-trifluoromethylphenyl | CH₂CHMeCH₂OMe | 172 | L | (6) |  |

EXAMPLES 190 TO 195

In a similar manner to that described in Examples 149 to 173, compounds of formula I in which $NR_1R_2$ is $NH_2$ were prepared by the method identified in the column headed M in Table VIII and then converted into compounds of formula I in which $NR_1R_2$ is $NMe_2$ by the method identified in the column headed N in Table VIII. The resulting compounds are listed in Table VIII. The notes in the column headed X, R, S, T and PM have the same meaning as in Table VI.

TABLE VIII

| Ex. | R₃ | R₄ | M | X | R | S | T | N | PM | mp/bp |
|---|---|---|---|---|---|---|---|---|---|---|
| 190 | 4-chlorophenyl | (CH₂)₃Ocyclopentyl | B | Br | 6 | 2 | 20 | L | (6) |  |
| 191 | 4-chlorophenyl | (CH₂)₄OMe | D | Cl | 3 | 1 | 0.67 | K | (1) | 155–157° C. |
| 192 | 2-fluorophenyl | (CH₂)₃OMe | D | Br | 3.25 | 1 | 0.5 | K | (5)(4) | 91–92° C. |
| 193 | 4-chlorophenyl | (CH₂)₃O(CH₂)₇Me | F | Br | 18 | 2 | 20 | K | (6) |  |
| 194 | 3,4-dichlorophenyl | (CH₂)₃O(CH₂)₇Me | F | Br | 18 | 2 | 20 | K | (2)(10e) |  |
| 195 | 3,4-dichlorophenyl | (CH₂)₈OMe | A | Br | 18 | 2 | 2 | K | (2) | 200° C./0.1 mm Hg |

EXAMPLE 196

5N Hydrochloric acid (4.95 ml), a solution of the product of Example 163 (1.77 g) in tetrahydrofuran (40 ml) and 37–40% aqueous formaldehyde solution (5 ml) were added successively to a stirred solution of disodium hydrogenphosphite pentahydrate (5.35 g) in water (30 ml). The mixture was heated under reflux for 16 hours and then cooled and extracted with ether. The extracts were washed, dried and evaporated to leave an oil which was purified by chromatography on a silica column using a 9:1 mixture of petroleum ether (b.p. 60–80° C.) and acetone as eluant. Evaporation of the eluate gave N,N-dimethyl-1-[1-(3,4-dichlorophenyl)cyclobutyl]-4-(1,1-dimethylpropoxy)butylamine as an oil the boiling point of which was not determined.

EXAMPLE 197

The product of Example 150 (2.5 g) was dissolved in methyl formate (25 ml) and left to stand at ambient temperature for 5 days. The solvent was then removed by evaporation to give an oil (2.75 g) which was triturated with petroleum ether (b.p. 40°–60° C.) to give N-formyl-1-[1-(4-chlorophenyl)cyclobutyl]-4-ethoxybutylamine (m.p. 58°–59° C.).

A solution of N-formyl-1-[1-(4-chlorophenyl)-cyclobutyl]-4-ethoxybutylamine (1.6 g) in dry toluene (40 ml) was added dropwise to a stirred 70% solution of sodium bis-(2-methoxyethoxy)aluminium hydride in toluene sold under the trade name Red-Al (6 ml) in dry toluene (15 ml) at ambient temperature, under nitrogen. The mixture was stirred at 50° C. for 3 hours then cooled and water (20 ml) and then 5N sodium hydroxide solution (15 ml) were added. The mixture was extracted with ether and the extracts dried and evaporated to give an oil which was treated with an ethereal solution of maleic acid to give a salt which was recrystallised from propan-2-ol to give N-methyl-1-[1-(4-chlorophenyl)cyclobutyl)-4-ethoxybutylamine maleate (m.p. 102–103° C.).

EXAMPLE 198

A mixture of the product of Example 156 (2 g), 1,4-dibromobutane (0.79 ml), anhydrous sodium carbonate (1.6 g) and dry xylene (20 ml) was heated under reflux with stirring for 18 hours. Further portions of anhydrous sodium carbonate (0.8 g) and 1,4-dibromobutane (0.4 ml) were added and the mixture heated under reflux for 20 hours and then cooled and filtered through diatomaceous earth (trade name Celite). The diatomaceous earth was washed with ether. The filtrate and washings were combined and extracted with 5N hydrochloric acid. The acid extracts were washed with ether, basified and extracted with ether. The extract was washed with water, dried and evaporated to yield an oil which was distilled using a Buchi Kugelrohr apparatus (160°–170° C./0.4 mm). The distillate was purified by flash chromatography using a 9:1 mixture of petroleum ether (b.p. 40°–60° C.) and triethylamine as eluant to give N-{1-[1-(3,4-dichlorophenyl)cyclobutyl]-4-methoxy-butyl}pyrrolidine as an oil the boiling point of which was not determined.

EXAMPLE 199

A mixture of 1-[1-(4-chlorophenyl)cyclobutyl]-5-methoxypentylamine [1.7 g prepared in a similar manner to that described in method D hereinbefore (X=Cl, R=3, S=1, T=0.67)] and methyl formate (20 ml) was allowed to stand at ambient temperature for 7 days. The mixture was then filtered to remove a colourless solid which was discarded. The filtrate was evaporated and the residue was dissolved in dry toluene (29 ml). The solution was added dropwise to a 70% solution of bis-(2-methoxyethoxy)aluminium hydride in toluene sold under the trade name Red-Al (4.3 ml) in dry toluene (11 ml) under nitrogen and then the reaction mixture was heated at 50° C. with stirring for 3 hours. The reaction mixture was cooled, and water (20 ml) and 5N sodium hydroxide (15 ml) were added. The aqueous layer was separated and extracted with ether and the extracts combined with the toluene solution, washed with water, dried, filtered and evaporated to give an oil which was dissolved in ether. A solution of maleic acid (0.33 g) in ether was added to give a solid which was recrystallised from propan-2-ol to give N-methyl-1-[1-(4-chlorophenyl)cyclobutyl]-5-methoxypentylamine maleate (m.p. 94°–95° C.).

EXAMPLE 200

In a similar manner to that described in Example 199, N-methyl-1-[1-(4-chlorophenyl)cyclobutyl]-5ethoxypentylamine maleate (m.p. 67°–68° C.) was prepared.

EXAMPLE 20

A solution of propionyl chloride (0.73 g) in dry ether (5 ml) was added dropwise to a stirred mixture of the product of Example 156 (3 g) and triethylamine (4 ml) in dry ether (20 ml) at 5°–10° C. The mixture was stirred at ambient temperature for 16 hours and then filtered. The filtrate was evaporated in vacuo to give a gum which was triturated with cold petroleum ether (b.p. 40°–60° C.) to give a cream solid. Boranedimethylsulphide complex (2 ml) was added dropwise from a syringe to a stirred mixture of the solid (1.63 g) and dry tetrahydrofuran (25 ml) at reflux under nitrogen. The mixture was heated under reflux for 2 hours, allowed to stand at ambient temperature for 16 hours and then evaporated to half volume. The remainder was cooled in ice and 5N hydrochloric acid (50 ml) was added and the mixture stirred at ambient temperature for 2 hours. The mixture was then washed with ether, basified with 16N aqueous sodium hydroxide solution and extracted with ether. The extract was dried and evaporated to give N-propyl-1-[1-(3,4-dichlorophenyl)-cyclobutyl]-4-methoxybutylamine as an oil the boiling point of which was not determined.

EXAMPLES 202 TO 205

In a similar manner to that described in Example 201 the product of Example 156, either in the form of its maleate salt (Examples 202 and 203) or in the form of its free base (Examples 204 and 205), was reacted with the appropriate acid chloride and the resulting amide was reduced to give the compounds of formula I in which $R_2$ is H, $R_3$ is 3,4-dichlorophenyl and $R_4$ is 3-methoxypropyl which are listed in Table IX. The notes have the meaning given in respect of Table VI.

TABLE IX

| Ex. | $R_1$ | Notes | |
|-----|-------|-------|---|
| 202 | i-Bu | (6) | |
| 203 | $(CH_2)_2OMe$ | (6) | |
| 204 | $CH_2Ph$ | (1) | 159–166° C. |
| 205 | cyclopropylmethyl | (4) | 104–107° C. |

EXAMPLE 206

A solution of bromine (8 ml) in dichloromethane (40 ml) was added at 10° C. to a solution of 1-[1-(4-chlorophenyl)cyclobutyl]ethanone (27.8 g) in methanol (30 ml). The mixture was stirred for 15 minutes and poured into a mixture of ice and water. The resulting mixture was extracted with dichloromethane. The extract was washed with water, dried and evaporated to yield an oil which was distilled (145°–160° C./1mm Hg) to give 1-[1-(4-chlorophenyl)cyclobutyl]-2-bromoethanone.

A solution of 1-[1-(4-chlorophenyl)cyclobutyl]-2-bromoethanone (3 g) in methanol (10 ml) was added to sodium methoxide prepared by the reaction of sodium (0.46 g) and methanol (20 ml) and the mixture was stirred for two hours, and then poured into water. The aqueous mixture was extracted with ether and the extract dried and evaporated to give 2-[1-(4-chlorophenyl)cyclobutyl]-2,2-dimethoxyethanol (m.p. 73°–74° C.).

2-[1-(4-Chlorophenyl)cyclobutyl]-2,2-dimethoxyethanol (1.48 g) and then methyl iodide (1.86 g) were added to a mixture of powdered potassium hydroxide (1.23 g) and dry dimethylsulphoxide (10 ml) which had been stirred for 5 minutes. The mixture was stirred for 30 minutes and was then poured into water (100 ml). The resulting mixture was acidified with concentrated sulphuric acid and extracted with dichloromethane. The extract was washed with water and dried and then evaporated to give 1-[1-(4-chlorophenyl)cyclobutyl]-2methoxyethanone as an oil.

Sodium cyanoborohydride (4 g) was added to a stirred mixture of 1-[1-(4-chlorophenyl)cyclobutyl]-2methoxyethanone (20 g), ammonium acetate (70 g) and methanol (300 ml) and the mixture allowed to stand at ambient temperature for 10 days. The mixture was poured into water (1 litre), basified with aqueous sodium carbonate solution and extracted with ether. The extract was evaporated to yield an oil which was poured into water, acidified with concentrated sulphuric acid and allowed to stand for 16 hours at ambient temperature and then heated to 90°-95° C. for 1 hour. The cooled mixture was washed with ether, basified and extracted with ether. The extracts were dried and evaporated to give an oil which was treated with concentrated hydrochloric acid and propan-2-ol. Evaporation to dryness gave a solid which was recrystallised from propan-2-ol to give 1-[1-(4-chlorophenyl)cyclobutyl]-2-methoxyethylamine hydrochloride (m.p. 207°-210° C.).

EXAMPLE 207

In a similar manner to that described hereinbefore as Method K in Examples 174 to 189 the product of Example 206 was converted into N,N-dimethyl-1-[1-(4-chlorophenyl)cyclobutyl]-2-methoxyethylamine hydrochloride (m.p. 179°-181° C.) which was recrystallised twice from propan-2-ol.

EXAMPLE 208

2-(Morpholino)ethylamine (20 g) was heated at 175°-180° C. and 1-(4-chlorophenyl)cyclobutyl-2-methoxyethanone (20 g) prepared as described in Example 206 was added dropwise with stirring over 1 hour. The mixture was stirred at 180° C. for a further hour. A stream of nitrogen was passed through the reaction mixture to remove any water formed. The mixture was cooled and added dropwise to a suspension of sodium borohydride (10 g) in propan-2-ol (800 ml). The mixture was then heated under reflux for 3 hours. Propan-2-ol was evaporated and an ice/water mixture was added to the residue which was cooled and acidified with 5N hydrochloric acid. The acidified mixture was basified and extracted with ether Hydrogen chloride gas was passed into the dried extract which was then evaporated to dryness. The residue was heated with propan-2-ol, filtered and the filtrate evaporated to dryness. The residue was partitioned between ether and 2N hydrochloric acid. The acid layer was washed with ether, basified and extracted with ether. Hydrogen chloride gas was passed into the ether extract which was then evaporated to dryness to give a residue which was recrystallised from propan-2-ol to give N-(2-morpholinoethyl)-1-[1-(4-chlorophenyl)cyclobutyl]-2-methoxyethylamine dihydrochloride (m.p. 234°-237° C.).

EXAMPLE 209

A mixture of the product of Example 208 in the form of its free base (2.0 g), 98% formic acid (8 ml) and 37-40% aqueous formaldehyde solution (25 ml) was stirred at room temperature for 2 hours. The mixture was then heated at 95°-100° C. for 18 hours, cooled, basified and extracted with ether. The extract was washed with water and dried. Dry hydrogen chloride gas was passed into the ethereal solution. Evaporation of the solvent gave a residue which was heated with ethyl acetate (20 ml) to give a white solid which was partitioned between ether and water. The aqueous phase was basified and then extracted with ether. The extract was dried and evaporated to give a residue which was distilled using a Buchi Kugelrohr apparatus (200° C./0.5 mm) to give N-methyl-N-(2-morpholinoethyl)-1-[1-(4-chlorophenyl)cyclobutyl]-2-methoxyethylamine.

EXAMPLE 210

A solution of 2-[1-(4-chlorophenyl)cyclobutyl]-2-dimethylaminoacetonitrile (4.7 g prepared as described in Example A) in dry tetrahydrofuran (20 ml) was added at −20° C. to lithium diisopropylamide [prepared by adding a solution of diisopropylamine (2.02 g) in dry tetrahydrofuran (30 ml) to a 2.7M solution of butyllithium in hexane (7.5 ml) at −10° C.]. Formaldehyde vapour produced by heating paraformaldehyde to 180° C. was passed into the resulting solution at −50° C. until the colour changed from red-brown to pale yellow. Methanol (50 ml) was added and sodium borohydride (6 g) added portionwise with stirring. Stirring was continued for 3 days and then water (50 ml) and excess dilute hydrochloric acid were added. Methanol was removed by evaporation in vacuo to leave a solution which was basified and extracted with ether. Removal of the ether after drying yielded an oil which was dissolved in 5N hydrochloric acid (8 ml) and water (50 ml). The solution was evaporated and the residue dried by azeotropic distillation with propan-2-ol. The residue was crystallised from acetone to give 2-[1-(4-chlorophenyl)cyclobutyl]-2-dimethylaminoethanol hydrochloride (m.p. 230°-231° C.). A solution of this compound in the form of its free base (1.01 g) in dry tetrahydrofuran (10 ml) was added dropwise to a stirred mixture of sodium hydride (0.35 g, 50% suspension in mineral oil) and dry tetrahydrofuran (10 ml) under nitrogen. Stirring was continued until hydrogen evolution had ceased and the mixture was heated at 40°-45° C. for 20 minutes. After cooling to 20° C. a solution of iodomethane (0.6 g) in dry tetrahydrofuran (5 ml) was added and the mixture heated under reflux for two hours. Water (20 ml) was added dropwise to the cooled reaction mixture which was then extracted with ether and the extract washed with water. The ether extract was dried and evaporated and the residue was dissolved in propan-2-ol (15 ml). Concentrated hydrochloric acid (2 ml) was added and the mixture evaporated to dryness to give a solid which was recrystallised from ethyl acetate to give N,N-dimethyl-1-[1-(4-chlorophenyl)cyclobutyl]-2-methoxyethylamine hydrochloride (m.p. 180°-185° C.).

EXAMPLE 211

A solution of ethyl 3-amino-3-[1-(4-chlorophenyl)cyclobutyl]propanoate (5 g prepared as described in Example 137) in ether (25 ml) was added dropwise to a stirred suspension of lithium aluminium hydride (3 g) in ether (50 ml). The mixture was heated under reflux for 3 hours, allowed to stand for 16 hours with no heating and then heated under reflux for a further 6 hours. Water (3 ml) was added dropwise with stirring to the cooled reaction mixture followed by 15% aqueous sodium hydroxide solution (3 ml) and water (9 ml). The reaction mixture was filtered and the residue washed with ether. The filtrate and the washings were combined, washed with water then brine and dried. Evaporation of the solvent gave a residue which was recrystallised from petroleum ether (b.p. 40°-60° C.) to give 3-amino-3-[1-(4-chlorophenyl)cyclobutyl]propan-1-ol (m.p. 98°-99° C.).

In a similar manner to that described hereinbefore as Method K in Examples 174 to 189, 3-amino-3-[1-(4-chlorophenyl)cyclobutyl]propan-1-ol· was converted into 3-[1-(4-chlorophenyl)cyclobutyl]-3-dimethylaminopropan-1-ol hydrochloride [m.p. 220°-223° C. (dec)].

A solution of 3-[1-(4-chlorophenyl)cyclobutyl]-3-dimethylaminopropan-1-ol (7.8 g) in dichloromethane (150 ml) and dimethylformamide (4 ml) was treated at 0° C. with a solution of thionyl chloride (14 ml) in dichloromethane (7 ml). The mixture was stirred at room temperature for 45 minutes, then heated at reflux for 15 hours, cooled, poured into water and washed with dichloromethane. The aqueous phase was basified and extracted with ether. The extract was evaporated and the residue was dissolved in methanol (50 ml) and treated with sodium methoxide (1 g). The solution was heated under reflux for 17 hours and then concentrated to about 10 ml and diluted with water to 150 ml. The aqueous solution was extracted with ether and the extracts back-extracted with 3N hydrochloric acid. The acidic extracts were basified and extracted with ether. The ethereal extracts were dried and evaporated to give an oil which was mixed with petroleum ether (b.p. 40-60) (20 ml). The resulting mixture was filtered and evaporated to give N,N-dimethyl-1-[1-(4-chlorophenyl)cyclobutyl]-3-methoxypropylamine as an oil the boiling point of which was not determined.

EXAMPLE 212

A solution of 3-[1-(4-chlorophenyl)cyclobutyl]-3-dimethylaminopropan-1-ol (3 g prepared as described in Example 211) in tetrahydrofuran (50 ml) was added to a stirred suspension of sodium hydride (1.02 g of a 50% dispersion in mineral oil) in tetrahydrofuran (60 ml). The mixture was stirred at ambient temperature for one hour and a solution of 4-vinylpyridine (5.74 ml) in tetrahydrofuran (10 ml) was added and the mixture allowed to stand for 72 hours at ambient temperature and then heated under reflux for 48 hours. Water was added dropwise to the cooled reaction mixture which was then extracted with ether. The extracts were washed, dried and evaporated to give an oil which was dissolved in ether, filtered and the filtrate evaporated. The residue was heated at 95° C./0.5 mm Hg for 2 hours and then purified by flash chromatography on a silica column using a 9:1 mixture of light petroleum (b.p. 60°-80° C.) and propan-2-ol as eluant followed by high performance liquid chromatography. The product was heated at 80° C./20 mm Hg for 5 hours to leave N,N-dimethyl-1-[1-(4-chlorophenyl)cyclobutyl]-4-[2-(4-pyridyl)ethoxy]butylamine as an oil the boiling point of which was not determined.

EXAMPLE 213

A solution of the product of Example 142 (14.1 g) in tetrahydrofuran (30 ml) was added dropwise to a stirred suspension of sodium hydride (2.4 g of a 50% dispersion in mineral oil) in tetrahydrofuran (50 ml). The mixture was stirred at ambient temperature for 1½ hours and cooled to 10° C. A solution of chloroacetylmorpholine (8.15 g) in tetrahydrofuran (30 ml) was added and the mixture stirred for 16 hours at 20°-25° C. The mixture was allowed to stand for 24 hours and was then poured into water. The aqueous mixture was extracted with ether. The extract was washed, dried and evaporated to give a residue which was purified by flash chromatography using ether as eluant to give an oil which was crystallised from petroleum ether (bp 60°-80° C.) to give 2-{4-[1-(4-chlorophenyl)cyclobutyl]-4-dimethylaminobutoxy}-N,N-3-oxapentamethyleneacetamide (mp 92°-94° C.).

EXAMPLE 214

A solution of the product of Example 142 (28.1 g) in tetrahydrofuran (60 ml) was added under argon to a stirred suspension of sodium hydride (5.04 g of a 50% dispersion in mineral oil) in tetrahydrofuran (30 ml) at <30° C. After 45 minutes dimethylformamide (10 ml) was added the mixture stirred for 16 hours at ambient temperature. The mixture was cooled to below 10° C. and a solution of chloroacetylmorpholine (18 g) in tetrahydrofuran (60 ml) added. The mixture was then stirred at ambient temperature for 2½ days and then poured into water. The aqueous mixture was extracted with ether and the extract dried and evaporated to give a residue which was distilled. The residue after distillation was dissolved in hot petroleum ether (bp 80° to 100° C.), treated with charcoal, filtered and cooled. The supernatant was decanted from an oily residue and evaporated to give an oil which was distilled on a Buchi Kugelrohr apparatus (140°/0.2 mm) leaving 2-{4-[1-(4-chlorophenyl)cyclobutyl]-4-dimethylaminobutoxy}-N,N-3-oxapentamethyleneacetamethyleneacetamide as the residue. A solution of this product (4.18 g) in ether (20 ml) was added dropwise over 15 minutes under argon to a stirred mixture of ether (10 ml) and a 1.55M solution of methyllithium in ether (7 ml) at −20° to −25° C. The mixture was stirred for 3 hours at ambient temperature and then cooled to below −20° C. and a saturated aqueous solution of ammonium chloride (40 ml) was added. The ether phase was separated, dried and evaporated to give an oil which was purified by flash chromatography using ether as the eluant to give 1-{4-[1-(4-chlorophenyl)cyclobutyl]-4-dimethylaminobutoxy}propan-2-one as an oil the boiling point of which was not determined.

EXAMPLE 215

A mixture of 1-{4-[1-(4-chlorophenyl)cyclobutyl]-4-dimethylaminobutoxy}propan-2-one (1.4 g prepared as described in Example 214) sodium borohydride (1.5 g) and propan-2-ol (30 ml) was heated under reflux for 4.25 hours. The mixture was cooled and poured into water. The aqueous mixture was extracted with ether. The extract was dried and evaporated to give a residue which was heated at 90°/20 mm to leave 1-{4-[1-(4-chlorophenyl)cyclobutyl]-4-dimethylaminobutoxy}propan-2-ol as an oil the boiling point of which was not determined.

EXAMPLE 216

A mixture of 2-{4-[1-(4-chlorophenyl)cyclobutyl]-4-dimethylaminobutoxy}-N,N-3-oxapentamethyleneacetamide (4.9 g prepared as described in Example 214), ethylene glycol (30 ml) and 18N aqueous sodium hydroxide solution (10 ml) was heated under reflux for 2½ hours and then cooled. Water (30 ml) was added and the aqueous mixture washed with ether. The ether extracts were washed with 5N aqueous sodium hydroxide solution and the alkaline washings combined with the aqueous reaction mixture and the resulting mixture neutralised by addition of concentrated hydrochloric acid. The neutralised mixture was evaporated and the residue dried by azeotropic distillation with methanol and then propan-2-ol. The residue was mixed with propan-2-ol and the mixture filtered. The filtrate was evaporated and the residue was heated at 63°/0.7 mm to remove excess ethyleneglycol and then dissolved in ethanol (50 ml). Thionyl chloride (3.5 ml) was added dropwise with stirring and the mixture allowed to stand for 16 hours under anhydrous conditions. The reaction mixture was then poured into a mixture of ice and excess aqueous sodium bicarbonate solution. The mixture was extracted with ether and the extracts were dried and evaporated to give an oil which was mixed with ether. The mixture was filtered and a solution of maleic acid in ether was added to the filtrate to produce a gum. The supernatent was decanted and the residual gum washed with ether, which was decanted, several times and then basified with sodium bicarbonate. The product was extracted with ether and the extracts were dried and evaporated to give ethyl 2-{4-[1-(4-chlorophenyl)-cyclobutyl]-4-dimethylaminobutoxy}acetate. A sample of this material (2.8 g) was dissolved in methanol (300 ml). Ammonia gas was bubbled into the solution which was cooled in ice, saturated with ammonia gas and then evaporated and heated at 90°/20 mm to leave 2-{4-[1-(4-chlorophenyl)cyclobutyl]-4-dimethylaminobutoxy}acetamide a residual oil the boiling point of which was not determined.

EXAMPLE 217

A mixture of 1-[1-(4-chlorophenyl)cyclobutyl]-ethanone (40 g), N,N-dimethylhydrazine (50 ml), glacial acetic acid (2 ml) and ethanol (35 ml) was heated under reflux for 78 hours. Removal of the solvent gave a residue which was distilled (104°-106°/0.1 mm Hg) to give 1-[1-(4-chlorophenyl)cyclobutyl]ethanone N,N-dimethylhydrazone.

A solution of 1-[1-(4-chlorophenyl)cyclobutyl]-ethanone N,N-dimethylhydrazone (26 g) in tetrahydrofuran (50 ml) was added over a period of 30 minutes to a 0.29M solution of lithium diisopropylamide [prepared from diisopropylamine (11.55 g) and butyllithium (75 ml of a 1.55M solution in hexane) in tetrahydrofuran (320 ml)] at 12° C. The mixture was stirred at 0°-5° C. for two hours and then cooled to −65° C. Dimethyldisulphide (9.9 g) was added over a period of five minutes and the resulting mixture was stirred as it warmed to ambient temperature over a period of three hours. Water (400 ml) was added, the phases separated and the aqueous phase extracted with ether. The ether extracts and the organic phase of the reaction mixture were combined, washed with water and brine and evaporated to give an oil which was dissolved in ether (200 ml). The ether solution was extracted with 5N hydrochloric acid. The ether layer was evaporated to give an oil and the acid layer was stirred for 1 hour at ambient temperature and then heated at 90°-95° C. for 1 hour. The mixture was cooled and extracted with ether. Removal of the solvent gave an oil which was combined with the oil obtained earlier and distilled (145°-165° C./0.8 mm Hg) to give a distillate containing 62% 1-[1-(4-chlorophenyl)cyclobutyl]-2-methylthioethanone.

Crude 1-[1-(4-chlorophenyl)cyclobutyl]-2-methylthioethan-1-one (8.3 g prepared as described above), ammonium acetate (25 g) and sodium cyanoborohydride (2.6 g) were dissolved in methanol (120 ml). The solution was kept at room temperature for 19 days and then poured into water (300 ml) and basified to pH 8. The mixture was extracted with ether and the ethereal solution extracted with 2N hydrochloric acid. The acid solution was basified and extracted with ether. The extracts were dried and evaporated to give an oil which was purified by flash chromatography using ethyl acetate as eluant to give 1-[1-(4-chlorophenyl)cyclobutyl]-2-methylthioethylamine the boiling point of which was not determined.

EXAMPLE 218

In a similar manner to that described hereinbefore as Method K in Examples 174 to 189, the product of Example 217 was converted into N,N-dimethyl-1-[1-(4-chlorophenyl)cyclobutyl]-2-methylthioethylamine hydrochloride which was recrystallised from a mixture of acetone and light petroleum (m.p. 182° C.).

EXAMPLE 219

A solution of m-chloroperbenzoic acid (1.75 g) in dichloromethane (50 ml) was added over 30 minutes to a stirred solution of N,N-dimethyl-1-[1-(4-chlorophenyl)cyclobutyl]-4-methylthiobutylamine (2.4 g prepared in a similar manner to that described in Example 187) in dichloromethane (50 ml) at 0° C. The mixture was stirred at 0° C. for 1½ hours and then kept at <5° C. overnight. The resulting solution was washed with 2N sodium hydroxide solution then brine and then dried and evaporated to give an oil which was treated with petroleum ether (b.p. 40°-60° C.). The resulting mixture was filtered and the filtrate evaporated to give a residue which was dissolved in 2N hydrochloric acid. The solution was washed with ether, basified and extracted with ether. The extracts were dried and evaporated to give N,N-dimethyl-1-[1-(4-chlorophenyl)-cyclobutyl]-4-methylsulphinylbutylamine as an oil the boiling point of which was not determined.

EXAMPLE 220

A solution of dimethylsulphone (8.3 g), in dry tetrahydrofuran (150 ml) was added dropwise to a stirred ice-cold solution of butyllithium (30 ml of 2.6M solution in hexane). The mixture was stirred at room temperature for 15 minutes and then a solution of 1-(4-chlorophenyl)cyclobutanecarbonitrile (15 g) in tetrahydrofuran (25 ml) was added over 15 minutes and the resulting solution was heated under reflux for 16 hours. The solution was cooled and treated with water and the organic layer separated. The aqueous layer was extracted with ether and the ether extracts combined with the previously separated organic layer, dried and the solvents were removed by evaporation. The resulting oil crystallised, and the solid was washed with petroleum ether (b.p. 40°-60° C.) to give 1-[1-(4-chlorophenyl)cyclobutyl]-2-methylsulphonylvinylamine (m.p. 125°-126°).

A solution of 1-[1-(4-chlorophenyl)cyclobutyl]-2-methylsulphonylvinylamine (10 g), ammonium acetate (5 g), glacial acetic acid (7 ml) and sodium cyanoborohydride (5 g) in methanol (250 ml) was kept at room temperature for 12 days. The mixture was poured into water (750 ml) basified to pH 11 and extracted with dichloromethane. The organic extracts were washed with brine, dried and evaporated to give 1-[1-(4-chlorophenyl)cyclobutyl]-2-methylsulphonylethylamine (m.p. 134°-135°).

EXAMPLE 221

In a similar manner to that described in Example 220, 1-[1-(3,4-dichlorophenyl)cyclobutyl]-2-methylsulphonylethylamine (m.p. 156°–157°) was prepared.

EXAMPLES 222 AND 223

In a similar manner to that described hereinbefore as Method K in Examples 174 to 189, the products of Examples 220 and 221 were converted into N,N-dimethyl-1-[1-(4-chlorophenyl)cyclobutyl]-2-methylsulphonylethylamine maleate (m.p. 148°–149° C.) and N,N-dimethyl-1-[1-(3,4-dichlorophenyl)cyclobutyl]-2-methylsulphonylethylamine maleate (m.p. 143°–144° C.) respectively.

EXAMPLE 224

Pharmaceutical compositions containing any one of the compounds of formula I disclosed in the preceding Examples are prepared in the following manner.

EXAMPLE 224(a)

Tablets are prepared from the following ingredients:

|                     | Parts by Weight |
|---------------------|-----------------|
| Active Ingredient   | 50.0            |
| Lactose             | 78.5            |
| Polyvinylpyrrolidone| 5.0             |
| Maize Starch        | 15.0            |
| Magnesium Stearate  | 1.5             |

The active ingredient, the lactose and some of the starch are mixed and granulated with a solution of the polyvinylpyrrolidone ethanol. The granulate is mixed with the stearic acid and the rest of the starch and the mixture is compressed in a tabletting machine to give tablets containing a therapeutically effective amount of the active ingredient.

EXAMPLE 224(b)

Capsules are prepared in the following way. A mixture of the active ingredient (45 parts by weight) and lactose powder (205 parts by weight) is filled into hard gelatin capsules, each capsule containing a therapeutically effective amount of the active ingredient.

EXAMPLE 224(c)

In the preparation of enteric coated tablets, the tablets described in EXAMPLE 224(a) are given a thin coat of shellac varnish, followed by 20 coats of cellulose acetate phthalate in a manner well known in the art. In a similar manner the capsules of Example 224(b) may be provided with an enteric coating.

EXAMPLE 224(d)

Vials containing a solution of water-soluble compounds of the present invention suitable for injection are prepared from the following ingredients:

|                       |              |
|-----------------------|--------------|
| Active Ingredient     | 1100 g       |
| Mannitol              | 1100 g       |
| Water, freshly distilled | to 11 liters |

The active ingredient and mannitol are dissolved in some of the water and the volume of the solution is adjusted to 11 litres. The resulting solution is sterilised by filtration and filled into sterile vials each containing a therapeutically effective amount of the active ingredient.

We claim:

1. A compound of the formula I

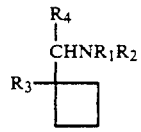

or a pharmaceutically acceptable salt thereof wherein one or both of $R_1$ and $R_2$ are H, cyclohexyl or an alkyl moiety of 1 to 4 carbon atoms unsubstituted or substituted by morpholino or the group $-NR_1R_2$ is morpholino or piperidino, $R_3$ is phenyl, naphthyl or phenyl substituted by 1 to 3 substituents selected from the group consisting of fluoro, chloro, bromo, trifluoromethyl, methyl, methoxy, methylthio and phenyl and $R_4$ is selected from the group consisting of 3-hydroxypropyl, 2-hydroxy-1,2-dimethylpropyl, 4-hydroxybutyl, 4-hydroxypentyl, 6-hydroxyhexyl, 6-hydroxyheptyl, a group of the formula II

wherein $R_6$ is H, methyl or ethyl and $R_7$ is methyl, ethyl, propyl, isopropyl, isobutyl or pentenyl and a group of the formula III

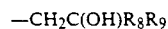

wherein $R_8$ is H, methyl, ethyl, propyl or isopropyl and $R_9$ is methyl, ethyl, propyl, isopropyl, isobutyl, tert-butyl, cyclopropyl, trifluoromethyl, 1-methylthioethyl, methoxymethyl, ethoxymethyl, 2-methoxyethyl, 2-ethoxyethyl or morpholinomethyl.

2. A compound according to claim 1 wherein $-NR_1R_2$ is amino, N-methylamino, N,N-dimethylamino, N,N-diethylamino, N-butyl-N-methylamino, N-methyl-N-(2-morpholinoethyl)amino, N-cyclohexyl-N-methylamino, piperidino or morpholino.

3. A compound according to claim 1 wherein $R_3$ is phenyl, 2-naphthyl, 4-chlorophenyl, 3-chlorophenyl, 3,4-dichlorophenyl, 4-bromophenyl, 4-fluorophenyl, 3-fluorophenyl, 4-methylphenyl, 4-methoxyphenyl, 4-methylthiophenyl, 3-trifluoromethylphenyl or 4-biphenylyl.

4. A compound according to claim 1 wherein $R_4$ is 1-hydroxyethyl, 1-hydroxypropyl, 1-hyhdroxy-1-methylethyl, 1-hydroxybutyl, 1-hydroxy-1-methylpropyl, 1-hydroxy-2-methylpropyl, 1-hydroxy-3-methylbutyl, 1-hydroxy-5-hexenyl, 2-hydroxybutyl, 2-hydroxy-2-methylpropyl, 2-hydroxy-2-2-methyl-3-morpholinopropyl, 2-hydroxy-2-trifluoromethylpropyl, 2-cyclopropyl-2-hydroxypropyl, 2-hydroxybutyl, 2-hydroxy-2-methylbutyl, 2-ethyl-2-hydroxybutyl, 2-ethyl-2-hydroxy-3-methyl-butyl, 2-hydroxy-2,3,3-trimethylbutyl, 2-hydroxy-2-methyl-3-methylthiobutyl, 2-hydroxy-2-methylpentyl, 2-hydroxy-2,4-dimethylpentyl, 2-hydroxy-3-methoxy-2-methylpropyl, 2-hydroxy-2-(methoxymethyl)butyl, 2-(ethoxymethyl)-2-hydroxybutyl, 2-hydroxy-2-(methoxymethyl)pentyl, 2-hydroxy-4-methoxy-2-methylbutyl, 2-ethyl-2-hydroxy-4-methoxybutyl or 4-ethoxy-2-hydroxy-2-methylbutyl.

5. A compound according to claim 1 which is:

4-amino-2-methyl-4-(1-phenylcyclobutyl)butan-2-ol
1-amino-1-[1-(4-chlorophenyl)cyclobutyl]-3-methylpentan-3-ol
1-amino-1-[1-(4-chlorophenyl)cyclobutyl]-3-ethylpentan-3-ol
1-amino-3-ethyl-1-[1-(4-fluorophenyl)cyclobutyl]-pentan-3-ol
1-dimethylamino-3-ethyl-1-[1-(4-fluorophenyl)cyclobutyl]pentan-3-ol
4-[1-(4-chlorophenyl)cyclobutyl]-4-dimethylamino-2-methylbutan-2-ol
4-amino-4-[1-(4-biphenylyl)cyclobutyl]-2-methylbutan-2-ol
1-[1-(4-chlorophenyl)cyclobutyl]-1-dimethylamino-2-methylpropan-2-ol
or a pharmaceutically acceptable salt thereof.

6. A pharmaceutical composition for the treatment of depression in humans which comprises an antidepressantly effective amount of a compound of the formula I

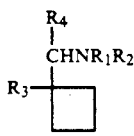

or a pharmaceutically acceptable salt thereof wherein one or both of $R_1$ and $R_2$ are H, cyclohexyl or an alkyl moiety of 1 to 4 carbon atoms unsubstituted or substituted by morpholino or the group $—NR_1R_2$ is morpholino or piperidino, $R_3$ is phenyl, naphthyl or phenyl substituted by 1 to 3 substituents selected from the group consisting of fluoro, chloro, bromo, trifluoromethyl, methyl, methoxy, methylthio and phenyl and $R_4$ is selected from the group consisting of 3-hydroxypropyl, 2-hydroxy-1,2-dimethylpropyl, 4-hydroxybutyl, 4-hydroxypentyl, 6-hydroxyhexyl, 6-hydroxyheptyl, a group of the formula II $—C(OH)R_6R_7$     II

wherein $R_6$ is H, methyl or ethyl and $R_7$ is methyl, ethyl, propyl, isopropyl, isobutyl or pentenyl and a group of the formula III $—CH_2C(OH)R_8R_9$     III

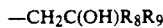

wherein $R_8$ is H, methyl, ethyl, propyl or isopropyl and $R_9$ is methyl, ethyl, propyl, isopropyl, isobutyl, tert-butyl, cyclopropyl, trifluoromethyl, 1-methylthioethyl, methoxymethyl, ethoxymethyl, 2-methoxyethyl, 2-ethoxyethyl or morpholinomethyl, in combination with a pharmaceutically acceptable carrier.

7. A pharmaceutical composition according to claim 6 wherein $—NR_1R_2$ is amino, N-methylamino, N,N-dimethylamino, N,N-diethylamino, N-butyl-N-methylamino, N-methyl-N-(2-morpholinoethyl)amino, N-cyclohexyl-N-methylamino, piperidino or morpholino.

8. A pharmaceutical composition according to claim 6 wherein $R_3$ is phenyl, 2-naphthyl, 4-chlorophenyl, 3-chlorophenyl, 3,4-dichlorophenyl, 4-bromophenyl, 4-fluorophenyl, 3-fluorophenyl, 4-methylphenyl, 4-methoxyphenyl, 4-methylthiophenyl, 3-trifluoromethylphenyl or 4-biphenylyl.

9. A pharmaceutical composition according to claim 6 wherein $R_4$ is 1-hydroxyethyl, 1-hydroxypropyl, 1-hydroxy-1-methyl-ethyl, 1-hydroxybutyl, 1-hydroxy-1-methylpropyl, 1-hydroxy-2-methylpropyl, 1-hydroxy-2-methylpropyl, 1-hydroxy-3-methylbutyl, 1-hydroxy-5-hexenyl, 2-hydroxybutyl, 2-hydroxy-2-methylpropyl, 2-hydroxy-2-methyl-3-morpholinopropyl, 2-hydroxy-2-trifluoromethylpropyl, 2-cyclopropyl-2-hydroxypropyl, 2-hydroxybutyl, 2-hydroxy-2-methylbutyl, 2-ethyl-2-hydroxybutyl, 2-ethyl-2-hydroxy-3-methylbutyl, 2-hydroxy-2,3,3-trimethylbutyl, 2-hydroxy-2-methyl-3-methylthiobutyl, 2-hydroxy-2-methylpentyl, 2-hydroxy-2,4-dimethylpentyl, 2-hydroxy-3-methoxy-2-methylpropyl, 2-hydroxy-2-(methoxymethyl)butyl, 2-(ethoxymethyl)-2-hydroxybutyl, 2-hydroxy-2-(methoxymethyl)pentyl, 2-hydroxy-4-methoxy-2-methylbutyl, 2-ethyl-2-hydroxy-4-methoxybutyl or 4-ethoxy-2-hydroxy-2-methylbutyl.

10. A method of treating depression in humans which comprises administering to a human in need thereof an antidepressantly effective amount of a compound of the formula I

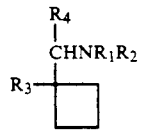

or a pharmaceutically acceptable salt thereof wherein one or both of $R_1$ and $R_2$ are H, cyclohexyl or an alkyl moiety of 1 to 4 carbon atoms unsubstituted or substituted by morpholino or the group $—NR_1R_2$ is morpholino or piperidino, $R_3$ is phenyl, naphthyl or phenyl substituted by 1 to 3 substituents selected from the group consisting of fluoro, chloro, bromo, trifluoromethyl, methyl, methoxy, methylthio and phenyl and $R_4$ is selected from the group consisting of 3-hydroxypropyl, 2-hydroxy-1,2-dimethylpropyl, 4-hydroxybutyl, 4-hydroxypentyl, 6-hydroxyhexyl, 6-hydroxyheptyl, a group of the formula II $—C(OH)R_6R_7$     II

wherein $R_6$ is H, methyl or ethyl and $R_7$ is methyl, ethyl, propyl, isopropyl, isobutyl or pentenyl and a group of the formula III $—CH_2C(OH)R_8R_9$     III

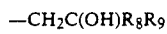

wherein $R_8$ is H, methyl, ethyl, propyl or isopropyl and $R_9$ is methyl, ethyl, propyl, isopropyl, isobutyl, tert-butyl, cyclopropyl, trifluoromethyl, 1-methylthioethyl, methoxymethyl, ethoxymethyl, 2-methoxyethyl, 2-ethoxyethyl or morpholinomethyl, in combination with a pharmaceutically acceptable carrier.

11. A method according to claim 10 wherein $—NR_1R_2$ is amino, N-methylamino, N,N-dimethylamino, N,N-diethylamino, N-butyl-N-methylamino, N-methyl-N-(2-morpholinoethyl)amino, N-cyclohexy-N-methylamino, piperidino or morpholino.

12. A method according to claim 10 wherein $R_3$ is phenyl, 2-naphthyl, 4-chlorophenyl, 3-chlorophenyl, 3,4-dichlorophenyl, 4-bromophenyl, 4-fluorophenyl, 3-fluorophenyl, 4-methylphenyl, 4-methoxyphenyl, 4-methylthiophenyl, 3-trifluoromethylphenyl or 4-biphenylyl.

13. A method according to claim 10 wherein $R_4$ is 1-hydroxyethyl, 1-hydroxypropyl, 1-hydroxy-1-methylethyl, 1-hydroxybutyl, 1-hydroxy-1-methylpropyl, 1-hydroxy-2-methylpropyl, 1-hydroxy-3-methylbutyl, 1-hydroxy-5-hexenyl, 2-hydroxybutyl, 2-hydroxy-2-methylpropyl, 2-hydroxy-2-methyl-3-morpholinopropyl, 2-hydroxy-2-trifluoromethylpropyl, 2-cyclopropyl-2-hyroxypropyl, 2-hydroxybutyl, 2-hydroxy-2-methylbutyl, 2-ethyl-2-hydroxybutyl, 2-ethyl-2-hydroxy-3-methylbutyl, 2-hydroxy-2,3,3-trimethylbutyl, 2-hydroxy-2-methyl-3-methylthiobutyl, 2-hydroxy-2-methylpentyl, 2-hydroxy-2,4-dimethylpentyl, 2-hydroxy-3-methoxy-2-methylpropyl, 2-hydroxy-2-(methoxymethyl)butyl, 2-(ethoxymethyl)-2-hydroxybutyl, 2-hydroxy-2-(methoxymethyl)pentyl, 2-hydroxy-4-methoxy-2-methylbutyl, 2-ethyl-2-hydroxy-4-methoxybutyl or 4-ethoxy-2-hydroxy-2-methylbutyl.

14. A pharmaceutical composition according to claim 6 wherein the compound is:
4-amino-2-methyl-4-(1-phenylcyclobutyl) butan-2-ol,
1-amino-1-[1-(4-chloropheny)cyclobutyl]-3-methyl-pentan-3-ol,
1-amino-1-[1-4-chlorophenyl)cyclobutyl]-3-ethyl-pentan-3-ol,
1-amino-3-ethyl-1-[1-(4-fluorophenyl)cyclobutyl]-pentan-3-ol,
1-dimethylamino-3-ethyl-1-[1-(4-fluorophenyl)cyclobutyl]-pentan-3-ol,
4-{1-(4-chlorophenyl)cyclobutyl}-4-dimethylamino-2-methylbutan-2-ol,
4-amino-4-[1-(4-biphenyl)cyclobutyl]-2-methylbutan-2-ol,
1-[1-(4-chlorophenyl)cyclobutyl]-1-dimethylamino-2-methylpropan-2-ol,
or a pharmaceutically acceptable salt thereof.

15. A method according to claim 10 wherein the compound is:
4-amino-2-methyl-4-(1-phenylcyclobutyl)butan-2-ol,
1-amino-1-[4-chloropheny)cyclobutyl]-3-methyl-pentan-3-ol,
1-amino-1-[1-(4-chlorophenyl)cyclobutyl]-3-ethyl-pentan-3-ol, 1-amino-3-ethyl-1-[1-(4-fluorophenyl)cyclobutyl]-pentan-3-ol,
1-dimethylamino-3-ethyl-1-[1-(4-fluorophenyl)cyclobutyl]-pentan-3-ol,
4-{1(4-chlorophenyl)cyclobutyl}-4-dimethylamino-2-methylbutan-2-ol,
4-amino-4-[1-(4-biphenyl)cyclobutyl]-2-methylbutan-2-ol,
1-[1-(4-chlorophenyl)cyclobutyl]-1-dimethylamino-2-methylpropan-2-ol,
or pharmaceutically acceptable salt thereof.

* * * * *